United States Patent
Nguyen et al.

(10) Patent No.: US 10,765,745 B2
(45) Date of Patent: Sep. 8, 2020

(54) MULTIFUNCTIONAL NANOPARTICLE SYSTEMS AND METHODS FOR CANCER DIAGNOSIS AND COMBINATION THERAPY

(71) Applicant: BOARD OF REGENTS, THE UNIVERSITY OF TEXAS SYSTEM, Austin, TX (US)

(72) Inventors: Kytai Nguyen, Grand Prairie, TX (US); Jyothi Menon, Oxford (GB); Debabrata Saha, Carrollton, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 15/260,835

(22) Filed: Sep. 9, 2016

(65) Prior Publication Data

US 2017/0065523 A1    Mar. 9, 2017

Related U.S. Application Data

(60) Provisional application No. 62/215,841, filed on Sep. 9, 2015.

(51) Int. Cl.

| | |
|---|---|
| *A61K 41/00* | (2020.01) |
| *A61K 31/7068* | (2006.01) |
| *A61K 49/18* | (2006.01) |
| *A61K 47/69* | (2017.01) |
| *A61K 31/5377* | (2006.01) |
| *A61K 47/55* | (2017.01) |
| *A61K 33/24* | (2019.01) |
| *A61K 9/51* | (2006.01) |

(52) U.S. Cl.
CPC ...... *A61K 41/0038* (2013.01); *A61K 31/5377* (2013.01); *A61K 31/7068* (2013.01); *A61K 33/24* (2013.01); *A61K 47/551* (2017.08); *A61K 47/6937* (2017.08); *A61K 49/1857* (2013.01); *A61K 9/5153* (2013.01); *A61K 9/5169* (2013.01)

(58) Field of Classification Search
CPC ............ A61K 41/0038; A61K 49/1857; A61K 47/6937; A61K 31/5377; A61K 47/551; A61K 33/24; A61K 31/7068; A61K 9/5169; A61K 9/5153
See application file for complete search history.

(56) References Cited

U.S. PATENT DOCUMENTS

| | | | |
|---|---|---|---|
| 2014/0005379 A1* | 1/2014 | Gu ................ | A61K 47/26 536/112 |
| 2014/0255502 A1* | 9/2014 | Chen .............. | A61K 9/5115 424/492 |
| 2014/0363514 A1* | 12/2014 | Koyakutty ...... | A61K 31/437 424/491 |
| 2016/0116464 A1* | 4/2016 | Stayton .......... | A61K 49/1839 435/5 |

OTHER PUBLICATIONS

Zhang et al., Int'l J. Biol. Macromoleclues, 51 (2012) 1109-1115.*
Mauceri et al., Oncol Rep. 27:1625-1629, 2012.*
Huang et al., J. Controlled Release 73 (2001) 121-136.*

* cited by examiner

*Primary Examiner* — Robert S Cabral
(74) *Attorney, Agent, or Firm* — J. Clinton Wimbish; Nexsen Pruet, PLLC

(57) ABSTRACT

In one aspect, compositions comprising a population of core-shell nanoparticles are described herein. In some cases, the population of core-shell nanoparticles comprises a core component and a shell component encapsulating or surrounding the core component. Additionally, one or more radiosensitizers are disposed in or dispersed throughout the core component, or an interior region of the core component. Similarly, one or more chemotherapeutic agents are disposed in or dispersed throughout the shell component, or an interior region of the shell component. Moreover, in some cases, the core component is formed from one or more biodegradable polymers. Further, in some instances, the shell component is formed from one or more stimuli responsive polymers, such as a temperature-responsive polymer and/or pH-responsive polymer.

26 Claims, 24 Drawing Sheets

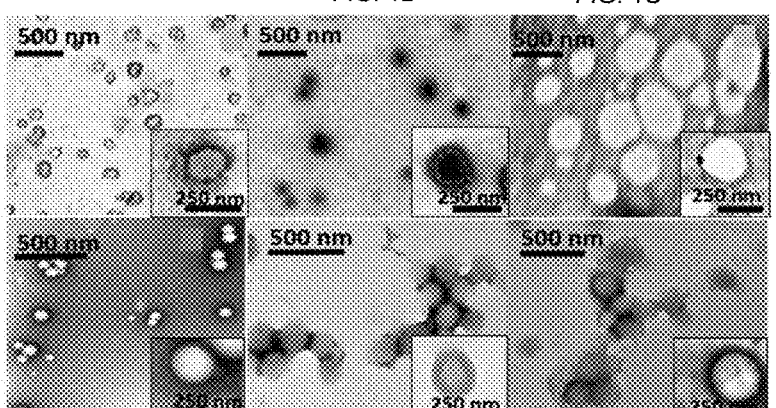
FIG. 1A   FIG. 1B   FIG. 1C
FIG. 1D   FIG. 1E   FIG. 1F
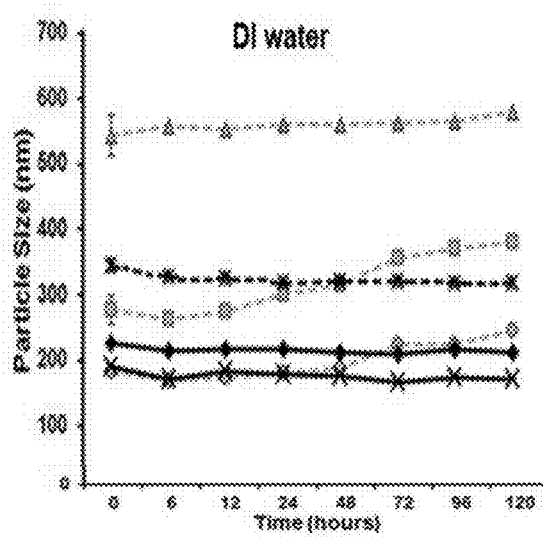
FIG. 2A
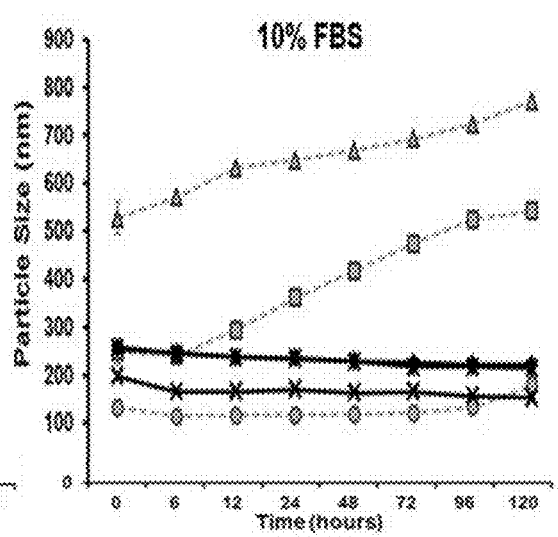
FIG. 2B

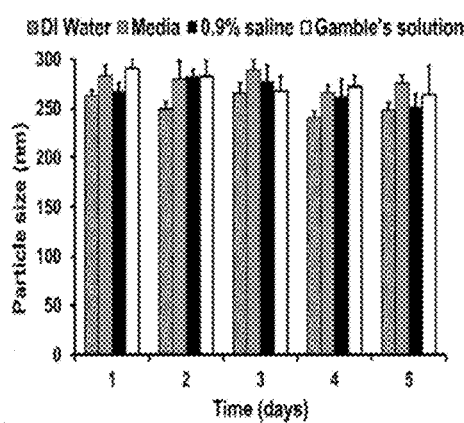
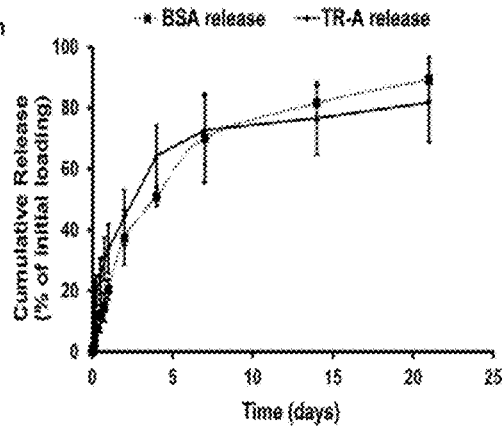
FIG. 11A      FIG. 11B
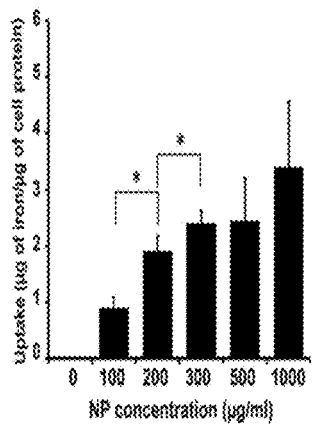
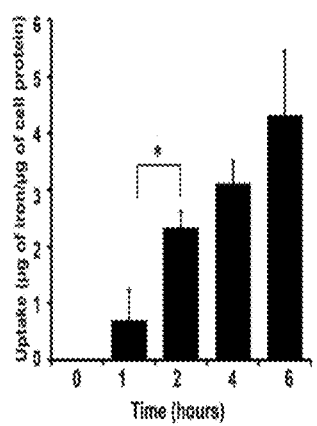
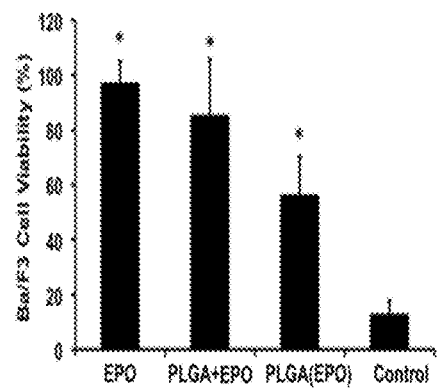
FIG. 12A      FIG. 12B      FIG. 12C

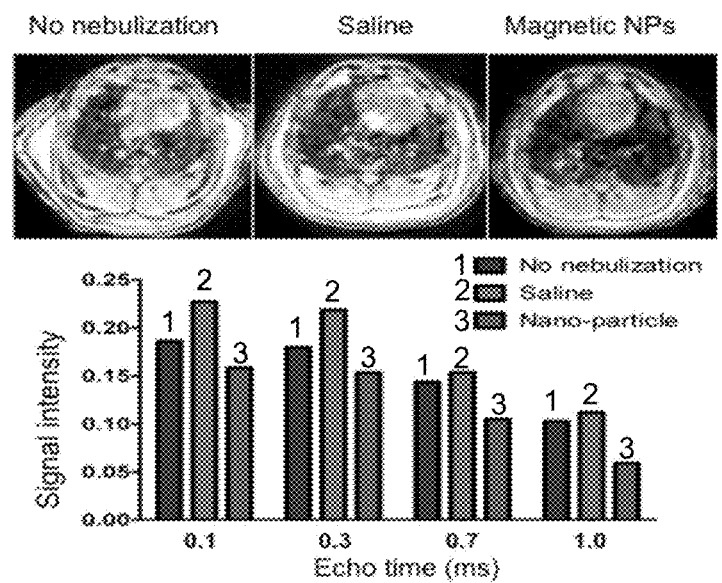
FIG. 13
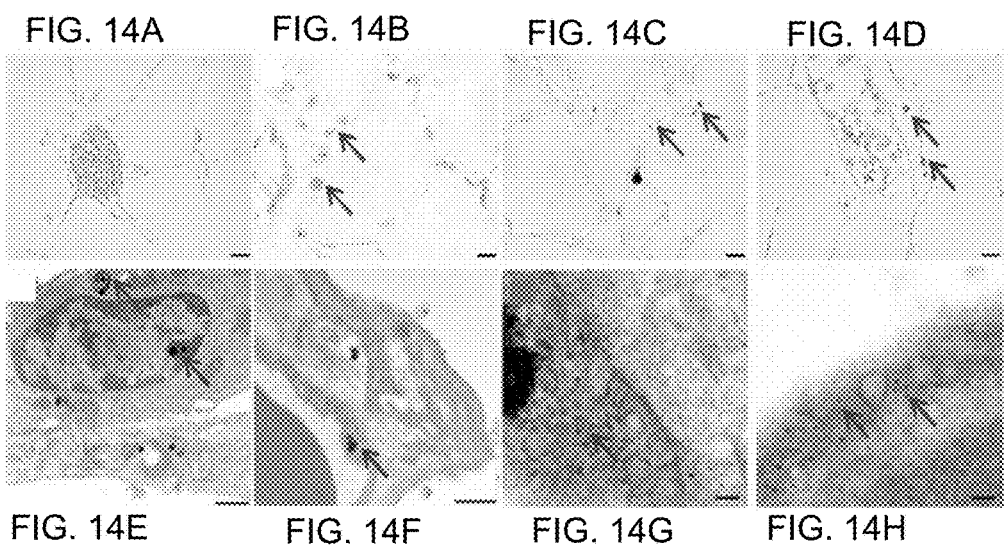
FIG. 14A  FIG. 14B  FIG. 14C  FIG. 14D
FIG. 14E  FIG. 14F  FIG. 14G  FIG. 14H

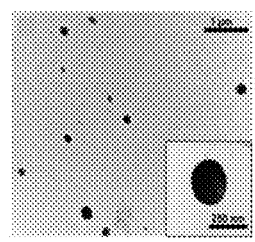 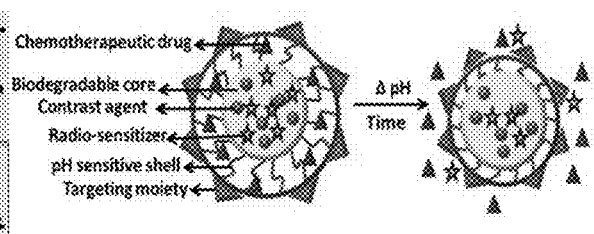
FIG. 17A        FIG. 17B
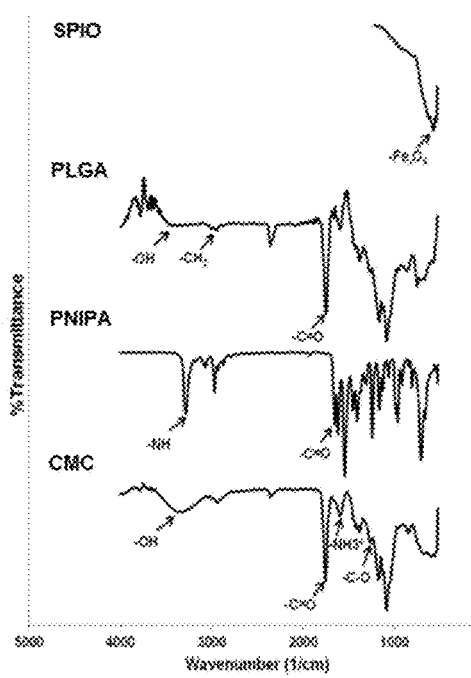 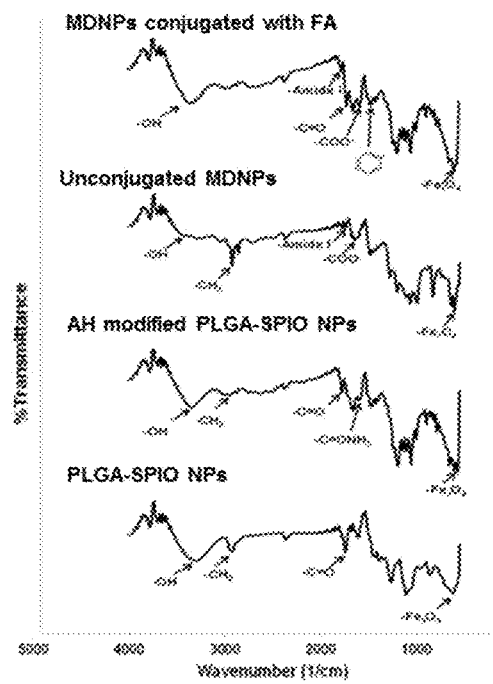
FIG. 18A        FIG. 18B

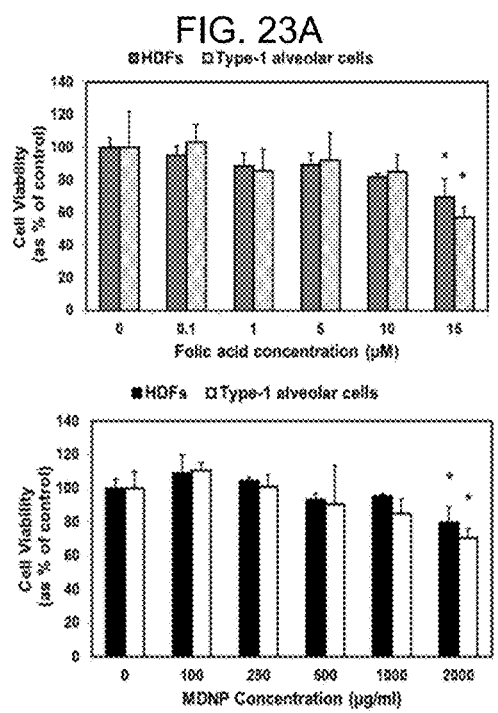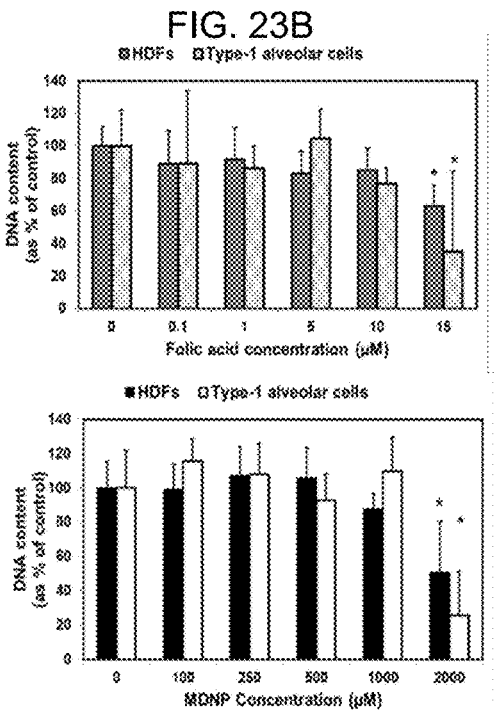
FIG. 23A  FIG. 23B  FIG. 23C  FIG. 23D
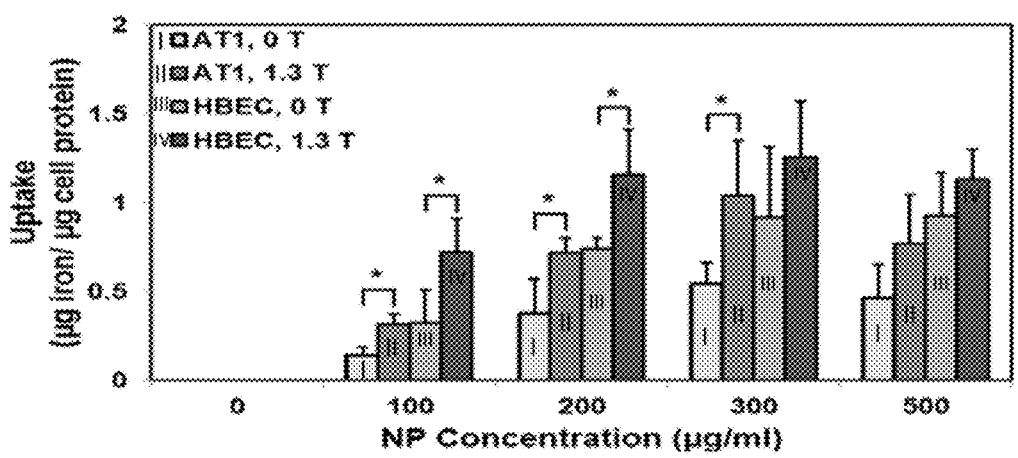
FIG. 24A

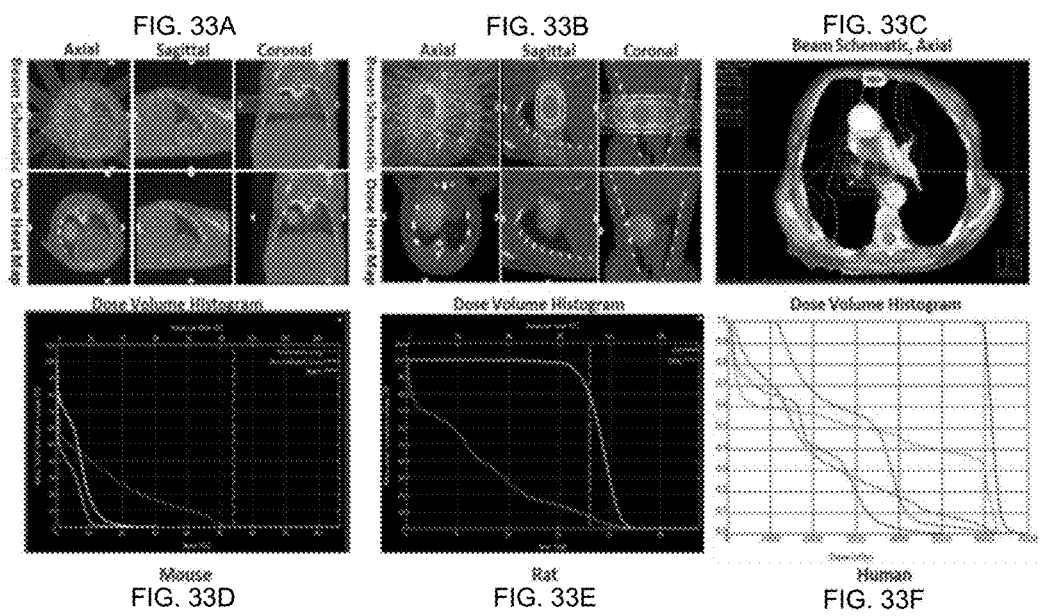

MULTIFUNCTIONAL NANOPARTICLE SYSTEMS AND METHODS FOR CANCER DIAGNOSIS AND COMBINATION THERAPY

CROSS REFERENCE TO RELATED APPLICATIONS

This application claims priority pursuant to 35 U.S.C. § 119(e) to U.S. Provisional Patent Application Ser. No. 62/215,841, filed on Sep. 9, 2015, which is hereby incorporated by reference in its entirety.

FIELD

This invention relates to core-shell nanoparticles and, in particular, to multifunctional core-shell nanoparticles for use in theranostic applications, including systems and methods for cancer diagnosis and treatment.

BACKGROUND

Lung cancer is the deadliest form of cancer and accounts for nearly 1.6 million newly diagnosed cancer cases around the world annually. Further, the 5-year survival rate of lung cancer patients is less than 15%, partly due to the advanced stage of the disease at the time of diagnosis.

Conventional lung cancer treatment strategies include surgery, radiation therapy, and chemotherapy. These strategies have limitations, such as, for example, high temporary remission and severe adverse side effects. Moreover, surgical removal of lung cancer tumors is not always feasible in some patients. For example, many non-small-cell lung cancer (NSCLC) patients have un-resectable tumors. For several years, the main treatment for these patients has been radiotherapy (RT); however, the 5-year overall survival rate of RT patients is about 5%. Poor overall survival rates in NSCLC patients may also be attributed to intrinsic radiation resistance due to the increased ability to repair DNA damage after radiation therapy (RT).

Therefore, it is crucial to develop improved materials, methods, and systems that can overcome the above limitations and provide targeted and controlled therapy for effective lung cancer treatment for these patients and others.

SUMMARY

In one aspect, compositions are described herein which, in some embodiments, can provide one or more advantages compared to some other compositions, including for the diagnosis and/or treatment of cancer, such as lung cancer. For example, in some instances, a composition described herein is a multifunctional composition that can provide and/or enhance multiple modalities of cancer diagnosis and/or treatment. In some such cases, a multifunctional composition described herein can provide or deliver chemotherapy and also enhance the efficacy of radiation therapy.

Additionally, in some embodiments, a composition described herein can provide and/or deliver a plurality of differing chemotherapeutic agents to a tumor environment at varying rates, for achieving synergistic effects and treatment. Moreover, in some instances, a composition described herein can target a desired tumor or cell population. A composition described herein can also provide "on demand" delivery of chemotherapeutic agents and/or other agents. Further, in some cases, a composition described herein can include a contrast agent and/or an imaging agent sequentially or at the same time as it provides therapeutic effect.

In some embodiments, a composition described herein comprises a population of core-shell nanoparticles. The core-shell nanoparticles comprise a core component and a shell component encapsulating or surrounding the core component. Additionally, one or more radiosensitizers are disposed in or dispersed throughout the core component, or an interior region of the core component. Similarly, one or more chemotherapeutic agents are disposed in or dispersed throughout the shell component, or an interior region of the shell component. Moreover, in some cases, the core component is formed from one or more biodegradable polymers or oligomers. Further, in some instances, the shell component is formed from one or more stimuli responsive polymers or oligomers. For example, in some embodiments, the shell component is temperature-responsive and/or pH-responsive or is formed from a temperature-responsive and/or pH-responsive polymer. Core-shell nanoparticles having such a structure, in some instances, can provide a burst release of one or more chemotherapeutic agents disposed within or dispersed throughout the shell component, as well as a sustained release of one or more radiosensitizers disposed within or dispersed throughout the core component.

Further, in some cases, the population of core-shell nanoparticles of a composition described herein exhibits simultaneous release of at least a portion of the one or more radiosensitizers from the core component and at least a portion of the one or more chemotherapeutic agents from the shell component. Additionally, in some such instances, the core-shell nanoparticles can exhibit a biphasic overall release profile in which a burst release of one or more species (e.g., one or more radiosensitizers and/or one or more chemotherapeutic agents) is followed by a sustained release of one or more species (e.g., one or more radiosensitizers and/or one or more chemotherapeutic agents). Other release profiles are also possible.

In addition, in some cases, a composition described herein further comprises a contrast agent and/or an imaging agent disposed in or dispersed throughout the core component and/or the shell component. A composition described herein may also comprise a targeting agent or ligand attached to the outer surface of the core-shell nanoparticles of the composition. In some cases, such a composition can be delivered selectively to a desired location within a patient, such as a tumor site. In addition, a composition described herein can also be used to image such a location through the contrast agent and/or imaging agent.

Moreover, in some instances, a population of core-shell nanoparticles described herein has an average particle size or diameter of about 300 nm or less, and in some embodiments about 250 nm or less. The population of core-shell nanoparticles may also have a negative zeta potential, including a large negative zeta potential. For instance, in some embodiments, the negative zeta potential has an absolute value of at least 10 mV, and in some embodiments the negative zeta potential has an absolutely value of 10 mV or more. A population of core-shell nanoparticles having such a size distribution and surface charge, in some embodiments, can be stable in vivo for clinically significant periods of time and may also exhibit a biodistribution profile that promotes therapeutic efficacy of the nanoparticles and/or reduces toxicity or undesired side effects of the nanoparticles.

In another aspect, methods of diagnosing and/or treating a cancer are described herein. In some cases, such a method comprises administering to a patient in need thereof a composition described hereinabove. For example, in some embodiments, the composition comprises a population of core-shell nanoparticles, the core-shell nanoparticles comprising a core component; a shell component encapsulating or surrounding the core component; one or more radiosensitizers disposed in or dispersed throughout the core component; and one or more chemotherapeutic agents disposed in or dispersed throughout the shell component, wherein the core component is formed from one or more biodegradable polymers; and wherein the shell component is formed from one or more stimuli responsive polymers. Additionally, in some cases, the composition is administered to the patient as an aerosol or inhalant via a nebulizer. In other instances, the composition is administered to the patient as a liquid or powder. The composition may also be administered to the patient intravenously. Further, the cancer, in some embodiments, comprises lung cancer such as Non-Small Cell Lung Cancer (NSCLC).

Moreover, in some cases, a method described herein further comprises administering radiation therapy to the patient following administration of the composition to the patient. A method described herein can also comprise imaging the core-shell nanoparticles (or a portion of the patient in which the core-shell nanoparticles are disposed) following administration of a composition described herein to the patient. Such imaging can occur before, during, or after administrating radiation therapy to the patient. In this manner, a method described herein can be used both to diagnose and treat cancer in a patient, including in a simultaneous or a sequential manner.

In still another aspect, methods of making a core-shell nanoparticle are described herein. In such cases, the method comprises providing a core component; disposing one or more radiosensitizers within an interior region of the core component; forming a shell component over the core component; and disposing one or more chemotherapeutic agents with an interior region of the shell component.

Moreover, in some instances, the method further comprises disposing a contrast agent and/or an imaging agent within the interior region of the core component and/or within the interior region of the shell component. Additionally, in some embodiments, a method described herein further comprises attaching a targeting agent or ligand to the outer surface of the core-shell nanoparticle.

These and other embodiments are described in more detail in the detailed description which follows.

BRIEF DESCRIPTION OF THE FIGURES

FIGS. 1A-1F are TEM images of nanoparticles (NPs) according to some embodiments described herein.

FIGS. 2A-2D graphically illustrate the results of stability studies conducted on NPs according to some embodiments described herein.

FIGS. 11A-11B graphically illustrate the results from studies of NPs according to some embodiments described herein.

FIGS. 12A-12B graphically illustrate the results of cell uptake studies of NPs according to some embodiments described herein.

FIG. 12C graphically illustrates the results of cell viability studies of NPs according to some embodiments described herein.

FIG. 13 graphically illustrates MRI signal intensity changes following inhalation NPs according to some embodiments described herein.

FIGS. 14A-14H are microscopy images lung tissue illustrating inhaled NPs according to some embodiments described herein.

FIGS. 16A-16C graphically illustrate binding kinetic curves of ligand-conjugated NPs with specific lung cells according to some embodiments described herein.

FIG. 17A is a TEM image of NPs according to some embodiments described herein.

FIG. 17B is a schematic illustration of the behavior associated with NPs in response to changes in temperature and pH according to some embodiments described herein.

FIGS. 18A-18B graphically illustrate FTIR spectra of individual components of NPs according to some embodiments described herein.

FIGS. 19A-19C illustrate magnetic properties of NPs according to some embodiments described herein.

FIGS. 20A-20B graphically illustrate changes in NP size associated with changes in environmental pH and temperature according to some embodiments described herein.

FIGS. 21A-21B graphically illustrate the results from stability and degradation studies of NPs according to some embodiments described herein.

FIGS. 22A-22B graphically illustrate the release characteristics associated with the NP core and shell components according to some embodiments described herein.

FIGS. 23A-23D depict in vitro folic acid and folic acid-conjugated NP cytocompatibility studies associated with lung cancer cells according to some embodiments described herein.

FIGS. 24A-24B graphically illustrates the cellular uptake of NPs by lung cells and lung cancer cells according to some embodiments described herein.

Figure 25:
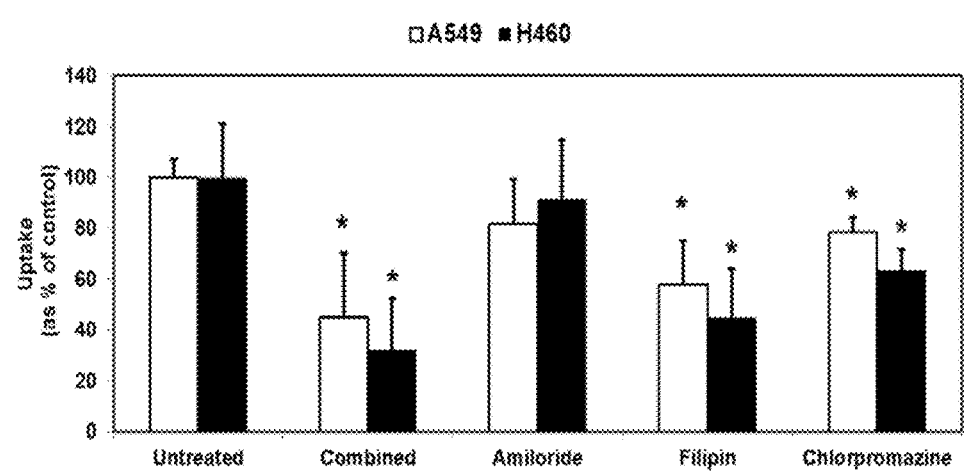

FIG. 25 graphically illustrates the mechanism of NP uptake by lung cancer cells according to some embodiments described herein.

Figure 26A:
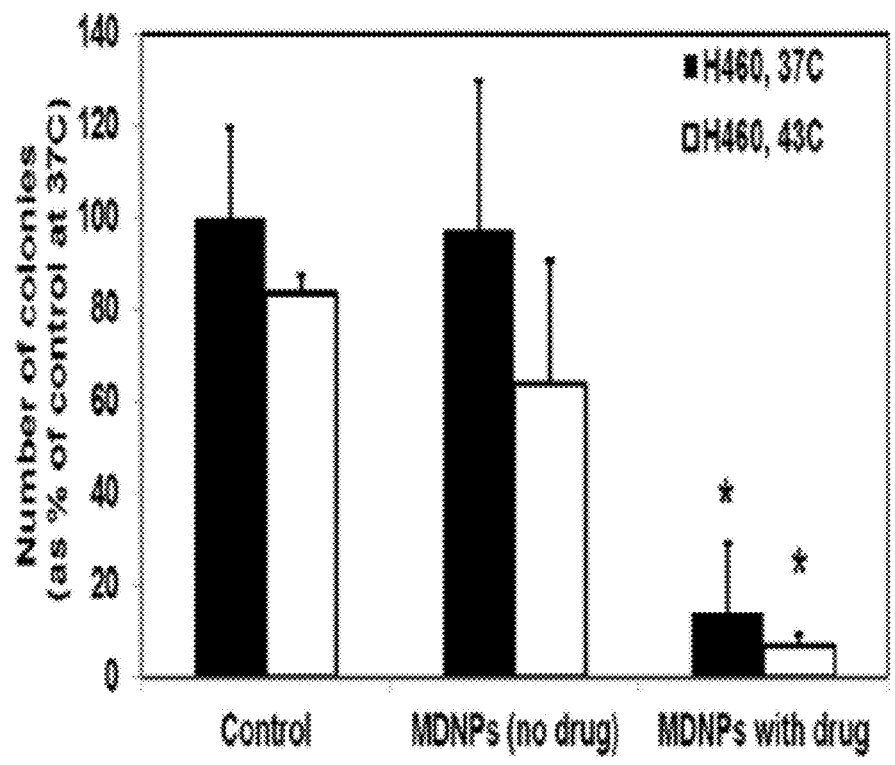
Figure 26B:
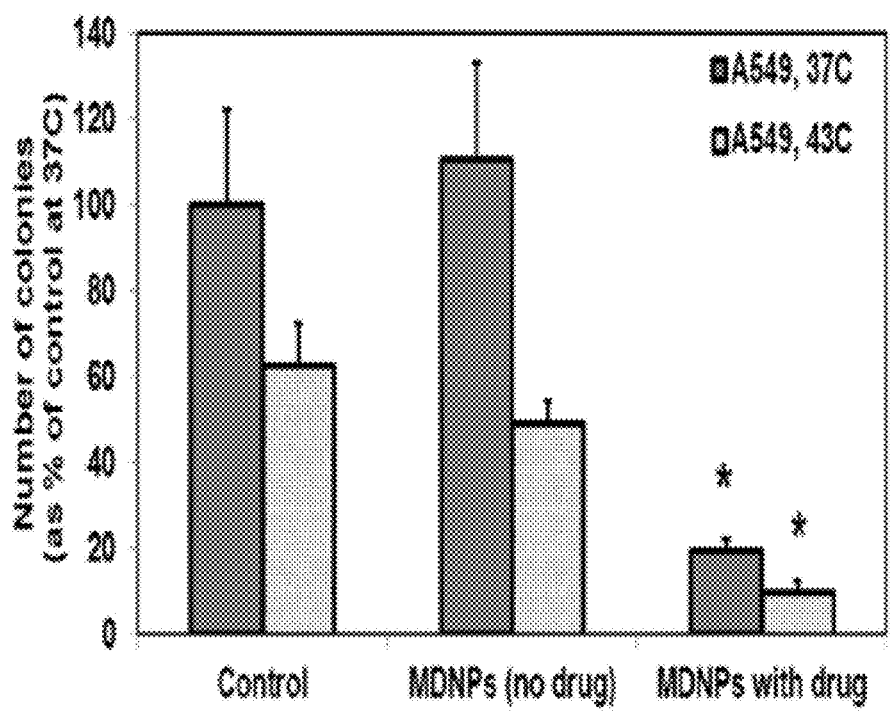

FIGS. 26A-26B graphically illustrate the results of various cancer cell colony formation studies of NPs according to some embodiments described herein.

Figure 27A:
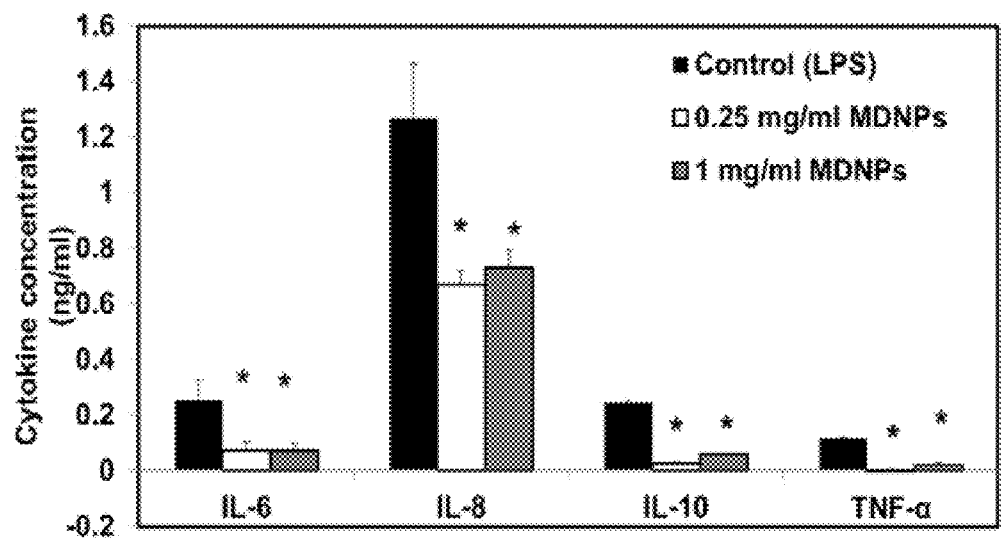
Figure 27B:
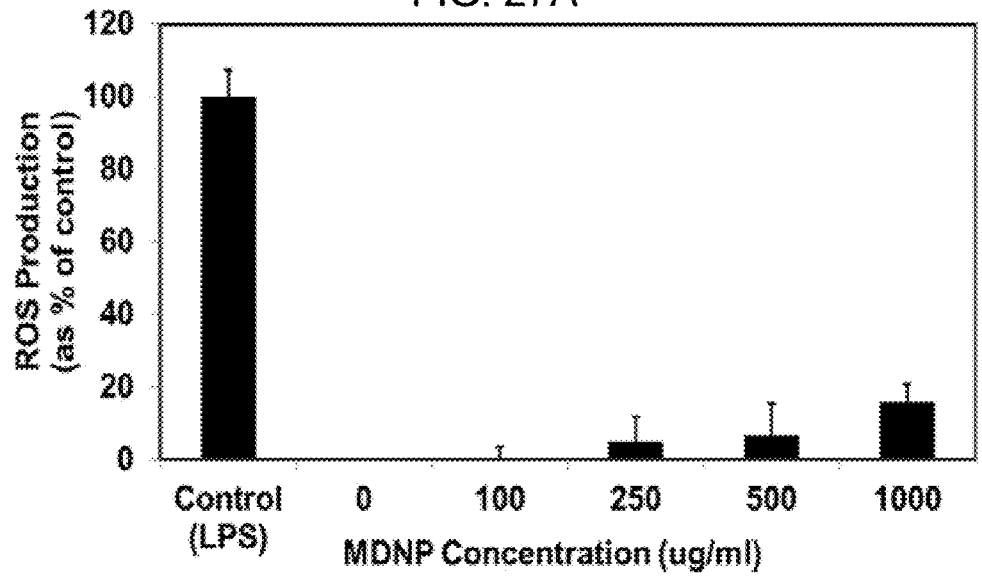

FIGS. 27A-27B graphically illustrate the results of cell activation study according to some embodiments described herein.

Figure 28A:
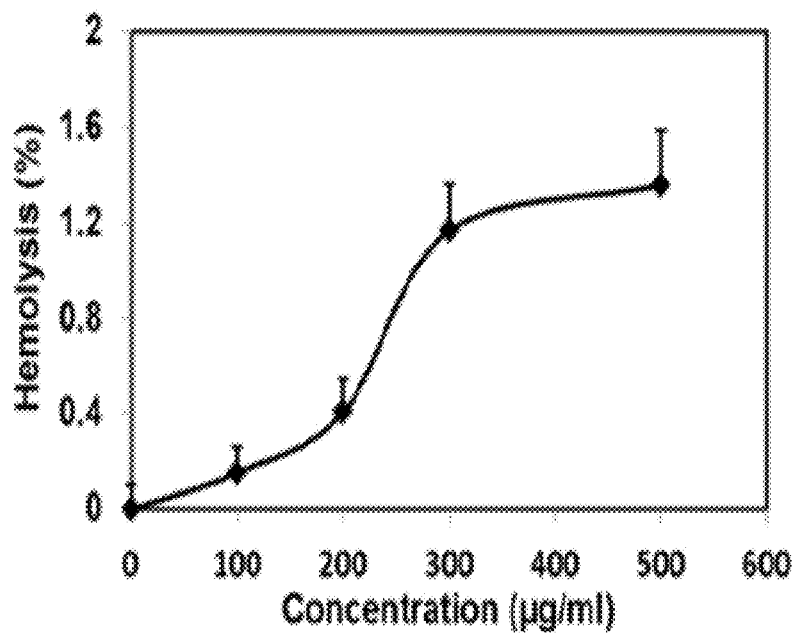
Figure 28B:
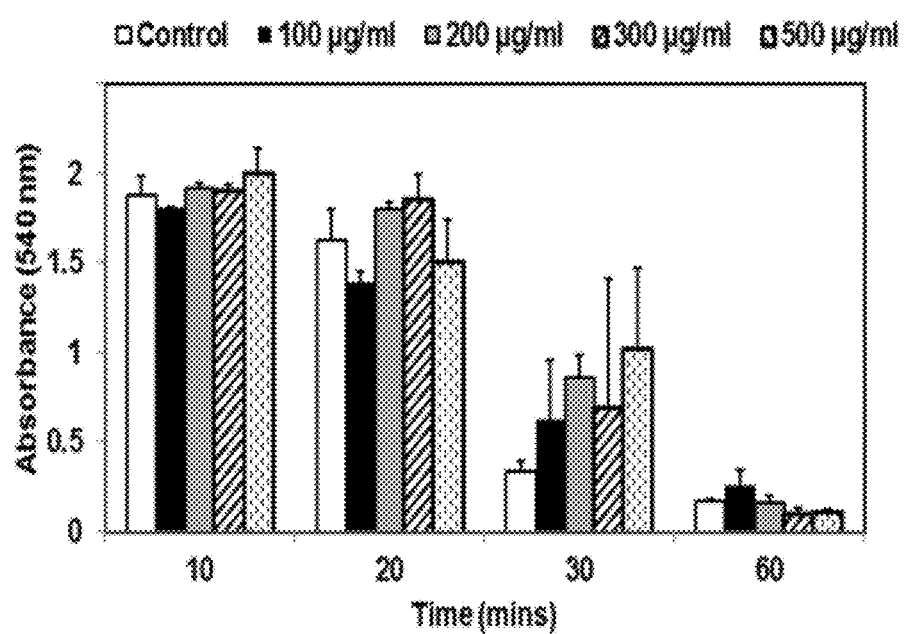

FIGS. 28A-28B graphically illustrate the results of respective hemolysis and blood clot studies for various NP concentrations according to some embodiments described herein.

FIGS. 29A-29D are magnetic resonance (MR) images of tumors according to some embodiments described herein.

Figures 29A, 29B, 29C, 29D:
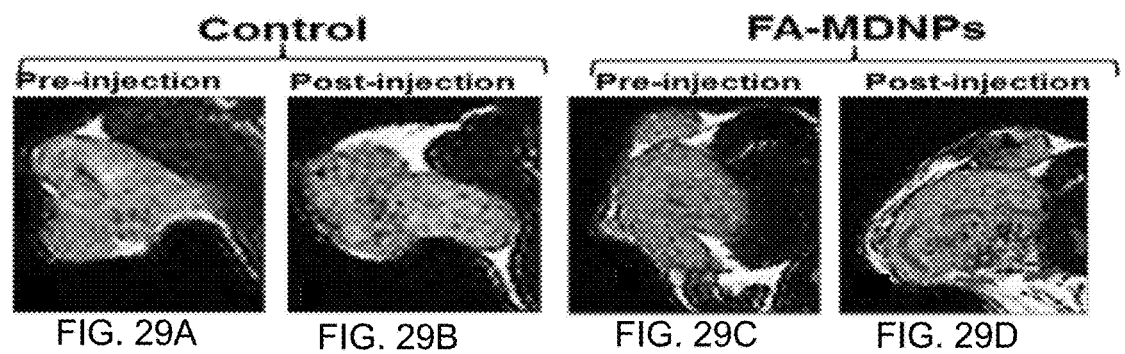
Figure 29E:
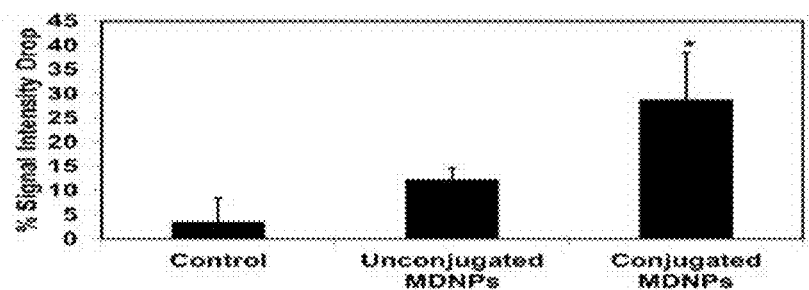

FIG. 29E graphically illustrates a T2 signal intensity drop according to some embodiments described herein.

Figure 30A:
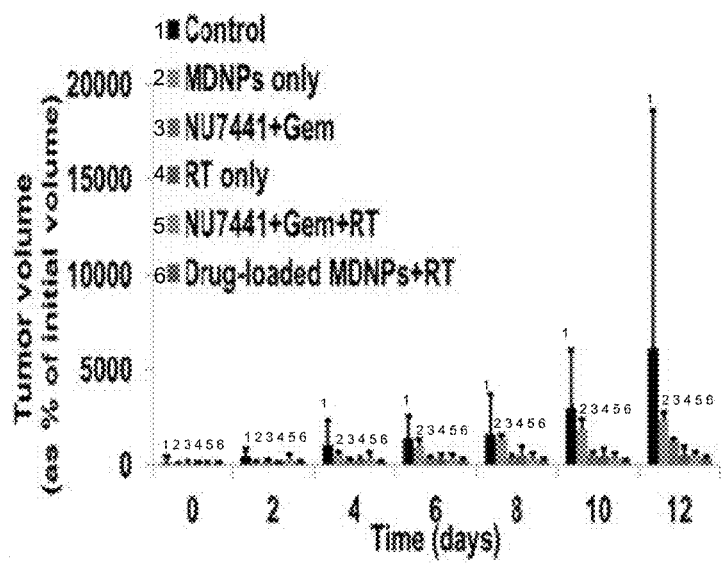
Figure 30B:
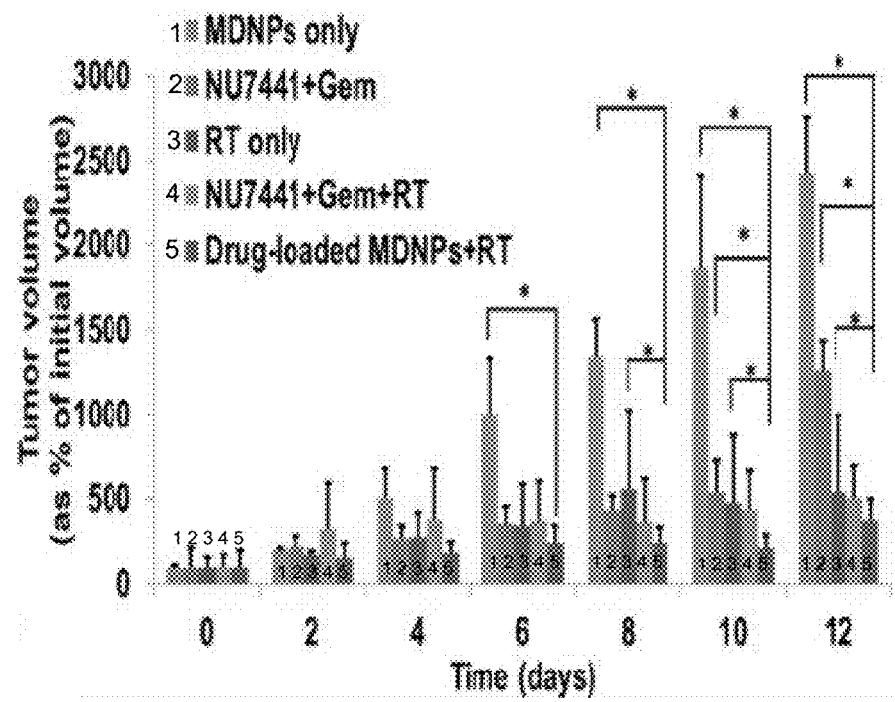
Figure 30C:
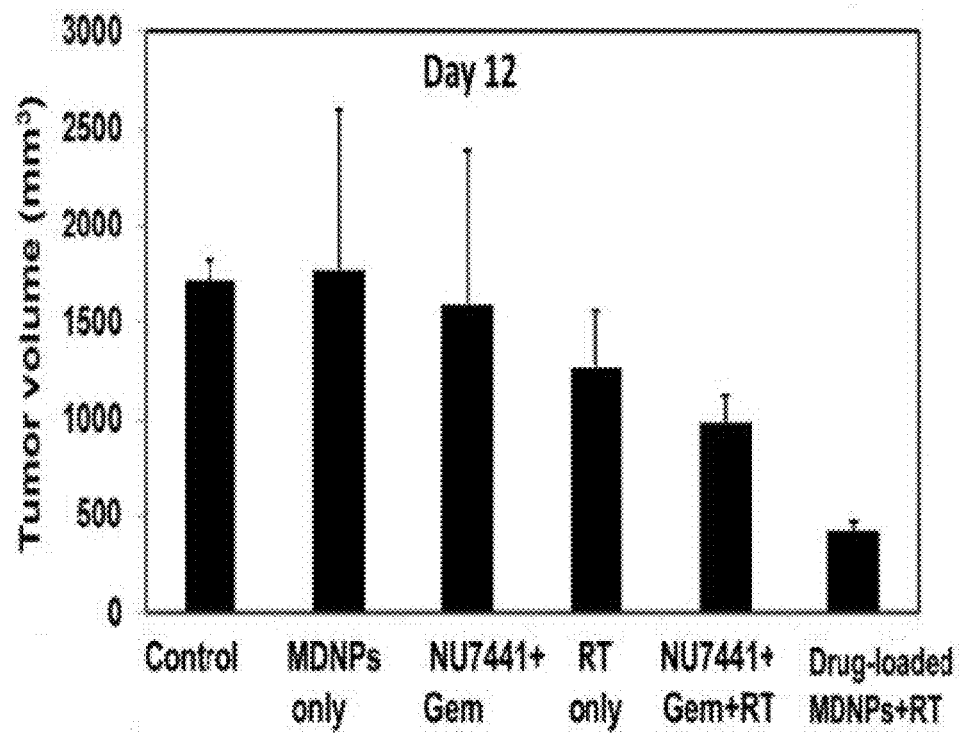

FIGS. 30A-30C graphically illustrate tumor volumes for different treatment groups according to some embodiments described herein.

Figure 31A:
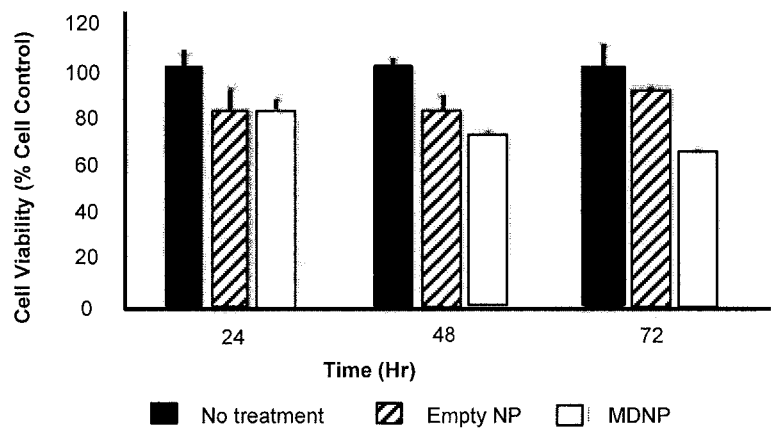
Figure 31B:
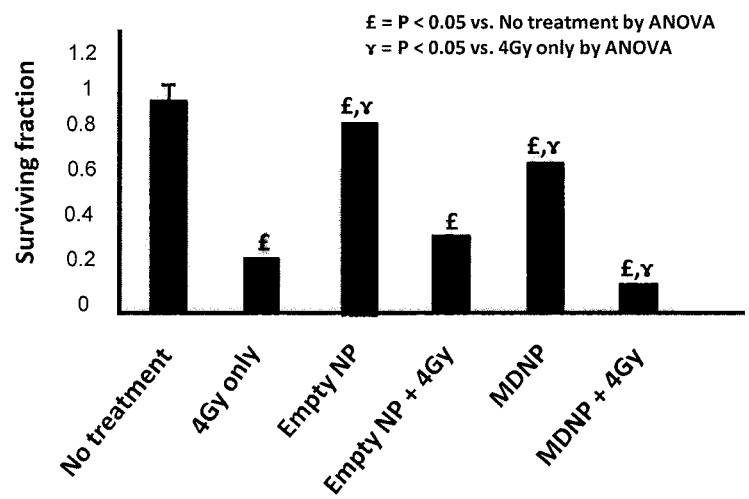
Figure 31C:
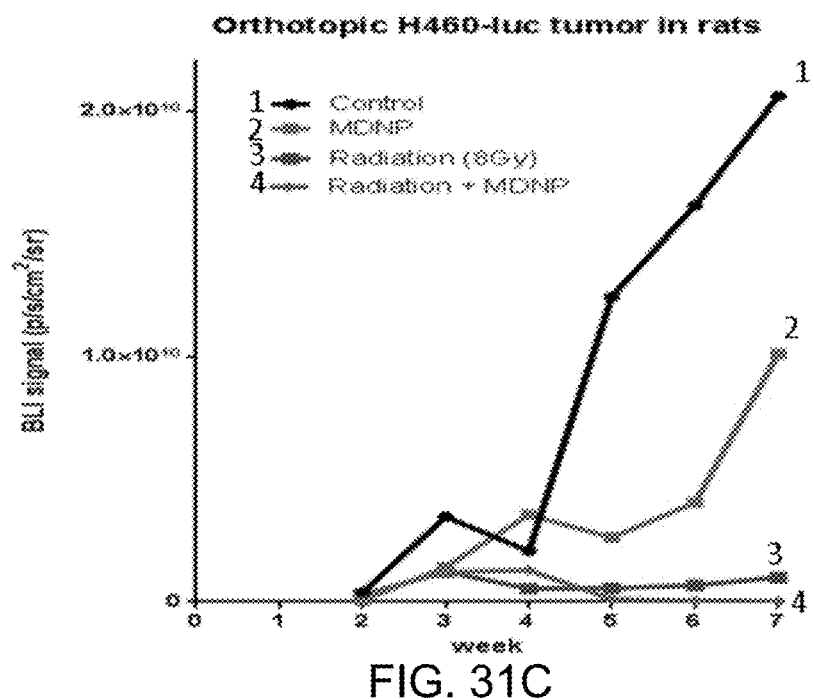

FIGS. 31A-31C graphically illustrate results from in vitro studies according to some embodiments described herein.

Figure 32A:
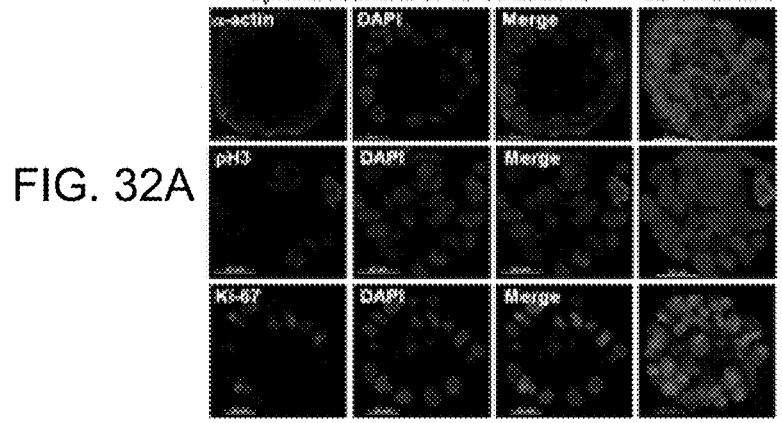
Figures 32B, 32C:
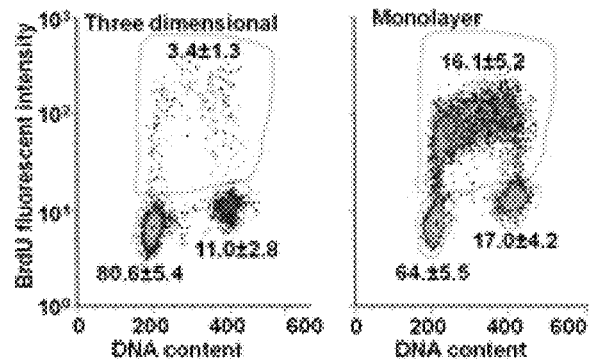

FIGS. 32A-32C graphically illustrate the effects of infrared radiation (IR) using three-dimensional (3-D) human lung models according to some embodiments described herein.

FIGS. 33A-33F graphically illustrate generation of a treatment plan according to some embodiments described herein.

DETAILED DESCRIPTION

Embodiments described herein can be understood more readily by reference to the following detailed description, examples, and figures (referred to as "FIGS."). Elements, apparatus, and methods described herein, however, are not limited to the specific embodiments presented in the detailed description, examples, and figures. It should be recognized that the exemplary embodiments herein are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should generally be considered to include the end points 5 and 10.

Further, when the phrase "up to" is used in connection with an amount or quantity; it is to be understood that the amount is at least a detectable amount or quantity. For example, a material present in an amount "up to" a specified amount can be present from a detectable amount and up to and including the specified amount.

Additionally, in any disclosed embodiment, the terms "substantially," "approximately," and "about" may be substituted with "within [a percentage] of" what is specified, where the percentage includes 0.1, 1, 5, and 10 percent.

The terms "a" and "an" are defined as "one or more" unless this disclosure explicitly requires otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition or other object that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Moreover, any embodiment of any of the compositions, systems, and methods described herein can consist of, or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

I. Compositions Comprising Core-Shell Nanoparticles

In one aspect, compositions comprising a population of core-shell nanoparticles are described herein. In some embodiments, such a composition comprises a population of core-shell nanoparticles. The core-shell nanoparticles can comprise a core component and a shell component encapsulating or surrounding the core component. Additionally, one or more radiosensitizers can be disposed in or dispersed throughout the core component, or an interior region of the core component. Similarly, one or more chemotherapeutic agents can be disposed in or dispersed throughout the shell component, or an interior region of the shell component. Moreover, in some cases, the core component can be formed from one or more biodegradable polymers. Further, in some instances, the shell component can be formed from one or more stimuli responsive polymers. In addition, in some cases, a composition described herein can further comprise a contrast agent and/or an imaging agent (i.e., a contrast/imaging agent) disposed in or dispersed throughout the core component and/or the shell component. A composition described herein may also comprise a targeting agent or ligand attached to the outer surface of the core-shell nanoparticles of the composition.

Turning now to specific components of compositions described herein, compositions described herein comprise a population of core-shell nanoparticles. As understood by one of ordinary skill in the art, "core-shell" nanoparticles include nanoparticles having a core component and a shell component, wherein the core component and the shell component are structurally distinguishable from one another, including in a non-arbitrary manner. In some cases, the core component and the shell component are formed from different materials. In other instances, the core component and the shell component differ in crystallinity and/or another discernible or measurable structural property. Moreover, the shell component of a core-shell nanoparticle described herein completely or substantially completely covers, encapsulates, surrounds, and/or "overcoats" the core component. For reference purposes herein, a shell component that "substantially" completely covers, encapsulates, surrounds, and/or overcoats a core component covers, encapsulates, surrounds, and/or overcoats at least 85%, at least 90%, at least 95%, at least 98%, or at least 99% of the exterior surface of the core component.

The core component and the shell component of a core-shell nanoparticle described herein can be formed from any materials not inconsistent with the objectives of the present disclosure. For example, in some cases, the core component and/or the shell component of a core-shell nanoparticle is formed from a biodegradable polymer or oligomer or a combination of biodegradable polymers or oligomers. It is to be understood that the terms "polymer" and "oligomer" are used interchangeably herein, without reference to a specific number of repeating units or a specific molecular weight required before an "oligomer" is considered a "polymer." In addition, a "biodegradable" polymer, for reference purposes herein, degrades in vivo to non-toxic components which can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss.

Specifically, the mass loss is calculated by comparing the initial weight ($W_0$) of the polymer with the weight measured at a pre-determined time point ($W_t$) (such as 30 days), as shown in Equation (1):

$$\text{Mass loss (\%)} = \frac{(W_0 - W_t)}{W_0} \times 100 \quad (1)$$

Any biodegradable polymer not inconsistent with the objectives of the present disclosure may be used. For example, in some instances, a biodegradable polymer comprises a naturally occurring polymer such as a gelatin, chitosan, or alginate. In some cases, a biodegradable polymer comprises a starch, polysaccharide, cellulose or cellulose derivative, dextrin, dextran, fibrin, fibrinogen, fibronectin, collagen, elastin, laminin, glycosaminoglycan, hyalauronic acid, albumin, or polypeptide. In some embodiments, a biodegradable polymer comprises a synthetic polymer such as polylactic acid (PLA), polyglycolic acid (PGA), polylactic-co-glycolic acid (PLGA), polycaprolactone (PCL), polyglycolide, polyanhydride, polyphosphazene, polyurethane, poly (N-isopropylacrylamide) (PNIPAAm), PLGA-chitosan copolymer, PLGA-PEG (polyethylene glycol) copolymer, or poly(N-isopropylacrylamide) (PNIPAAm)-carboxymethyl chitosan (CMC) copolymer.

Additionally, in some cases, the core component and/or shell component of a core-shell nanoparticle described herein is formed from a stimuli responsive or "smart" polymer or a combination of stimuli responsive or "smart" polymers. A stimuli responsive polymer described herein is capable of undergoing a rapid and reversible phase transition in response to an external stimulus or in response to a plurality of external stimuli, such as a change in magnetic field, temperature, or pH. Further, the rapid and reversible phase transition permits the polymer to "release" one or more materials disposed within and/or dispersed throughout the polymer. In this manner, a stimuli responsive polymer can release contents of the polymer "on demand," as described, for instance, in Petros R A, DeSimone J M publication entitled, "Strategies in the design of nanoparticles for therapeutic applications", available in Nat Rev Drug Discov 2010; 9: 615-27, which is hereby incorporated by reference in its entirety.

In some cases, such "on demand" release of materials from a stimuli responsive polymer occurs at a site of interest, such as a disease site or other site of diagnostic and/or therapeutic interest. For example, a temperature-sensitive or temperature-responsive polymer can be used to deliver and release drugs, "payloads", or other "cargos" in response to induced temperature changes at a disease site. Likewise, a pH-sensitive or pH-responsive polymer could be used to deliver and release drugs, "payloads", or other "cargos" in an acidic stomach lumen or tumor microenvironment.

Any stimuli responsive polymer not inconsistent with the objectives of the present disclosure may be used to form a core-shell nanoparticle described herein. For instance, in some cases, a stimuli responsive polymer is a temperature-responsive polymer or a pH-responsive polymer. Moreover, in some embodiments, a stimuli responsive polymer is a copolymer of a first stimuli responsive polymer and a second stimuli responsive polymer, wherein the first and second stimuli responsive polymers differ. For example, in some cases, a stimuli responsive polymer described herein is a copolymer of a temperature-responsive first polymer and a pH-responsive second polymer, wherein the first and second polymers differ. One non-limiting example of a temperature-responsive polymer is poly(N-isopropylacrylamide) (PNIPAAm). Non-limiting examples of a pH-responsive polymer include a chitosan such as carboxymethyl chitosan (CMC). Thus, in some instances, a stimuli responsive polymer described herein comprises a copolymer of PNIPAAm and CMC.

Other combinations and copolymers of temperature-responsive, magnetic field-responsive, and/or pH-responsive polymers may also be used. More generally, it is further to be understood that other combinations and copolymers of first and second stimuli responsive polymers, in addition to combinations and copolymers of temperature-responsive, magnetic field-responsive, and/or pH-responsive polymers, may also be used.

Moreover, in some embodiments, a copolymer described herein defines or forms an interpenetrating or semi-interpenetrating polymer network. Such a network can be formed by interpenetrating or semi-interpenetrating first and second stimuli responsive polymers described herein.

Additionally, a stimuli responsive copolymer described herein can include any ratio of first stimuli responsive polymer to second stimuli responsive polymer not inconsistent with the objectives of the present disclosure. For example, in some cases, the ratio of first stimuli responsive polymer to second stimuli responsive polymer is between 10:1 and 1:10, between 5:1 and 1:5, between 3:1 and 1:3, between 2:1 and 1:2, or between 1.5:1 and 1:1.5, based on the weights of the first stimuli responsive polymer and the second stimuli responsive polymer.

Moreover, in some instances, the ratio of first stimuli responsive polymer to second stimuli responsive polymer is selected based on a desired release profile of one or more agents disposed within the core component and/or shell component of the core-shell nanoparticles. For example, in some embodiments, a temperature responsive polymer is provided in a relatively high amount to provide a burst release of an agent (such as a chemotherapeutic agent) disposed within the temperature responsive polymer.

Similarly, the use of a specific polymer described hereinabove, such as a specific biodegradable polymer or a specific stimuli responsive polymer, to form the core component or the shell component of a core-shell nanoparticle can be selected based on a desired release profile of the core-shell nanoparticle. In one non-limiting example, for instance, the core component of a population of core-shell nanoparticles is formed from a biodegradable polymer such as PLGA, and the shell component of the core-shell nanoparticles is formed from a temperature-responsive, magnetic field-responsive, and/or pH-responsive polymer.

Core-shell nanoparticles having such a structure, in some instances, can provide a burst release of one or more chemotherapeutic agents disposed within or dispersed throughout the shell component, as well as a sustained release of one or more radiosensitizers disposed within or dispersed throughout the core component. Further, in some cases, the population of core-shell nanoparticles of a composition described herein exhibits simultaneous release of at least a portion of the one or more radiosensitizers from the core component and at least a portion of the one or more chemotherapeutic agents from the shell component. Other release profiles are also possible.

In addition, the core component and the shell component of a core-shell nanoparticle described herein can have any dimensions or relative dimensions not inconsistent with the objectives of the present disclosure. For example, in some cases, the core component of a core-shell nanoparticle has an average size or diameter of about 240 nm or less, about 200 nm or less, or about 100 nm or less. In some embodiments, the shell component of a core-shell nanoparticle described herein has an average thickness of about 10 nm or more, 20 nm or more, 50 nm or more, or more than 100 nm.

Compositions described herein also comprise one or more radiosensitizers disposed in the core component of the core-shell nanoparticles. As understood by one of ordinary skill in the art, a radiosensitizer increases the susceptibility of one or more cancer cells to radiation therapy. That is, radiosensitizers are provided to enhance the killing of tumor cells during radiation while having a much less effect on normal cells. Any radiosensitizers not inconsistent with the objectives of the present disclosure may be used.

In some cases, a radiosensitizer disrupts a DNA repair pathway within a cancer cell. In other instances, a radiosensitizer reduces or inhibits hypoxia within a tumor environment. In some embodiments, a radiosensitizer comprises a fluoropyrimidine, a gemcitabine, or a platinum analog such as cisplatin. In some cases, a radiosensitizer comprises a DNA double strand break repair inhibitor, DNA protein kinase inhibitor, mitotic protein plk1 inhibitor, BAX activator, EGFR inhibitor, or combination of one or more of the foregoing. In some embodiments, a radiosensitizer comprises 8-dibenzothiophen-4-yl-2-morpholin-4-yl-chromen-4-one (NU-7441), BAM7, Gefitinib, or a combination thereof. Other radiosensitizers may also be used.

Additionally, one or more radiosensitizers can be present in the core component of core-shell nanoparticles described herein in any amount not inconsistent with the objectives of the present disclosure. In some embodiments, radiosensitizers can be present in the shell component of core-shell nanoparticles described herein in any amount not inconsistent with the objectives of the present disclosure.

Moreover, in some cases, the identity and/or amount of a radiosensitizer disposed in a core component described herein is selected to provide a desired release profile of the radiosensitizer in vivo, including in a tumor environment. For example, in some instances, one or more radiosensitizers are disposed in a core component to provide both a burst release and also a subsequent sustained release of the one or more radiosensitizers from the core component. In other cases, the amount of radiosensitizer is selected to provide only a burst release or only a sustained release of the radiosensitizer. A "burst" release of a species, such as a radiosensitizer, can include an immediate or near-immediate release of a significant amount or majority of the species upon placement of the species in a target environment (e.g., a tumor environment) or upon exposure of the species to a triggering event (e.g., radiation treatment, increased temperature, or reduced pH). For example, in some embodiments, a "burst" release comprises a release of at least 20%, at least 30%, at least 40%, at least 50%, at least 60%, at least 70%, at least 80%, or at least 90% of the species from the nanoparticle within a period of 2 days or less, 1 day or less, 12 hours or less, 6 hours or less, 4 hours or less, 2 hours or less, or 1 hour or less following placement of the species in a target environment or exposure of the species to a triggering event (such as a specific temperature or temperature change, or a specific pH or pH change). In some cases, a "burst" release comprises a release of about 20-100%, 20-90%, 20-70%, 20-60%, 20-40%, 30-100%, 30-90%, 30-80%, 30-70%, 30-60%, 30-50%, 40-100%, 40-90%, 40-80%, 50-100%, 50-90%, 50-80%, 60-100%, 60-90%, 60-80%, 70-100%, or 70-90% of the species from the nanoparticle within a time period identified above.

A "sustained" release of a species, in contrast, can occur in an amount outside of the foregoing ranges described above for a burst release, in particular in an amount that provides a slower release of the species than a burst release described herein. For example, a sustained release can comprise a release of less than 20% of a species within 2 days, and may also comprise a release of at least 70% of a species within a time period of 2-4 weeks. The amount of a radiosensitizer disposed in a core-shell nanoparticle described herein can also be selected with reference to an amount of chemotherapeutic agent disposed in the core-shell nanoparticle. For instance, in some cases, the amounts of radiosensitizer and chemotherapeutic agent are selected to provide a synergistic effect, as described further herein.

Compositions described herein can further comprise one or more chemotherapeutic agents disposed in the shell component of the core-shell nanoparticles. As understood by one of ordinary skill in the art, a chemotherapeutic agent is capable of killing cancer cells without the use of radiation. Any chemotherapeutic agent not inconsistent with the objectives of the present disclosure may be used and/or provided in nanoparticles described herein.

In some cases, a chemotherapeutic agent comprises an alkylating agent such as a tetrazine or aziridine, an antimetabolite such as a fluorpyrimidine, an anti-microtubule agent such as paclitaxel, a topoisomerase inhibitor such as irinotecan, a cytotoxic antibiotic such as mitomycin, or a combination of one or more of the foregoing. In some embodiments, the shell or core component of a core-shell nanoparticle described herein comprises one or more of gemcitabin hydrochloride, suberoylanilide hydroxamic acid (SAHA, histone deacetylase inhibitor), cisplatin, 5-FU, curcumin, docetaxel, and paclitaxel. Other chemotherapeutic agents may also be used. Additionally, one or more chemotherapeutic agents can be present in the core or shell component of core-shell nanoparticles described herein in any amount not inconsistent with the objectives of the present disclosure.

Moreover, in some cases, the identity and/or amount of a chemotherapeutic agent disposed in a core component described herein is selected to provide a desired release profile of the chemotherapeutic agent in vivo, including in a tumor environment. For example, in some instances, one or more chemotherapeutic agents are disposed in a core component to provide both a burst release and also a subsequent sustained release of the one or more chemotherapeutic agents from the core component. In other cases, the amount of chemotherapeutic agent is selected to provide only a burst release or only a sustained release of the chemotherapeutic agent. The amount of a chemotherapeutic agent disposed in a core-shell nanoparticle described herein can also be selected with reference to an amount of radiosensitizer disposed in the core-shell nanoparticle. For instance, in some cases, the amounts of radiosensitizer and chemotherapeutic agent are selected to provide a synergistic effect, as described further herein.

Compositions described herein, in some embodiments, may also comprise a contrast agent disposed in or dispersed throughout the core component and/or the shell component. A contrast agent, in some cases, comprises a computed tomography (CT) contrast agent such as a radiocontrast agent or iodinated contrast agent. In some instances, a contrast agent comprises a magnetic resonance imaging (MRI) contrast agent, such as a positive magnetic resonance (T1) contrast agent. In some embodiments, such a positive contrast agent includes a chemical species comprising gadolinium or another lanthanide, such as gadolinium chloride. Moreover, a contrast agent suitable for use in some embodiments described herein can be a molecular contrast agent or a particulate contrast agent. A contrast agent may also be a nanoparticulate material. In some cases, a contrast agent comprises superparamagnetic iron oxide (SPIO) such as Feraheme or Ferumoxytol, gold manganese, or gadolinium. Other contrast agents may also be used.

Where used, the contrast agent can be present in the core component and/or the shell component of core-shell nanoparticles described herein in any amount not inconsistent with the objectives of the present disclosure.

Compositions described herein, in some embodiments, may also comprise an imaging agent disposed in or dispersed throughout the core component and/or the shell component. An imaging agent, in some cases, comprises a luminescent species, such as a fluorescent species or phosphorescent species. In some instances, an imaging agent comprises an organic fluorophore or dye such as a rhodamine, coumarin, or cyanine (such as NIR-797). In some embodiments, an imaging agent comprises a luminescent biomolecule such as green fluorescent protein (GFP) or plasmid DNA vector encoding yellow fluorescent protein (pEYFP-N1). An imaging agent may also comprise an organic fluorophore or dye conjugated to a biomolecule, such as rhodamine conjugated bovine serum albumin (BSA-rhodamine). In still other cases, an imaging agent comprises an inorganic material such as a semiconductor nanocrystal or quantum dot, which may include a Group II-VI semiconductor nanocrystal (such as CdSe) or a Group III-V semiconductor nanocrystal (such as InP or InAs).

Moreover, an imaging agent described herein can emit light having any wavelength or luminescence profile not inconsistent with the objectives of the present disclosure. For instance, in some embodiments, an imaging agent emits light having a wavelength centered in the near-infrared region of the electromagnetic spectrum. An imaging agent may also emit light having a wavelength centered in the visible region or the non-near-infrared region of the electromagnetic spectrum. In some cases, for example, an imaging agent described herein has an emission profile centered at a wavelength between 400 nm and 700 nm, between 500 nm and 650 nm, between 600 nm and 900 nm, between 700 nm and 900 nm, between 750 nm and 850 nm, between 800 nm and 1100 nm, between 1100 nm and 1400 nm.

Where used, an imaging agent can be present in the core component and/or the shell component of core-shell nanoparticles described herein in any amount not inconsistent with the objectives of the present disclosure.

A composition described herein may also comprise a targeting agent or ligand attached to the outer surface of the core-shell nanoparticles of the composition. Such a targeting agent can be operable to selectively bond to or have an affinity for a receptor or other species at a target site of interest, such as a disease site or diseased tissue. For instance, in some cases, the targeting agent selectively bonds, adheres, or couples to a cancer cell or a tumor. Any targeting agent not inconsistent with the objectives of the present disclosure may be used.

In some embodiments, the targeting agent comprises a protein (including a naturally occurring protein or an engineered protein), antibody, antibody fragment, peptide, or small organic molecule. In some cases, the targeting agent comprises a minibody, diabody, triabody, tetrabody, aptamer, affibody, or peptoid. Specific non-limiting examples of targeting agents useful in some embodiments described herein include streptavidin, biotin, and folic acid. As described further hereinbelow, folic acid can be used, in some embodiments, to actively target folate receptor-α, which is known to be overexpressed in a number of human tumor cells including lung cancer cells. A target agent can be present on a surface of a core-shell nanoparticle in any amount not inconsistent with the objectives of the present disclosure.

Moreover, in some instances, a population of core-shell nanoparticles described herein has an average particle size or diameter of about 400 nm or less, 300 nm or less, 250 nm or less, or 200 nm or less. In some cases, the population of core-shell nanoparticles has an average particle size or diameter of 40-400 nm, 50-300 nm, 50-250 nm, 50-200 nm, 100-400 nm, 100-300 nm, or 100-250 nm.

Additionally, the population of core-shell nanoparticles can be dispersed in the composition, including in a non-aggregated or substantially non-aggregated manner. For instance, at least 80%, at least 90%, or at least 95% of the nanoparticles, by mass, can be in a dispersed or non-aggregated state in the composition, including when the composition is an aqueous composition.

The population of core-shell nanoparticles may also have a negative zeta potential, including a large negative zeta potential. For instance, in some embodiments, the negative zeta potential has an absolute value of at least 10 mV. A population of core-shell nanoparticles having such a size distribution and surface charge, in some embodiments, can be stable in vivo for clinically significant periods of time and may also exhibit a biodistribution profile that promotes therapeutic efficacy of the nanoparticles and/or reduces toxicity or undesired side effects of the nanoparticles.

Further, core-shell nanoparticles described herein can be present in a composition in any amount not inconsistent with the objectives of the present disclosure. In some cases, a composition consists or consists essentially of the core-shell nanoparticles. In other instances, a composition comprises up to about 95 weight percent, up to about 90 weight percent, up to about 80 weight percent, up to about 70 weight percent, up to about 60 weight percent, up to about 50 weight percent, up to about 40 weight percent, or up to about 30 weight percent core-shell nanoparticles, based on the total weight of the composition.

In some instances, a composition described herein comprises between about 10 weight percent and about 99 weight percent, between about 10 weight percent and about 90 weight percent, between about 10 weight percent and about 80 weight percent, between about 20 weight percent and about 70 weight percent, between about 30 weight percent and about 70 weight percent, between about 30 weight percent and about 60 weight percent, between about 50 weight percent and about 99 weight percent, between about 50 weight percent and about 80 weight percent, or between about 60 weight percent and about 90 weight percent core-shell nanoparticles, based on the total weight of the composition. Further, in some embodiments, the balance of a composition described herein can be water or an aqueous solution, including a buffer solution or a pharmaceutical composition for intravenous or inhalation delivery to a patient.

Core-shell nanoparticles as described herein are used as nanocarriers for carrying and/or delivering (e.g., via the core component or shell component) any one or more species not limited to radiosensitizers described herein, chemotherapeutic agents described herein, contrast agents described herein, imaging agents described herein, and/or targeting agents described herein.

Moreover, it is to be understood that a composition described herein can comprise any combination of features described hereinabove not inconsistent with the objectives of the present disclosure. For example, in some cases, a composition comprises core-shell nanoparticles comprising any combination of core component properties described herein, shell component properties described herein, radiosensitizer properties described herein, chemotherapeutic agent properties described herein, contrast agent properties described herein, imaging agent properties described herein, and/or targeting agent properties described herein.

II. Methods of Diagnosing and/or Treating a Cancer

In another aspect, methods of diagnosing and/or treating cancer are described herein. Such a method, in some embodiments, comprises administering to a patient in need thereof a composition described hereinabove in Section I. Any composition described hereinabove in Section I may be used. For example, in some cases, the composition comprises a population of core-shell nanoparticles, wherein the core-shell nanoparticles comprise a core component; a shell component encapsulating the core component; one or more radiosensitizers disposed in the core component; and one or more chemotherapeutic agents disposed in the shell component. Further, in some embodiments, the core component and/or the shell component is formed from one or more biodegradable polymers, and the shell component is formed from one or more stimuli responsive polymers.

In some cases, a method described herein further comprises administering radiation therapy to the patient following administration of the composition to the patient. A method described herein can also comprise imaging the core-shell nanoparticles (or a portion of the patient in which the core-shell nanoparticles are disposed) following administration of a composition described herein to the patient. Such imaging can occur before, during, or after administrating radiation therapy to the patient. In this manner, a method described herein can be used both to diagnose and to treat cancer in a patient, including in a simultaneous or sequential manner.

Turning now to specific steps of methods described herein, a method of diagnosing and/or treating cancer described herein comprises administering a composition to a patient. The composition can be administered to the patient in any manner and in any amount not inconsistent with the objectives of the present disclosure. For example, in some cases, the composition is administered to the patient as an aerosol, liquid, or powder. In some embodiments, the composition is administered to the patient intravenously (e.g., in the case of a liquid composition) or using an inhaler (e.g., in the case of an aerosol composition).

Moreover, in some cases, a method described herein further comprises administering radiation therapy to a patient. Radiation therapy can be administered to the patient in any manner not inconsistent with the objectives of the present disclosure. In some embodiments, the radiation therapy comprises external beam radiation therapy (EBRT), brachytherapy ("sealed source"), or systemic radioisotope ("unsealed source") therapy. Further, the radiation therapy can comprise photon therapy or particle therapy. Additionally, in some cases, administering radiation therapy to the patient comprises exposing the core-shell nanoparticles (or a region of the patient in which the core-shell nanoparticles are disposed) of the composition described herein to a radiation source or beam of radiation, including a radiation source or beam of radiation associated with a method of radiation therapy identified above.

A method described herein can also comprise imaging the core-shell nanoparticles (or a portion of the patient in which the core-shell nanoparticles are disposed). Such imaging can be carried out in any manner not inconsistent with the objectives of the present disclosure. For example, in some cases, imaging comprises carrying out MRI imaging and/or CT imaging. Further, in some such instances, carrying out MRI imaging and/or CT imaging comprises detecting one or more contrast agents disposed in the core-shell nanoparticles of the composition. In other embodiments, imaging comprises carrying out luminescence imaging. In some such cases, carrying out luminescence imaging comprises exposing the patient or a portion of the patient to electromagnetic radiation having a wavelength corresponding to an excitation wavelength of a luminescent imaging agent disposed in the core-shell nanoparticles, and detecting photoluminescence emitted by the imaging agent in response to the foregoing exposure to excitation radiation. Imaging steps such as those described above can be carried out using any imaging system not inconsistent with the objectives of the present disclosure, including an imaging system known to one of ordinary skill in the art.

Moreover, the cancer that is diagnosed and/or treated by a method described herein can comprise any cancer not inconsistent with the objectives of the present disclosure. In some cases, the cancer is lung cancer, such as Small Cell Lung Cancer (SCLC) or Non-Small Cell Lung Cancer (NSCLC). The cancer can also comprise a non-metastatic, stage IIA-B lung cancer. In some instances, the cancer is gastrointestinal cancer, colon cancer, skin cancer, melanoma, brain cancer, prostate cancer, testicular cancer, ovarian cancer, liver cancer, leukemia, glioblastoma, head and neck cancer, bladder cancer, myeloma, or pancreatic cancer. Other types of cancer may also be treated according to a method described herein.

Further, it is to be understood that a method described herein can include any combination of features or steps described hereinabove not inconsistent with the objectives of the present disclosure.

III. Methods of Making a Core-Shell Nanoparticle

In another aspect, methods of making a core-shell nanoparticle are described herein. The core-shell nanoparticle can comprise any core-shell nanoparticle described hereinabove in Section I. In some embodiments, such a method comprises providing a core component; disposing one or more radiosensitizers within an interior region of the core component; forming a shell component over the core component; and disposing one or more chemotherapeutic agents with an interior region of the shell component. A method described herein can also comprise disposing a contrast agent within the interior region of the core component and/or within the interior region of the shell component. Additionally, in some instances, a method described herein further comprises disposing an imaging agent within the interior region of the core component and/or within the interior region of the shell component. In some cases, a method described herein also comprises attaching a targeting agent to the outer surface of the core-shell nanoparticle.

Turning now to specific steps of methods described herein, a method of making a core-shell nanoparticle described herein comprises providing a core component. The core component can be provided or synthesized in any manner not inconsistent with the objectives of the present disclosure. Further, the core component can be any core component described hereinabove in Section I. For example, in some cases, the core component is provided by emulsion, two-step desolvation, ionic gelation, cation-induced controlled gelification, emulsion-solvent evaporation, and cross-linking. In some embodiments, the core component is provided by emulsion, including an emulsion method described further hereinbelow.

A method described herein also comprises disposing one or more radiosensitizers within an interior region of the core component. Radiosensitizers can be disposed within an interior region of the core component in any manner not inconsistent with the objectives of the present disclosure. Further, the radiosensitizers can comprise any radiosensitizers described hereinabove in Section I. In some instances, one or more radiosensitizers are disposed within an interior region of the core component by synthesizing the core component in a manner described herein in the presence of the one or more radiosensitizers.

In addition, a method described herein further comprises forming a shell component over the core component. The shell component can be formed in any manner not inconsistent with the objectives of the present disclosure. Additionally, the shell component can comprise any shell component described hereinabove in Section I. In some embodiments, the shell component is formed over the core component by emulsion, two-step desolvation, ionic gelation, cation-induced controlled gelification, emulsion-solvent evaporation, and cross-linking, including in the present of the previously formed core component. In some embodiments, the shell component is provided by emulsion, including a cross-linking method described further hereinbelow.

A method described herein can also comprise disposing one or more chemotherapeutic agents with an interior region of the shell component. Chemotherapeutic agents can be disposed within an interior region of the shell component in any manner not inconsistent with the objectives of the present disclosure. Further, the chemotherapeutic agents can comprise any chemotherapeutic agents described hereinabove in Section I. In some instances, one or more chemotherapeutic agents are disposed within an interior region of the shell component by synthesizing the shell component in a manner described herein in the presence of the one or more chemotherapeutic agents.

Moreover, in some cases, a method described herein further comprises disposing a contrast agent and/or an imaging within the interior region of the core component and/or within the interior region of the shell component. A contrast agent and/or an imaging agent can be disposed within an interior region of the core component and/or within the interior region of the shell component in any manner not inconsistent with the objectives of the present disclosure. In addition, the contrast agent and/or imaging agent can comprise any contrast agent and/or imaging agent, respectively, described hereinabove in Section I. In some instances, a contrast agent and/or an imaging agent is disposed within the interior region of the core component and/or within the interior region of the shell component by synthesizing the core component and/or shell component in a manner described herein in the presence of the contrast agent and/or imaging agent.

A method described herein, in some embodiments, further comprises attaching a targeting agent to the outer surface of the core-shell nanoparticle. The targeting agent can be attached to the outer surface of the core-shell nanoparticle in any manner not inconsistent with the objectives of the present disclosure. Moreover, the targeting agent can comprise any targeting agent described hereinabove in Section I. In some cases, the targeting agent is attached to the outer surface of the core-shell nanoparticle by a carbodiimide coupling scheme, a biotin-streptavidin or biotin-avidin coupling scheme, or any other method not inconsistent with the instant disclosure.

Some embodiments described herein are further illustrated in the following non-limiting examples.

Unless otherwise noted herein, chemicals described in the following Examples are available from Sigma-Aldrich, located in St. Louis, Mo. Poly Lactic-co-Glycolic Acid (PLGA), having an inherent viscosity of 0.4 dL/g and a copolymer ratio of 50:50, is available from Lakeshore Biomaterials, located in Birmingham, Ala. Chitosan is available from Polyscience Inc., located in Warrington, Pa. and NH2-PEG-COOH is available from Laysan Bio Inc., located in Arab, Ala. Iron oxide nanoparticles (NPs) are available from Meliorum Technologies, located in Rochester, N.Y. Primary human alveolar Type 1 cells, Prigrow III media, and collagen-coated T25 flasks are available from Applied Biological Materials Inc., located in Richmond, BC, Canada. Fetal bovine serum (FBS), penicillin-streptomycin, and trypsin-Ethylenediaminetetraacetic acid (EDTA) are available from Atlanta Biologicals, located in Lawrenceville, Ga.

Example 1

Synthesis of Various Natural and Synthetic Polymer-Based NPs

A two-step desolvation method was employed for the synthesis of gelatin NPs. Initially, 1.25 grams (g) of Type A gelatin was dissolved in deionized (DI) water and 25 mL of acetone was added to it so that a gel-like precipitate was obtained. The precipitate was re-dissolved in water and 75 mL of acetone was added dropwise at 40° C. to obtain a milky-white solution. A glutaraldehyde crosslinker in an amount of 0.2 mL was added to the solution, and the solution was stirred overnight to allow acetone evaporation. The following day, the nanoparticle suspension was dialyzed and lyophilized to obtain gelatin NPs. An exemplary two-step desolvation method is described in the publication entitled "Layer-by-Layer-Coated Gelatin Nanoparticles as a Vehicle for Delivery of Natural Polyphenols", authored by Shutava et al., and available at ACS Nano 2009 2012/07/05; 3(7): 1877-1885, the entire contents of which is incorporated herein by reference.

Chitosan NPs were prepared by an ionic gelation method involving sodium tripolyphosphate (TPP). An amount of 10 mg of chitosan was added to 5 mL of 1% (w/v) acetic acid, and the final pH of the solution was adjusted to 5.5. Following dropwise addition of 2 mL of 1 mg/mL TPP, the solution was stirred for 1 hour to allow nanoparticle formation. Dialysis and lyophilization was then carried out to obtain the final chitosan NPs. One exemplary method of preparing chitosan NPs can be found in the publication entitled "Modulation of surface charge, particle size and morphological properties of chitosan-TPP nanoparticles intended for gene delivery", by Gan et al., available at Colloids Surf B Biointerfaces 2005 August; 44(2-3):65-73, the entire contents of which is incorporated herein by reference.

Alginate NPs were prepared by cation-induced controlled gelification. First, 9.5 mL of sodium alginate solution (0.06% w/v) was prepared and 0.5 mL of 18 mM of calcium chloride was added dropwise to it. A chitosan solution (0.05% w/v) in an amount of 2 mL was then added and the resultant solution was stirred overnight. Centrifugation at 19,000 rpm for 30 minutes followed by lyophilization was done the following day in order to obtain the NPs.

PLGA NPs were prepared by a standard emulsion-solvent evaporation method. For this procedure, 90 mg of PLGA was first dispersed in 3 mL chloroform to form an organic phase. This was then added dropwise to a polyvinyl alcohol (PVA) solution (5% w/v) and sonicated at 50 W for 3 minutes. The particle suspension was then stirred overnight at room temperature to allow solvent evaporation. NPs were recovered by ultracentrifugation at 25,000 rpm for 30 minutes at 10° C. For bovine serum albumin (BSA) loaded NPs, 30 mg of a BSA solution was mixed in 300 μl of DI water and then emulsified in the PLGA-chloroform solution. Similarly for cDNA loaded NPs, 9 mg of the cDNA was dispersed in DI water and used for emulsification with PLGA solution.

For the preparation of PLGA-chitosan (PLGA-CS) NPs, carboxymethyl chitosan (CMC) was mixed with PVA surfactant solution. The NP preparation procedure is similar to that of PLGA NPs described above, except for the addition of 0.5% (w/v) CMC in 4.5% (w/v) PVA solution.

In order to copolymerize PLGA and PEG, an N-hydroxysuccinimide (NHS) group was first introduced onto PLGA using EDC-NHS chemistry. For example, 5 g of PLGA was taken in DCM and 1-ethyl-3-(3-dimethylaminopropyl)-carbodiimide (EDC) and N-hydroxysuccinide (NHS) was added to it. Following shaking for 2 hours, the PLGA-NHS was collected by washing with ethyl acetate and methanol. An amount of 1 g of PLGA-NHS was then dissolved in 4 mL of chloroform and then 250 mg of COOH-PEG-NH2 and 28 mg N-diisopropylethylamine was added and stirred for 12 hours. The copolymer was precipitated with cold methanol and washed three times to remove unreacted PEG. The polymer was dried under vacuum and used for NP preparation by the emulsion procedure described above. BSA was used as a protein model while YFP or GFP-encoded plasmid cDNA was used as a cDNA model for encapsulation within all six NPs. All NPs were lyophilized and stored in powder form at −20° C. when not in use and were freshly reconstituted in DI water/media/saline/Gamble's solution for Examples herein.

Example 2

Characterization of Synthesized Natural and Synthetic Polymer-Based NPs

Synthesized natural and synthetic polymer-based NPs were characterized according to exemplary embodiments described herein. The NP size, charge and polydispersity were determined using a ZetaPALS dynamic light scattering (DLS) detector, such as those available from Brookhaven Instruments, located in Holtsville, N.Y. In this example, 20 μl of 1 mg/mL NP suspension was added to a transparent cuvette containing 3 mL DI water and placed in the instrument. The NP properties were detected by scattering of laser light due to Brownian motion of the NPs in solution. Transmission electron microscopy (TEM), (i.e., model no. FEI Tecnai G2 Spirit BioTWIN available from Hillsboro, Oreg.) was used to study the morphology of the NPs. A drop of particle suspension (1 mg/mL) was placed on a Formvar-coated 200-mesh copper grid available from Electron Microscopy Sciences, located in Hartfield, Pa., at room temperature and air-dried. The sample was then inserted into the TEM instrument for visualization.

Physical-Chemical Characterization

The in vitro stability of the NPs was determined by dispersing them in four different solutions, namely (i) DI water, (ii) saline (0.9% sodium chloride solution), (iii) fetal bovine serum (FBS), and/or (iv) simulated lung fluid (e.g., Gamble's solution). The NP suspensions were then incubated at 37° C. and particle sizes were measured using DLS at predetermined time points up to 5 days. In addition, drug release studies were conducted on the NP formulations. The amount of un-entrapped reagent collected in the supernatant after centrifugation was quantified to determine the drug loading efficiency of the NPs. The protein/cDNA encapsulation efficiency can be calculated as the percentage of protein/cDNA used initially during nanoparticle formulation according to Equation (2):

$$\text{Loading efficiency (\%)} = \frac{\text{Protein}/cDNA \text{ used} - \text{Protein}/cDNA \text{ in supernatant}}{\text{Protein}/cDNA \text{ used}} \quad (2)$$

For in vitro release studies, BSA was used as the protein model for encapsulation within the NPs. For example, 1 mL of a nanoparticle suspension (1 mg/mL) was added to dialysis bags with molecular weight cut-off of 100 kDa (e.g., available from Spectrum Laboratories Inc., located at Rancho Dominguez, Calif.) and dialyzed against DI water at 37° C. for 21 days. At each time point, 1 mL of dialysate was collected from the samples and replaced with 1 mL of fresh DI water. Pierce BCA protein assays (e.g., available from Fisher Scientific, located in Hampton, N.H.) were used according to the manufacturer's instructions in order to quantify the amount of protein being released.

Results:

Six NP preparations made of natural and synthetic polymers were screened to identify formulations for pulmonary delivery and uptake by distal lung cells. Results of the characterization studies indicate that most NPs, except PLGA-PEG and alginate NPs, maintained a hydrodynamic diameter about 300 nanometers (nm) or less (see e.g., Table 1, below). The larger sized alginate NPs (556±56 nm) is consistent for preparation by the ionic gelation method, with sizes in the 536 nm to 1.8 µm range for gene therapy. However, NPs in the 50 to 200 nm size range have demonstrated greater alveolar deposition. A majority of the NP formulations tested, except alginate and PLGA-PEG, were in a desirable size range (e.g., <300 nm) as nanocarriers for pulmonary delivery. The smaller polydispersity values of PLGA and PLGA-CS NPs of 0.14 and 0.07, respectively, indicate that the NPs are relatively uniformly dispersed.

Chitosan and alginate NPs on the other hand demonstrated larger polydispersity values of about 0.28 and 0.29, respectively, indicating more variation in the particle size distribution. The positive zeta potential value of chitosan NPs indicates presence of cationic $NH_2$ groups on the surface of the particle while high negative zeta potential values of the other NP formulations are indicative of good stability.

TABLE 1

Size, charge and polydispersity characterization of NP formulations

| Polymer | Particle Diameter (nm) | Polydispersity | Zeta Potential (mV) |
|---|---|---|---|
| Gelatin | 187 ± 83 | 0.22 ± 0.01 | −18.2 ± 2.6 |
| Chitosan | 253 ± 110 | 0.28 ± 0.02 | 4.8 ± 1.1 |
| Alginate | 556 ± 56 | 0.29 ± 0.01 | −28.7 ± 0.9 |
| PLGA | 160 ± 63 | 0.14 ± 0.02 | −20.2 ± 1.2 |
| PLGA-CS | 191 ± 60 | 0.07 ± 0.01 | −17.2 ± 1.3 |
| PLGA-PEG | 335 ± 131 | 0.22 ± 0.03 | −25.4 ± 1.0 |

FIGS. 1A-1F are Transmission Electron Microscopy (TEM) images of NPs prepared using Gelatin, Chitosan, Alginate, PLGA, PLGA-CS, and PLGA-PEG, respectively. The insets in FIGS. 1A-1F are TEM images illustrating the morphology of a single nanoparticle from each formulation.

TEM images indicate the morphology and distribution of nanoparticles in each nanoparticle formulation. It can be observed that all particles are relatively spherical in morphology and uniformly dispersed (see e.g., FIGS. 1A-F). In addition, the particle sizes in the images are in accordance with the size ranges observed using the dynamic light scattering (DLS) instrument.

FIGS. 2A-2D depict stability of NPs formulations in solutions. Stability can be tested by measuring particle size in DI water, 10% FBS, saline solution, and simulated lung fluid respectively at 37° C. The PLGA-based and gelatin NPs remained stable for up to 5 days, while alginate NPs tended to show aggregation by around fourth day. Chitosan NPs showed fluctuations in size indicating comparatively less stability (e.g., around n=4).

Stability studies of NPs indicated that PLGA NPs were relatively stable in all four solutions over five days with no significant aggregation or particle size change. Gelatin NPs were also stable in all solutions, and consistent with particles prepared by a layer-by-layer method that demonstrated stability up to four weeks after preparation. Alginate NPs also showed significant aggregation in serum, saline, and simulated lung fluid as demonstrated by previous studies where alginate-chitosan NPs tended to break apart at a pH of 7.0 due to their instability at physiological pH. PLGA-CS NPs remained relatively stable in DI water, serum, and simulated lung fluid although some aggregation was observed in saline solution possibly due to chitosan's thermodynamic instability with pH changes.

Figure 2C:
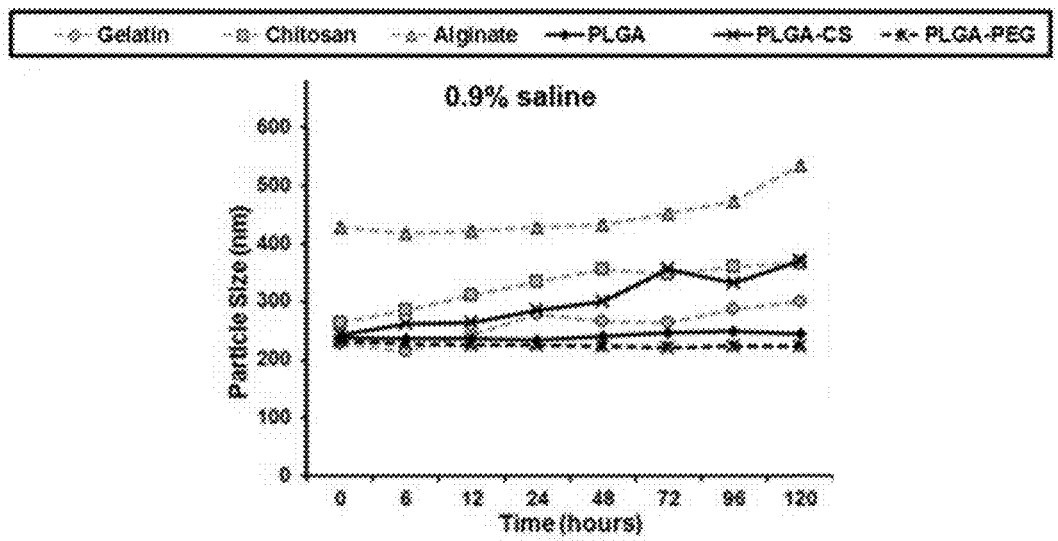
Figure 2D:
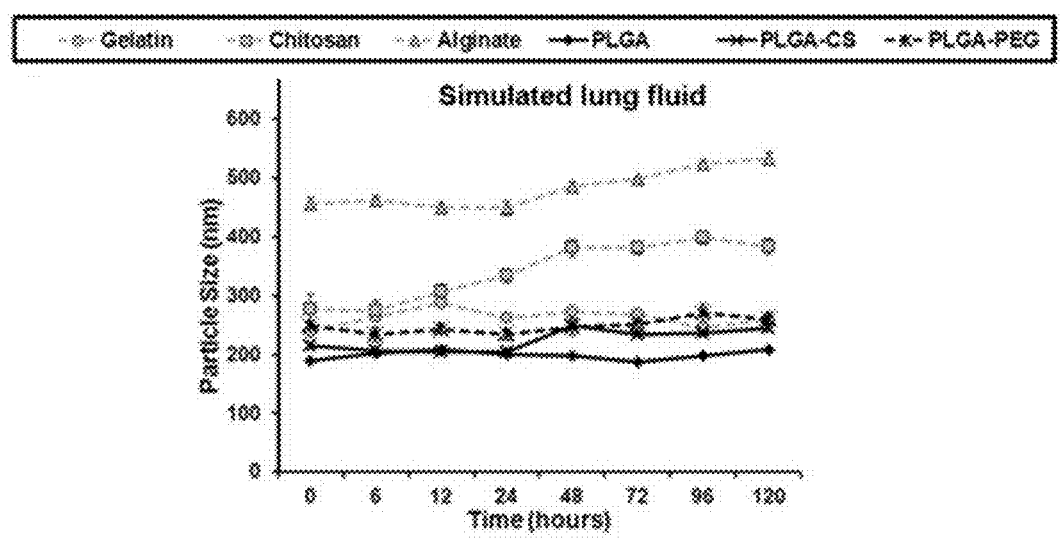
Figure 3A:
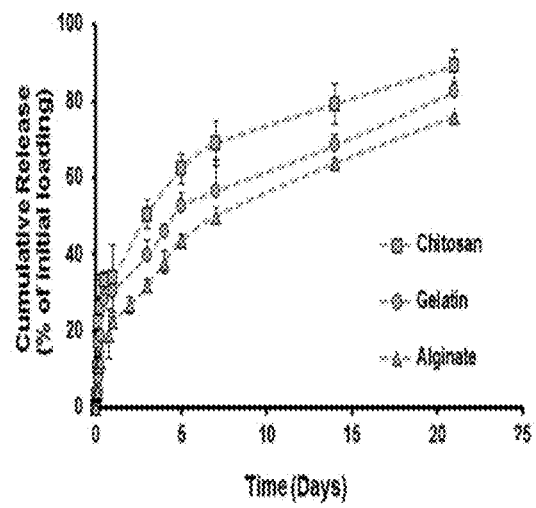
FIGS. 3A-3B graphically illustrate drug release profiles associated with NPs according to some embodiments described herein.
Figure 3B:
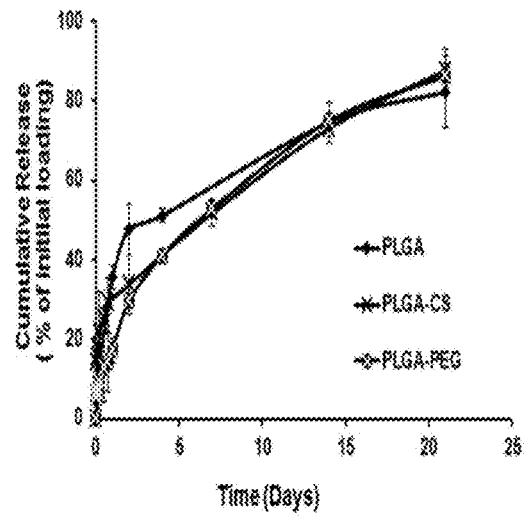

FIGS. 3A-3B illustrate the bi-phasic drug release profile of all NPs indicating a burst release of one or more species for the first two days followed by sustained release of one or more species over three weeks. Gelatin, chitosan, and PLGANPs showed an initial burst release of more than about 40% of the loaded drug within four days (e.g., n=4).

Further, drug release studies indicate that more than about 80% of incorporated BSA is released from all particles in a biphasic manner within three weeks. Among natural polymer-based NPs, gelatin demonstrated a burst release of about 32% of the drug in two days while chitosan and alginate NPs showed burst release of 43% and 27% of the drug, respectively, within the same time period. The high burst release (e.g., about 43%) from chitosan NPs as seen in FIG. 3A within two days is consistent with NPs prepared with medium molecular weight chitosan.

As seen in FIG. 3B, the highest burst release among all synthetic NPs was observed for PLGA NPs (about 48%) within two days followed by a characteristic sustained release up to 21 days. A higher burst release was observed from PLGA than from PLGA-PEG NPs (about 30%). This may have occurred due to the different PEG compounds used in their experiments and the availability of different functional groups on the NPs that may interact different with different encapsulated compounds.

Example 3

In Vitro Characterization of Synthesized Natural and Synthetic Polymer-Based NPs Human lung cells, namely, alveolar Type 1 epithelial cells (AT1), were seeded in 96-well tissue culture plates at a density of 16,000 cells/cm$^2$ and incubated at 37° C. and 5% $CO_2$ overnight for cell attachment. The following day, media in each well was aspirated and replaced with increasing concentration (i.e., 0, 100, 200, 300, 500, 1000, 2000 µg/ml) of NP suspensions in media for 24 hours.

The cells were then washed twice with 1× Phosphate buffered saline (PBS) and incubated with MTS reagent (e.g., CellTiter 96® AQueous One Solution Cell Proliferation Assay, available from Promega, located in Madison, Wis.) in media. Absorbance readings were taken at a wavelength of 490 nm using a UV-Vis spectrometer (e.g., an Infinite M200 plate reader, available from Tecan, located in Durham, N.C.), to determine cell viability. In order to confirm the MTS assay results, a Picogreen dsDNA assay was also performed to determine the DNA content per sample. For this assay, the cells were first lysed using 1% Triton X-100 and then the assay was conducted on the cell lysates per manufacturer's instructions.

For the cellular uptake study, AT1 cells were seeded in tissue culture plates and incubated as described above. Then the cells were incubated with increasing concentrations (i.e., 0, 100, 200, 300, 500 µg/ml) of ICG-loaded NPs suspended in media for 2 h. Following incubation, the cells were washed 3 times with PBS and lysed using 1% Triton X-100.

Fluorescence intensity measurements of each sample was carried out using a spectrophotometer at excitation of 780 nm and emission of 810 nm to determine the amount of ICG-loaded particles taken up by the cells. The measurements were analyzed against nanoparticle standards. The particle uptake was then normalized with the total DNA content per sample using Picogreen dsDNA assays (e.g., available from Invitrogen, located in Grand Island, N.Y.) at excitation of 480 nm and emission of 520 nm. The cell lysate sample may be quantified for the total cell protein or DNA, which presents the cell number per sample, using protein or DNA assays. However, EPO- and cDNA-loaded NPs may interfere with the readings for both these assays. Therefore, ICG-loaded particles were used for this study since the fluorescence readings will not interfere with quantification of the total cell protein/DNA in the cell lysate samples.

A cell activation study was conducted to determine whether NP uptake causes oxidative stress in the cells in vitro. For example, human AT1 cells were seeded in tissue culture plates and incubated overnight as described earlier. The next day, cells were exposed to two different concentrations of each NP (250 µg/ml and 1000 µg/ml) and incubated for another 24 hours. Cells exposed to 10 µg/ml lipopolysaccharide (LPS) were considered as a positive control while cells exposed to media only served as the negative control. To detect the Intracellular Reactive Oxygen Species (ROS) production on NP exposure, cells were then washed thrice with PBS and incubated with 5 µM of 2′,7′-dichlorodihydrofluorescein diacetate ($H_2DCFDA$) solution in PBS for 30 minutes. The cells were then washed again with PBS and fluorescence was measured at $\lambda_{ex}$ of 485 nm and $\lambda_{ex}$ of 530 nm using a spectrophotometer.

Results:

The cytocompatibility with AT1 cells observed for gelatin NPs is about 80% viability at 2 mg/mL. Chitosan NPs maintained greater than 80% cytocompatibility up to a concentration of 1 mg/mL. Similarly, alginate NPs showed a cell viability of about 92% cell viability at 250 µg/ml concentration. The results indicate that all NP formulations are compatible with lung cells up to a high concentration of about 1 mg/mL.

Figure 4A:
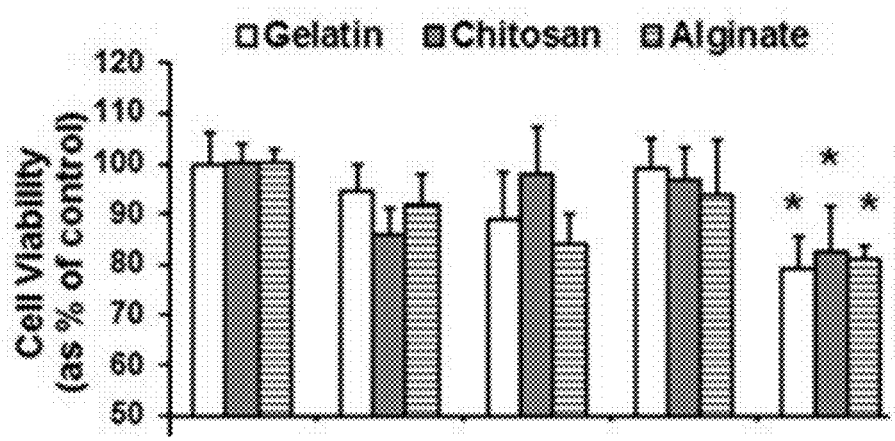
FIGS. 4A-4D graphically illustrate the results of cell viability studies conducted on NPs according to some embodiments described herein.
Figure 4B:
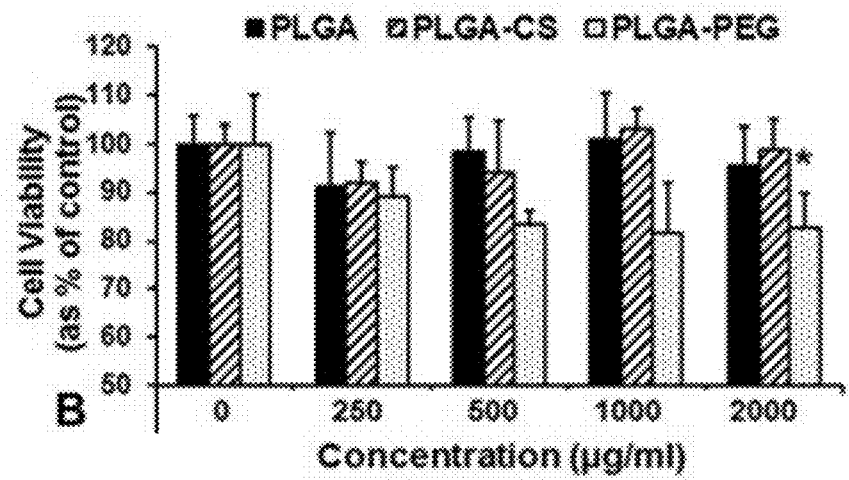
Figure 4C:
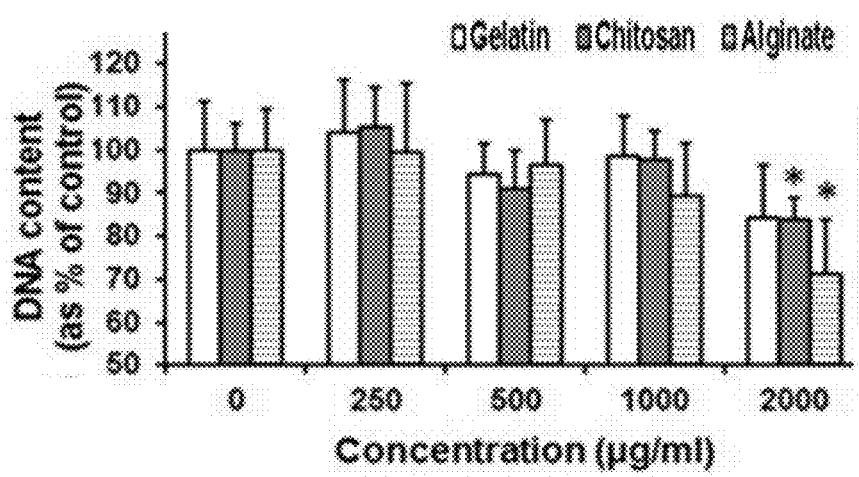
Figure 4D:
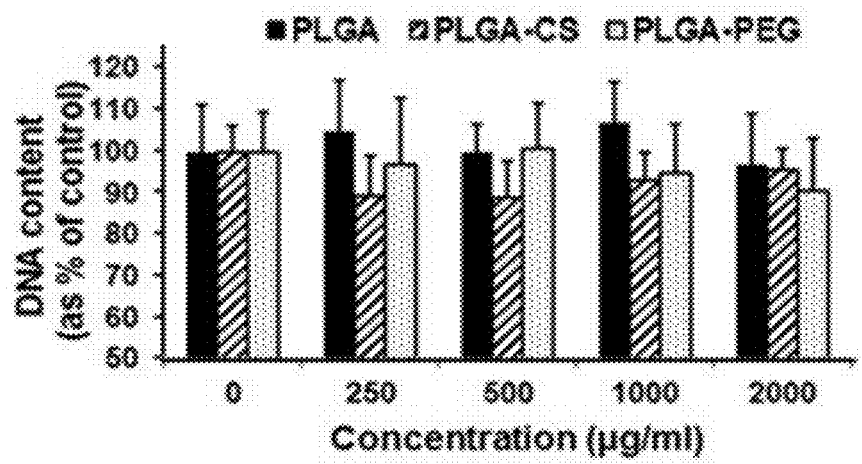

FIGS. 4A-B depict cell viability studies on AT1 epithelial cells using MTS assay and FIGS. 4C-D depict the DNA content of a Picogreen ds DNA assay and indicate that gelatin, chitosan, alginate and PLGA-PEG NPs maintained cytocompatibility up to a concentration of 1000 µg/ml. All NPs except alginate showed greater than 80% DNA content at 2000 µg/ml concentration (e.g., n=3, *$p<0.05$ w.r.t cell viability at 0 µg/ml MDNP concentration).

These findings were confirmed using Picogreen dsDNA assays. As FIG. 4D illustrates, more than 90% of the total cell DNA was retained following incubation with PLGA-based NPs at all concentrations. About 80% of control DNA content was obtained following treatment with gelatin and chitosan NPs up to 2 mg/mL concentration as indicated in FIG. 4C. Incubation with alginate NPs resulted in a decrease in DNA content to 76% at 2 mg/mL concentration. It should be noted, however, that more than 80% of the DNA content was observed in all samples following incubation with all particles up to 1 mg/mL concentration indicating that these particles are cytocompatible up to 1 mg/mL. This indicates that all the NP formulations are cytocompatible at high concentrations with AT1 cells in vitro.

Figure 5A:
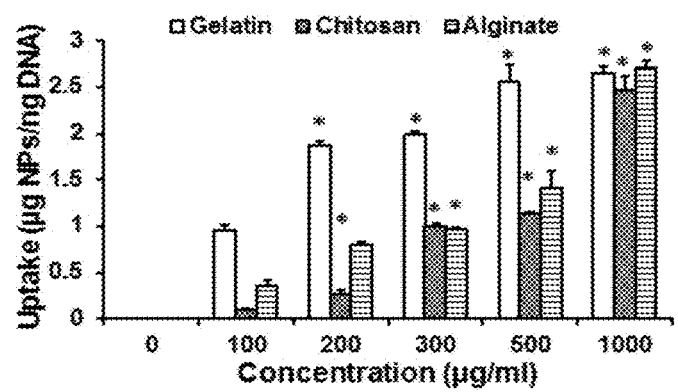
FIGS. 5A-5B graphically illustrate the cellular uptake of NP formulations according to some embodiments described herein.
Figure 5B:
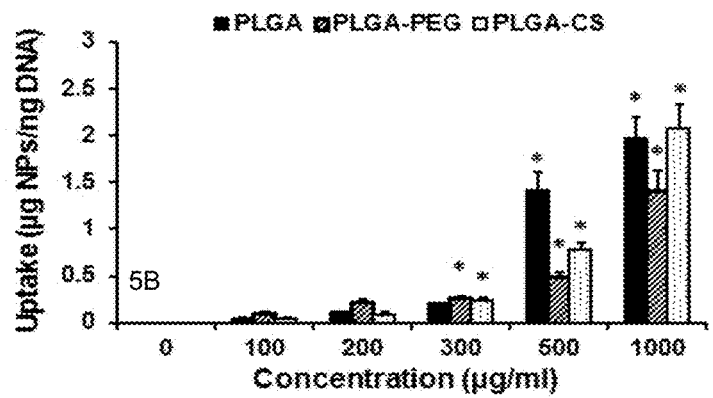

FIGS. 5A-5B illustrates cellular uptake of all NP formulations by alveolar Type 1 epithelial cells studied using BCA protein assay and fluorescence readings from NPs after two hour incubation with increasing NP concentrations. Dose-dependent increase in cellular uptake was observed with increasing NP concentration (e.g., n=3, *$p<0.05$ w.r.t to cellular uptake at 100 µg/ml).

The uptake of all NPs by AT1 cells following a 2 h-incubation with increasing NP concentrations was studied. As illustrated in FIGS. 5A-5B, NP formulations of the present subject matter exhibited concentration-dependent uptake by human AT1 cells.

Higher in vitro NP uptake of natural polymer-based NPs than synthetic-polymer based NPs by lung cells grown in culture was observed. This disparity may have occurred due to differential uptake rates of different polymer-based NPs by cells over time. A variation in uptake rates of PLGA-based NPs by different cells in a concentration and incubation time-dependent manner. Interactions between the cell membrane and polymers may affect the uptake of NPs by human AT1 cells. For example, the negatively-charged cell membranes tend to favor the positively-charged chitosan NPs, resulting in higher cellular uptake of these particles.

Figure 6:
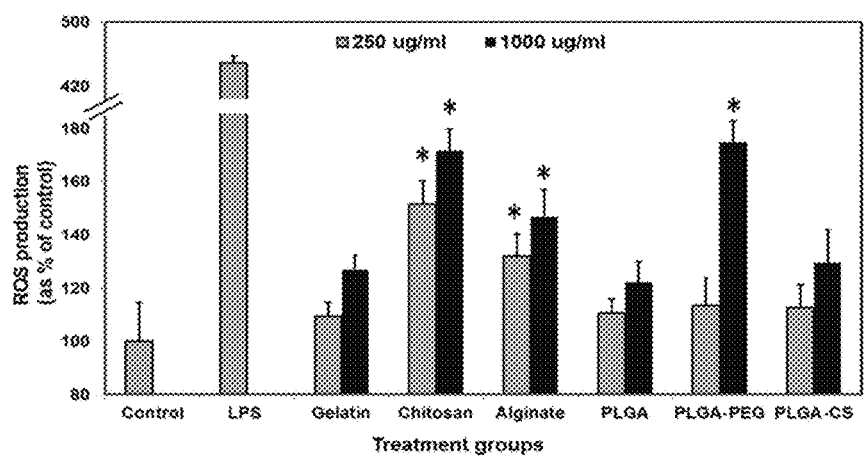
FIG. 6 graphically illustrates the effect of NPs on Reactive Oxygen Species (ROS) according to some embodiments described herein.
Figure 7A:
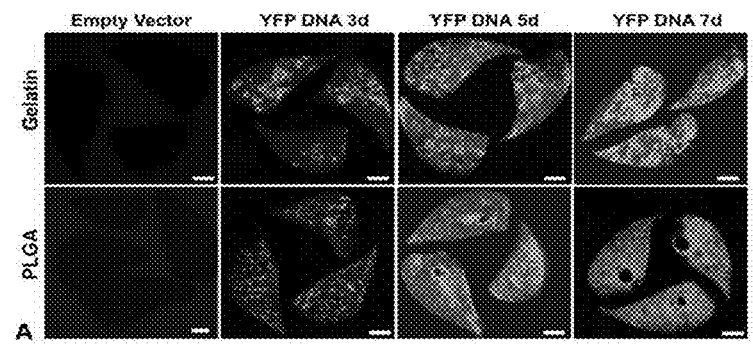
FIGS. 7A-7B are microscopy images of lung tissue illustrating the uptake of NPs following nebulization according to some embodiments described herein.
Figure 7B:
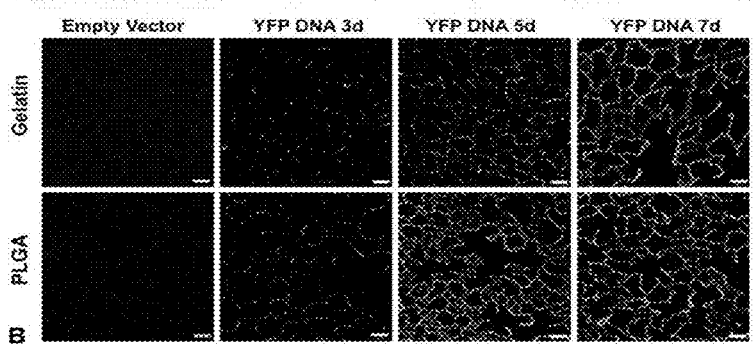
Figure 8A:
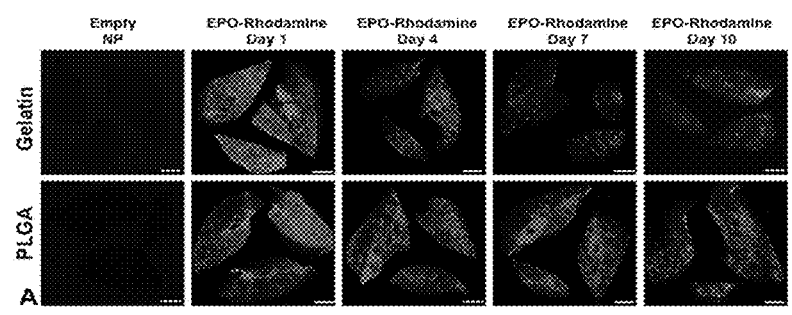
FIGS. 8A-8B are microscopy images of lung tissue illustrating the uptake of NPs following nebulization according to some embodiments described herein.
Figure 8B:
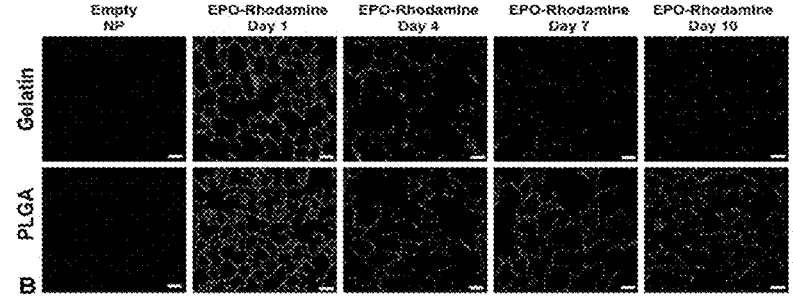

FIG. 6 illustrates the effect of NPs on ROS production by alveolar Type 1 cells following a 24 hour exposure. ROS production was calculated as a percentage of control (i.e., cells grown in media only). Significant ROS production was seen in cells exposed to both concentrations of chitosan and alginate NPs compared to the control samples. Significant ROS production was also observed on treatment with 1 mg/mL PLGA-PEG NPs (i.e., *$p<0.05$ w.r.t control).

A cell activation study was conducted to determine whether NP uptake by AT1 cells can cause oxidative stress. ROS are factors and free radicals known to cause oxidative stress and eventual apoptosis in cells. Inhalation of toxic substances can result in overproduction of ROS by the cells which in turn can cause inflammation in the lung. In this study, ROS produced by cells cultured in media only served as a control. As illustrated by FIG. 6, was observed that chitosan and PLGA-PEG NPs showed greater ROS production (i.e., 172 and 175% of the control, respectively) at 1000 µg/ml concentration among all the formulations. Treatment with alginate NPs also triggered ROS production (i.e., 132% and 147% with respect to the control at 250 µg/ml and 1000 µg/ml concentrations respectively).

On the other hand, gelatin and PLGA NPs triggered minimal ROS production (i.e., 127 and 122% of the control respectively at 1000 µg/ml concentration). LPS initiated ROS production that was 425% of the control. Previous studies on mice have reported the moderately pro-inflammatory properties of PEGylated nanocarriers 48 hours following instillation, which is in keeping with the vitro study conducted. The inflammatory effects of chitosan are consistent with in vivo reports in which chitosan microparticles caused dose-dependent inflammatory effects in rat lungs following inhalation. However the inflammation was reported to be mild compared to that induced by LPS.

Taken together, the results obtained imply that gelatin and PLGA NPs possess the most promising characteristics as nanocarriers for pulmonary delivery of biological agents. The results are provided in Table 2 below. Both nanocarriers were within the appropriate size range for alveolar deposition with minimum clearance by alveolar macrophages. Further, they showed excellent stability, good cytocompatibility and dose-dependent uptake by AT1 cells. Due to their overall promising features, both PLGA and gelatin NPs were chosen for in vivo studies.

TABLE 2

Comparison of physical-chemical, in vitro and in vivo characteristics of the formulated NPs

| | Natural polymer-based | | | Synthetic polymer-based | | |
|---|---|---|---|---|---|---|
| Nanoparticle | Gelatin | Chitosan | Alginate | PLGA | PLGA-CS | PLGA-PEG |
| Size < 200 nm | Yes | No | No | Yes | Yes | No |
| Stability at 5 d | Yes | No | No | Yes | Yes | Yes |
| Burst core release (2 d) | <40% | >40% | <40% | >40% | <40% | <40% |
| Sustained core release (3 wk) | >80% | >80% | <80% | >80% | >80% | >80% |
| Time and concentration dependent cell uptake | Yes | Yes | Yes | Yes | Yes | Yes |
| Cytocompatibility | Up to 1 mg/ml | Up to 1 mg/ml | Up to 1 mg/ml | Up to 2 mg/ml | Up to 2 mg/ml | Up to 1 mg/ml |
| Pulmonary distribution of delivered or expressed protein following nebulization | Less uniform or sustained | — | — | More uniform and sustained | — | — |

Example 4

In Vivo Studies

In Vivo Delivery of Protein- or cDNA-Loaded Gelatin and PLGA NPs

All animal procedures were conducted at University of Texas at South Western (UTSW) following approval from the Institutional Animal Care and Use Committee (IACUC) at UTSW. Sprague-Dawley rats (about 300-400 grams body weight) were given intraperitoneal injection of ketamine (50 mg/kg) and xylazine (5 mg/kg) for anesthesia. An otoscope was used to visualize the larynx and then a guide wire was used to insert a 14 gauge cannula into the trachea. Heart rate and transcutaneous oxygen saturation was monitored throughout the experiment.

Based on the characterization results obtained under Example 3, PLGA and gelatin NPs were chosen for in vivo studies. In an exemplary embodiment, 4.5 mg of NPs encapsulating (a) yellow fluorescent protein (e.g., pEYFP-N1, kindly provided by Dr. Makoto Kuro-o, Dept. of Pathology, UTSW) encoded plasmid DNA or (b) recombinant human EPO (e.g., provided by Cell Sciences, located in Canton, Mass., 100 IU/kg body weight) was dispersed well in 0.5 mL of sterile 0.9% saline, and aerosolized through the cannula for 3 min using a pediatric mesh nebulizer (e.g., Aeroneb™, 4-6 μm droplets). Only one nanoparticle formulation was given per animal. NPs encapsulating empty vectors were aerosolized into the control group by the same method. The rats were observed until complete recovery from anesthesia following NP administration.

At predetermined time points (i.e., 3, 5 and 7 days post-treatment), the rats were sacrificed by giving an intraperitoneal injection of Euthasol™ overdose (pentobarbital 86 mg/kg and phenytoin 11 mg/kg), which stops the heart. Tracheal instillation of 4% paraformaldehyde at 25 cm $H_2O$ of airway pressure was done to inflate the lungs and then remove them intact. The lobes were then fixed and serially sliced at 3 mm intervals. The slices were then imaged by a biofluorescence imager (CRI Maestro 2, Cambridge Research & Instrumentation Inc., Waltham, Mass.). The tissue was fixed by embedding in paraffin, and the histological sections (4 μm thickness) were visualized using a confocal microscope. Similarly in order to study the biodistribution of NPs, the kidney and liver was also removed and serially sliced followed by imaging using biofluorescence imager and confocal microscopy.

Results:

FIG. 7A depicts biofluorescence images of rat lung slices fixed at 3, 5 and 7 days after nebulization of gelatin or PLGA based NPs loaded with YFP cDNA, compared to control lungs following nebulization of the corresponding NPs loaded with empty vector. The panels show increasing YFP expression up to 7 days following nebulization; expression was greater and more uniform using PLGA than gelatin NPs.

FIG. 7B depicts confocal fluorescence microscopy of histological sections taken from the corresponding lungs shows increasing and widespread YFP expression up to 7 days post-inhalation compared to the respective controls.

A single dose of gelatin or PLGA NPs incorporating YFP DNA or recombinant human EPO nebulized to the lungs of anesthetized and intubated rats resulted in widespread and increasing fluorescence throughout lung tissues up to 7 days. In FIGS. 7A-7B, the pattern of distribution observed in lung slices and histological sections increased from punctate (day 3) to diffuse (days 5 and 7) in all lobes, consistent with persistent gene expression and YFP production by lung cells.

FIG. 8A depicts biofluorescence images of rat lung slices fixed at 1, 4, 7 and 10 days following nebulization of gelatin or PLGA-based NPs loaded with rhodamine-conjugated recombinant human erythropoietin (EPO-Rhodamine) compared to control lungs following nebulization of the corresponding empty NPs. Confocal fluorescence microscopy of histological sections taken from the corresponding lungs. As FIG. 8B illustrates, these panels show more sustained fluorescence up to 10 days post-inhalation using PLGA NPs compared to those of gelatin NPs.

As seen in FIGS. 8A-8B, a single inhalational dose of gelatin or PLGA NPs incorporating EPO-rhodamine resulted in widespread fluorescence in lung tissue that persisted for at least 10 days. At the same delivered dose of cDNA or protein, tissue expression was uniform following inhalation of both protein and cDNA-loaded PLGA and gelatin NPs. However, uniform protein expression was observed for a longer time following inhalation of PLGA NPs than that following gelatin NP inhalation.

Although AT1 cells showed greater uptake of gelatin NPs than PLGA NPs in vitro, the in vivo lung tissue distribution profile was relatively similar for both PLGA and gelatin NPs loaded with YFP cDNA. Greater fluorescence was observed with time in lung slices of animals administered Rhodamine-tagged EPO encapsulated PLGA NPs than gelatin NPs containing the same protein. Cellular uptake decreases with increasing size and hydrophilicity of the polymeric NPs, thus, the observed variation between in vitro and in vivo results could potentially be explained by the slightly larger size of gelatin NPs following drug encapsulation (~260 nm), which may result in more rapid clearance by alveolar macrophages. The inherent hydrophobicity of PLGA may have contributed to its greater uptake in vivo compared to the hydrophilic gelatin NPs.

Additional factors in intact lung, such as the amount and physical properties of alveolar lining fluid as well as various extracellular and intracellular clearance mechanisms, could also have differentially influenced the distribution, penetration and retention of nebulized NPs in tissues. The data thus illustrate the importance of verifying in vitro test results with in vivo results. The results obtained suggest that PLGA and gelatin NPs can be used as potential nanocarriers for inhalational delivery of proteins and DNA are about equal, but PLGA NPs are more effectively retained in the distal lung under physiological conditions. Inhalation of NPs via a nebulizer is established as an effective mode of delivery of therapeutic reagents to the lung and its tumors.

Administration of drug-loaded NPs via nebulizers, permits the non-invasive delivery of therapeutic agents with high specificity to lung tumors. The inhalation drug delivery route also diminishes common chemotherapy side effects associated with existing intravenous routes.

Figure 9A:
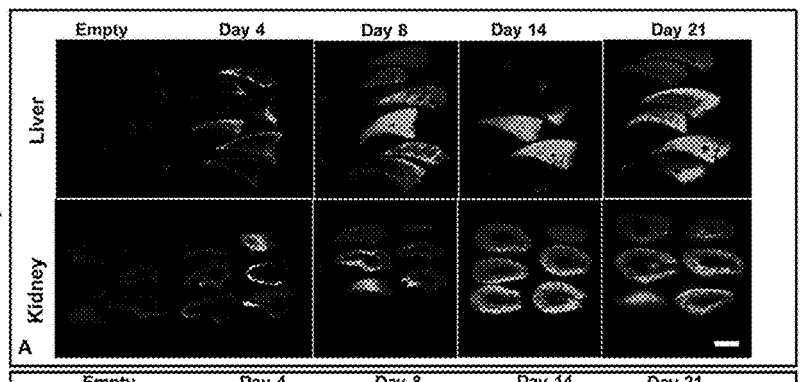
FIGS. 9A-9B are microscopy images of kidney and liver tissue illustrating the effect of NPs on other organs following nebulization according to some embodiments described herein.
Figure 9B:
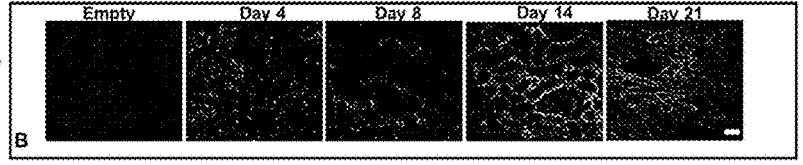

FIGS. 9A-9B depict biodistribution of NPs following nebulization. FIG. 9A depicts biofluorescence images of rat liver and kidney slices fixed at 4, 8, 14 and 21 days following nebulization of gelatin or PLGA-based NPs loaded with green fluorescent protein (GFP)-tagged human erythropoietin receptor (EPOR) cDNA compared to those of control samples (nebulization of the corresponding empty NPs). FIG. 9B depicts confocal fluorescence microscopy of the kidney cortex showing fluorescence up to 21 days.

Further biodistribution studies were conducted to determine the fate of the NPs following nebulization. PLGA NPs containing GFP encoding human EPOR cDNA was nebulized into anesthetized and intubated animals Fluorescence was observed in kidney and liver slices of the nebulized animals from day 4 until day 21 indicating that some of the NPs entered the systemic circulation from the lung following nebulization and were expressed in other organs including the liver and kidneys. Further studies will determine the route of elimination of NPs from the body.

Example 5

Development of PLGA-SPIO NPs

Based on the results obtained in Examples 2-4 described above, PLGA NPs were found to be most promising as nanocarriers for delivery of active compounds (protein and DNA) to the lung via nebulization. In order to validate pulmonary delivery of PLGA NPs and release of its encapsulated agents at the intended site, SPIO-encapsulated PLGA NPs (PLGA-SPIO NPs) were developed. A similar procedure as that of PLGA nanoparticle preparation was followed.

For example, 20 mg of SPIO and 90 mg of PLGA was added to 2 mL chloroform and sonicated for 8 mins at 20 W. This mixture was then added dropwise to PVA solution (5% w/v) and sonicated at 50 W for 10 mins. Following overnight stirring for chloroform evaporation, the NP solution was centrifuged at 1000 rpm for 2 minutes to remove unloaded SPIO aggregates, which forms the pellet. The supernatant containing the prepared PLGA-SPIO NPs was then centrifuged at 25,000 rpm, 20 minutes followed by lyophilization to get the NPs.

Example 6

Characterization of PLGA-SPIO NPs

Particle characterization via DLS, TEM, and Fourier transform infrared (FTIR) spectroscopy were performed to ensure that SPIO has been incorporated within the PLGA particles. Iron content within these particles was further assessed using a standard iron assay. For example, a 48 well plate was taken and 100 µl of PLGA-SPIO NPs (1 mg/mL) was added to the wells. Subsequently, 100 µl of 50% v/v hydrochloric acid (HCl) was added and the plates were incubated overnight at 37° C. The following day, 1 mg/mL of ammonium per sulfate (APS) solution was added to the wells. The well plate was incubated at 37° C. for 15 mins following which 0.1 M potassium thiocyanate (PTC) solution was added. The well plate was incubated at 37° C. for 15 mins more following which absorbance readings were taken at 478 nm using a spectrometer.

A superconducting quantum interference device (e.g., SQUID, Quantum Design) magnetometer was used to study the magnetic properties of the particles prepared. The nanoparticle powder was embedded in epoxy resin beads and exposed to varying magnetic fields at room temperature to obtain the hysteresis loop. This was then compared to the hysteresis loop of bare SPIO obtained by the same method.

In addition to characterization of magnetic properties, the particles were also studied for their stability in various solutions such as DI water, 10% FBS, 0.9% saline and Gamble's solution as mentioned earlier. Release studies were also conducted as explained above using BSA- and Texas Red Albumin (TR-A)-loaded PLGA SPIO NPs. TR-A release was measured based on fluorescence readings at $\lambda_{ex}$ 596 nm and $\lambda_{em}$ 615 nm.

Results:

FIGS. 10A-10D illustrate TEM image of (A) PLGA and (B) PLGA-SPIO NPs. (C) FTIR spectra of SPIO, PLGA and PLGA-SPIO NPs (D) Comparison of hysteresis loops of bare SPIO and PLGA-SPIO NPs indicating a decrease in magnetization in polymer-bound iron oxide NPs. The coercivity and remanence values remain within the range suitable for magnetic-based drug delivery.

Figure 10A:
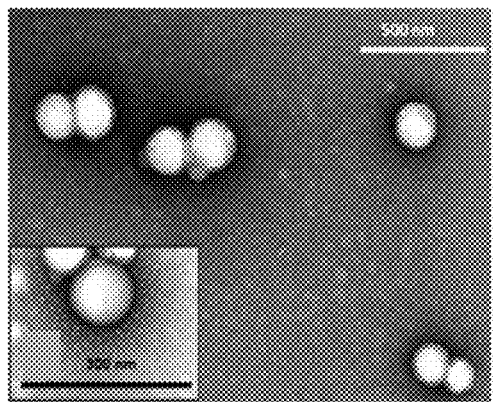
FIG. 10A is a TEM image of PLGA NPs according to some embodiments described herein.
Figure 10B:
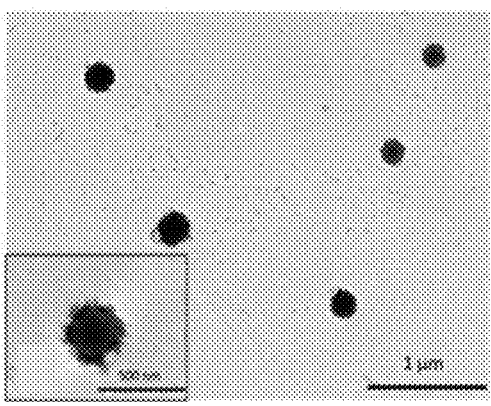
FIG. 10B is a TEM image of PLGA-SPIO NPs according to some embodiments described herein.

The synthesized PLGA-SPIO NPs had an average size of 250±97 nm and polydispersity of 0.22±0.01, indicating minimal particle size variation. The zeta potential of −38±0.5 mV imply that these particles are highly stable. FIGS. 10A-10B depict PLGA NPs as having a smooth spherical morphology, and PLGA-SPIO NPs as having a rough, speculated shape due to the presence of iron oxide which was distributed on the particle surface. Iron assay results indicated that the PLGA-SPIO NPs contain 11.8% iron by weight.

Figures 10C, 10D:
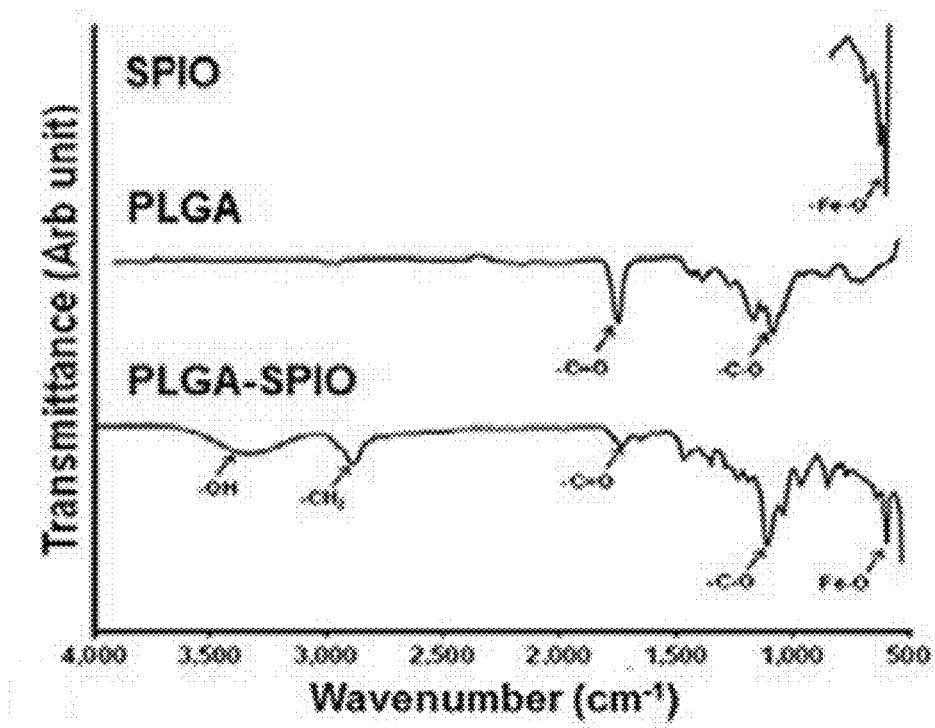
FIG. 10C graphically illustrates a Fourier transform infrared (FTIR) spectra of NPs according to some embodiments described herein.
FIG. 10D graphically illustrates hysteresis loops of bare SPIO and PLGA-SPIO NPs according to some embodiments described herein.

FIG. 10C is the FTIR spectra of PLGA-SPIO NP having characteristic —OH stretching by the carboxylic acid groups in PLGA at 3320 cm-1. Other peaks representative of bare iron oxide NPs (Fe—O peak at 590 cm-1) and PLGA (C=O stretching at 1735 cm-1 and C—O stretching at 1072 cm-1) was also observed.

FIG. 10D illustrates the magnetic properties of PLGA-SPIO NPs studied using SQUID magnetometry showed a decrease in saturation magnetization of PLGA-SPIO NPs compared to bare SPIO. This decrease occurred due to the diamagnetic property of the polymer coating. Magnetic NPs with saturation magnetization as low as 7-8 emu/g have shown attraction towards small magnets, which supports their experimental use as targeting contrast agents. Further, a remanence of 0.022 and coercivity of 69.8 was observed demonstrating that PLGA-SPIO NPs exhibit similar properties as bare SPIO which has a remanence of 0.0028 and a coercivity of 75.4.

FIG. 11A illustrates NP stability studies in DI water, FBS, 0.9% saline, and simulated lung fluid (Gamble's solution) (n=4 each), indicating good stability of PLGA-SPIO NPs over 5 days with minimal aggregation.

FIG. 11B illustrates the release of TR-A and BSA from PLGA-SPIO NPs indicating a bi-phasic release involving an initial burst release of 40% of encapsulated agent within 2 days followed by sustained release for 21 days (n=4).

Stability studies in DI water, FBS, saline and Gamble's solution showed that PLGA-SPIO NPs maintained their initial particle size with minimal aggregation for over 5 days (see e.g., FIG. 11A). Drug release analysis showed that both BSA and TR-A-loaded PLGA SPIO particles showed a burst release of about 38% of the loaded BSA and 44% of the loaded TR-A within 2 days. This was followed by a characteristic sustained release of 89% of loaded BSA and 82% of TR-A over 21 days (see e.g., FIG. 11B). Release occurs via bulk erosion of PLGA by the hydrolysis of its ester bonds.

Example 7

In Vitro Studies on PLGA-SPIO NPs

The cytocompatibility of PLGA-SPIO NPs was tested on both human AT1 cells as well as human dermal fibroblasts (HDFs). The influence of nanoparticle dose and incubation time on cellular uptake was also determined. Dose-dependent cellular uptake was done as explained in section 2.2.6. To study time-dependent uptake, the cells were incubated with NPs at a fixed concentration of 100 µg/ml for varying durations (1, 2, 4 and 6 hours). Following particle incubation, the cells for both uptake studies were extensively washed to remove free NPs and lysed using 1X-Triton solution. The amount of NPs taken up by the cells was measured using iron assays. The amount of total cell protein per well was measured by Pierce BCA assay and used to normalize the iron uptake results.

A study was also conducted to determine activity of compounds released from PLGA NPs. Briefly, PLGA NPs encapsulating recombinant human erythropoietin (e.g., EPO available from Cell Sciences, located in Canton, Mass.) (2 mg/mL) was incubated in incomplete RPMI media at 37° C. for 5 days. At the end of the study, the samples were centrifuged and the supernatant was collected. This supernatant containing released EPO was tested for its ability to maintain the viability of Ba/F3 cells known to stably over-express EPO receptor and require EPO for survival (e.g., courtesy of Dr. Lily Huang, Dept. of Cell Biology, UT Southwestern Medical Center). The groups used for this study include (a) RPMI only, (b) EPO (100 IU/ml) in RPMI, (c) EPO (100 IU/ml) with empty PLGA NPs (2 mg/mL) in RPMI, and (d) RPMI containing EPO released from PLGA NPs. Ba/F3 cells grown in WEHI (Walter and Eliza Hall Institute) were conditioned medium at a density of 5×105 cells per well were washed and switched to RPMI medium. These cells were incubated for 72 h at 37° C. following addition of 90 µl of supernatants obtained earlier after the 5 day incubation. Cell viability was determined by MTT assays following manufacturer's instructions.

Results:

FIGS. 12A-12B illustrate cell uptake studies demonstrating that PLGA-SPIO at a concentration of 500 µg/ml were compatible with human AT1 cells. FIG. 12C graphically illustrates the results of cell viability studies of NPs according to some embodiments described herein. For example, FIG. 12A illustrates the dose-dependent uptake of PLGA-SPIO NPs by human AT1 cells up to a nanoparticle concentration of 300 µg/ml was observed.

FIG. 12B illustrates the time-dependent uptake of PLGA-SPIO NPs (100 µg/ml) by AT1 cells over 6 h, and FIG. 12C illustrates that the viability of EPO-dependent Ba/F3 cells was poor in EPO-free (RPMI) medium (control), but rescued in medium containing EPO, EPO plus empty PLGA NPs, or medium incubated for 5 days with PLGA NPs encapsulating EPO [PLGA(EPO)].

Human dermal fibroblasts and AT1 cells maintained >90% viability when incubated with PLGA-SPIO particles up to a concentration of 500 µg/mi. Cell viability was >80% at 1000 µg/ml concentration. Factors such as the cell line tested, polymer composition and SPIO concentration may contribute to differential cytocompatibility. Concentration dependent uptake of PLGA-SPIO NPs by AT1 cells was observed within 2 h of incubation with saturation of uptake occurring at 300 µg/ml NP concentration (see e.g., FIG. 12A). Uptake by AT1 cells was also found to saturate within 2 hours of incubation, indicating time-dependence of uptake (see e.g., FIG. 12B).

To observe the bioactivity of released therapeutic agent, EPO released from the NPs was studied for its activity on EPO-sensitive Ba/F3 cell lines. Ba/F3 cells showed poor viability in control medium (see e.g., FIG. 12C). While empty PLGA NPs had no significant effect on cell viability, the EPO in the media helped keep the cells viable. The EPO-containing supernatants obtained after 5 days' release from the NPs also significantly improved Ba/F3 cell viability (56±6%) compared to the control group (<20%).

Example 8

In Vivo Studies on PLGA-SPIO NPs

In Vivo Delivery of PLGA-SPIO NPs Encapsulating Various Payloads

Animal procedures were conducted at UTSW with the approval of the Institutional Animal Care and Use Committee (IACUC) at UTSW. PLGA-SPIO NPs were synthesized as described above (e.g., Example 1) and loaded with different fluorescent probes: near-infrared dye (NIR-797), rhodamine conjugated bovine serum albumin (BSA-rhodamine), Green Fluorescent Protein (GFP) (available from Santa Cruz Biotechnology Inc., located in Santa Cruz, Calif.), or plasmid DNA vector encoding yellow fluorescent protein (pEYFP-N1).

The particles were then administered to Sprague Dawley rats as explained above. One hour following inhalational delivery of PLGA-SPIO NPs, the anesthetized animals underwent magnetic resonance imaging (MRI) (e.g., 3T whole-body human scanner Achieva™, Philips Medical Systems, Best, Netherlands) with a small animal solenoid radio-frequency (RF) coil (e.g., 63 mm in diameter and 100 mm in length; such as those available from Philips Research Europe, located in Hamburg) using a three-dimensional ultrashort echo time (e.g., UTE, echo time<500 µs) sequence with projection acquisition of free induction decay. This sequence enabled a comparison of endogenous signal intensity (SI) of the lung parenchyma with SI of the experimental group as well as the control group which was given saline only.

At 3, 5 and 7 days post-treatment, the rats were sacrificed via intraperitoneal injection of Euthasol™ and lung slices were imaged by a biofluorescence imager while histological sections were examined under a fluorescent microscope. Further, Prussian blue staining was done to visualize iron particles uptake by lung cells, using light microscopy and TEM.

Results:

FIG. 13 illustrates the signal intensity changes following inhalation of PLGA-SPIO nanoparticles, using UTE MRI. The upper panel of FIG. 13 illustrates that the lung in rats administered PLGA-SPIO via nebulization showed significant darkening compared to control untreated rats or rats that received nebulized saline. At any given echo time, the normalized SI of lung parenchyma was lower following PLGA-SPIO inhalation when compared to SI of control and untreated animals.

Following a single inhalation dose of PLGA-SPIO NPs, the normalized MR SI of lung parenchyma became much lower than SI of simultaneous saline-treated or untreated control lungs. SPIO has been used as a "negative" MRI contrast agent owing to its effect of shortening the proton spin-spin relaxation time (T2) and causing a reduction of signal intensity on MRI. The results obtained demonstrate this effect of SPIO encapsulated in the PLGA NPs using UTE MRI (see, e.g., FIG. 13).

FIGS. 14A-14H illustrate the distribution of inhaled PLGA-SPIO NPs in a rat lung. In FIGS. 14A to 14D, Prussian blue staining was negative for (A) control lung (saline inhalation) while scattered blue stains (arrows) were seen in the alveolar septa of animals given the nanoparticle formulation In FIGS. 14E-14H, the TEM images show the presence of NPs (arrows) in alveolar interstitial fibroblasts (bar=1 µm), the interstitium and an endothelial cell (bar=1 Images at higher magnification show dispersed free iron particles (~5 nm) within the interstitium and endothelium (bar=50 nm), and within alveolar type-1 epithelium (bar=50 nm).

Additionally, light microscopy images of Prussian blue tissue staining showed scattered distribution of iron oxide within alveolar septal cells as well as alveolar macrophages under light microscopy (FIGS. 14A-14D). PLGA-SPIO NPs distribution within the lung cells was also visualized using TEM. (FIGS. 14E-141).

Figure 15:
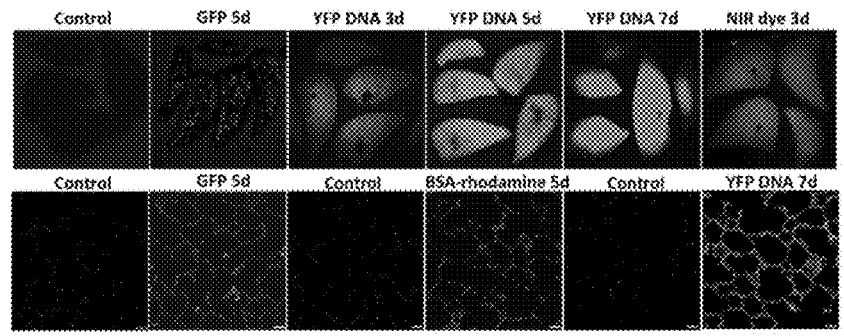
FIG. 15 are microscopy images of lung tissue illustrating the uptake of NPs following nebulization according to some embodiments described herein.

In FIG. 15, the upper row illustrates the biofluorescence of fixed rat lung slices at different times following PLGA-SPIO NP nebulization. Encapsulated compounds include GFP or BSA-rhodamine protein, YFP cDNA, and near-infrared (NIR) dye, compared to control (saline nebulization). The scattered GFP expression (5 days), increasing YFP expression (from 3, 5, to 7 days), and diffuse NIR dye (3 days) indicate that the particles were successfully delivered to the lung and released their payloads at the site (bar=0.5 cm).

In the lower row of FIG. 15, confocal fluorescence microscopy shows scattered GFP and diffuse BSA-rhodamine expression at 5 d, and widespread YFP expression at 7 d after inhalation, compared to their respective controls (bar=50 µm).

The distribution of nebulized NPs was observed in lung slices FIG. 15, upper panels, and histological sections, FIG. 15, lower panels. The control lung (saline) showed no distinct fluorescence while, a single inhalation of NPs containing NIR dye resulted in diffuse fluorescence throughout the lung, even 3 days after administration.

A single inhalation of GFP-containing NPs also showed extensive peribronchial and peribronchiolar fluorescence up to 5 days. Previous studies indicate the inhalational delivery of insulin-loaded PLGA nanospheres as having a sustained insulin release in the lung and hypoglycemic effect for up to 48 hours. A single inhalation of NPs encapsulating YFP cDNA resulted in diffuse and increasing fluorescence at least up to 7 days. This is consistent with persistent gene expression and YFP production by lung cells seen following PLGA NP uptake. The results obtained were also consistent with published in vitro studies using DNA-containing PLGA-polyethyleneimine (PEI) NPs (e.g., 207-211 nm), which were localized to the endo-lysosomal compartment of lung epithelial cells within 6 hours of treatment, indicating their potential as gene carriers.

To summarize the results from Examples 1-8, six different polymeric NPs were initially synthesized and characterized in terms of respective physical and chemical properties, in vitro cytocompatibility and cellular uptake as well as in vivo deposition and action of the core compound. Gelatin and PLGA NPs showed the smallest sizes (diameters) of about 187 and 160 nm respectively, and also maintained consistent particle sizes in water, serum, saline and Gamble's solution.

Further, gelatin and PLGA they showed a bi-phasic drug release profile, although PLGA NPs had the highest burst release within two days. Synthetic PLGA-based NPs showed the highest cytocompatibility with AT1 cells while natural polymeric NPs showed the highest uptake at a given concentration. Based on the results from in vitro characterization, PLGA and gelatin NPs showed the most favorable characteristics for pulmonary delivery. Following inhalational delivery of PLGA NPs, more sustained and uniform distribution of encapsulated protein was seen compared to those of gelatin NPs.

MDNPs may be fabricated to have different release profiles of a single or a combination of chemotherapy agents and radiosensitizers. This capability provides an opportunity to assess the treatment effectiveness of combined and localized delivery of chemotherapy agents and radiosensitizers in and surrounding the lung tumor.

Example 9

Western Blot Analysis of Folic Acid Receptors on Lung Cancer Cells

Two different lung cancer cell lines, A549 and H460 for expression of folic acid receptors were compared. First the cells were lysed using a lysis buffer consisting of Tris (50 mmol/l) of pH 7.5, 1% NP40, EDTA (1 mmol/l) and a protease and phosphotase inhibitor cocktail (phenylmethylsulfonylfluoride (1 mmol/l), sodium orthovanadate (0.2 mmol/l), sodium fluoride (0.1 mmol/l), aprotinin (10 µg/ml), and leupeptin (10 µg/ml). The lysates were sonicated, incubated in ice for 15 minutes and then centrifuged at 12000 rpm for 10 minutes. Following quantification of cell protein by Bradford assay (available from Bio-Rad, located in Hercules, Calif.), 20 µg of protein was subjected to a 10% SDS-Poly acrylamide gel electrophoresis (SDS-PAGE) and transferred to polyvinylidene difluoride membranes and probed with Anti-folate binding protein antibodies (available from Abcam, located in Cambridge, Mass.) as per manufacturer's instructions. Actin was used as loading control.

Analysis of Binding Efficiency of Folic Acid to Cellular Folate Receptors:

The binding of folic acid to folate receptors was studied using Resonant Sensors Bioassay system (e.g., available from Resonant Sensors Inc. (RSI), located in Arlington, Tex.). A549 and H460 lung cancer cells as well as AT1 cells were seeded at a density of 10,000 cells/well in RSI sensor 96-well plates, which were incubated at 47° C. for 24 hours to allow cell attachment. For folic acid binding efficiency studies, the cells were incubated with folic acid at varying concentrations (i.e., 0, 0.1, 1, 5, 10, 15 µM) for 3 hours in the RSI system and peak shift with cell binding over time was studied. The results were plotted as peak shift vs time where greater binding of folic acid to cells resulted in greater peak shifts.

Figure 16A:
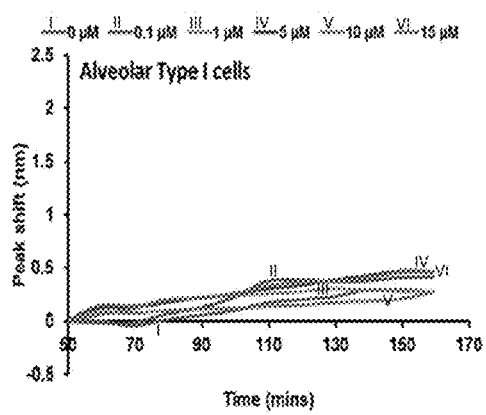
Figure 16B:
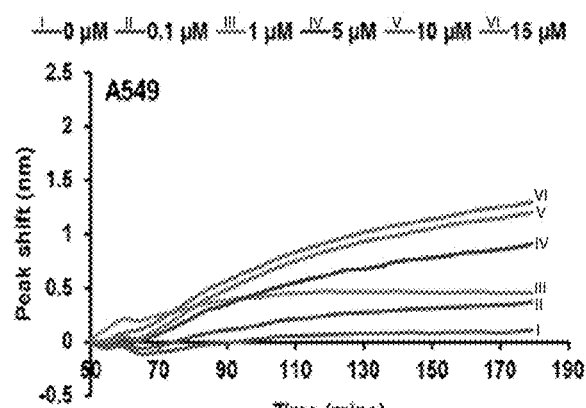
Figure 16C:
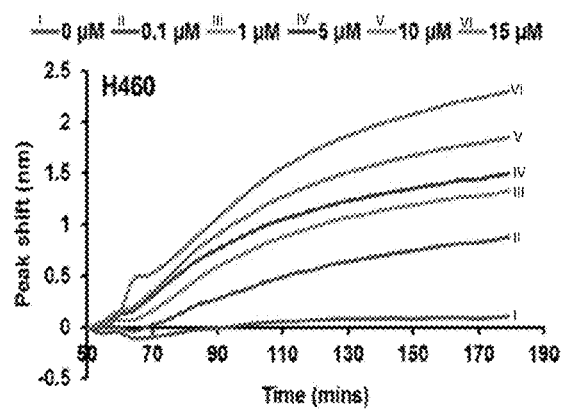

Results of Western Blot and Folic Acid Binding Efficiency:

FIGS. 16A-16C are binding kinetic curves of ligand-conjugated NPs with specific lung cancer cells. RSI bioassay system results demonstrate that there is no dose-dependent increase in peak shift on treatment of human AT1 cells with folic acid, see FIG. 16A. Western blot results demonstrated that the folate receptors are overexpressed on both A549 and H460 lung cancer cells. An increase in peak shift was observed for both A549 cells (FIG. 16B) and H460 cells (FIG. 16C) compared to their respective controls (0 µM) indicating folic acid binding to cell surface receptors. H460 cells showed a comparatively larger peak shift indicating greater affinity for folic acid (n=4).

A minimal peak shift on incubating AT1 cells with folic acid (FIG. 16A) is shown. This peak shift was also not dependent on the concentration of folic acid. On the other hand, H460 cells had comparatively larger peak shifts than both 549 and ATI cells (FIG. 16B). The larger peak shifts of H460 compared to A549 and AT1 cells indicate that H460 cells have more affinity for binding to folic acid. When the components within the RSI sensor well plates are illuminated with an incident broadband light, light of a specific wavelength gets reflected or transmitted back from it. When folic acid binds to H460 and A549 cells, a shift occurs in the resonance wavelength emitted from the plate. This shift is used to quantify the binding of folic acid onto the cells.

Example 10

Design and Synthesis of MDNPs

A multi-functional dual-drug nanoparticle system (MD-NPs) conjugated with folic acid and loaded with NU7441 (i.e., a potent radiosensitizer) and gemcitabine (i.e., "Gem" an FDA approved chemotherapeutic agent) was prepared. The MDNPs were characterized in terms of their physical properties such as size, surface charge, stability, and magnetic- and stimuli-sensitive properties. The MDNPs can provide targeted, controlled delivery of both radiosensitizers and chemo-drugs to a lung tumor and significantly increase the therapeutic efficacy over conventional therapy. As described herein, the combination of different drugs in one delivery system is shown to minimize the drug dosage while achieving the synergistic therapeutic effect in cancer treatment and overcoming drug resistance.

Development of PLGA-SPIO NPs:

The PLGA-SPIO nanoparticles were prepared by a standard emulsion method. For example, 20 mg of SPIO was added to 90 mg PLGA (50:50) solution in 5 mL DCM (oil phase) and sonicated for 8 mins at 20 W power. This emulsion was then added dropwise to 20 mL of 5% (w/v) PVA solution and sonicated for another 10 mins at 50 W. Following overnight stirring to allow solvent evaporation, the particles were centrifuged at 1000 rpm for 1 min to remove un-encapsulated SPIO, and the NPs in the supernatant were then collected via lyophilization. To carry out drug loading, NU7441 was dispersed well in the DCM solution containing SPIO and PLGA (oil phase). This mixture was then added to PVA solution as described above.

Surface Modification of PLGA-SPIO NPs with Allylamine (AH):

20 mg of PLGA-SPIO NPs was dispersed in MES buffer (pH 4.8) by sonication at 30 W, 10 minutes. The suspension was then kept for stirring and equal parts of N-(3-dimethylaminopropyl)-N'-ethylcarbodiimidehydrochloride (EDC) and N-hydroxy succinimide (NHS) were added to it. Then 130 µl of Allylamine and 14 mg of SDS were added consecutively every 20 minutes. The reaction was allowed to continue for 4-6 hours and the particles were washed and isolated by centrifugation at 15,000 rpm for 20 minutes.

Development of MDNPs:

The final step of the nanoparticle formulation involves formation of the PNIPAAm-CMC shell via free radical polymerization followed by folic acid conjugation. 28 mg of PLGA-SPIO-AH particles was dispersed in DI water by sonication at 40 W for 20 minutes. 58 mg of NIPA, 6 mg of CMC, 13 mg of N, N'-methylenebisacrylamide (BIS) and 50 mg of Sodium dodecyl sulfate (SDS) were added consecutively every 2 mins during sonication. Then the particle suspension was transferred to a 125 ml flask and purged with Nitrogen gas for 30 mins. Following addition of 0.08% (w/v) of Ammonium persulfate (APS) and 50 µl of TEMED, the reaction was allowed to continue in Nitrogen gas for 4-6 hours. The particles were isolated by centrifugation at 15,000 rpm for 20 minutes.

For folic acid conjugation, 0.1% w/v folic acid solution in 5 mL MES buffer (pH 4.7-5) was prepared. Then 20 mg of EDC and NHS was added to it every 30 mins. EDC activates the surface carboxyl groups on folic acid and NHs stabilizes it to form an active ester intermediate. This intermediate then covalently binds to the amine groups of CMC present on the PNIPAAm-CMC shell. 5 mg of the prepared MDNPs was then added and sonicated for 2 minutes at 20 W. Shaking was continued for 24 hours followed by centrifugation at 15,000 rpm, 20 minutes and lyophilization to obtain the MDNPs.

For drug loading, 1 mg of gemcitabine hydrochloride was incubated with 5 mg MDNPs at 4° C. under shaking conditions for 3 days. Since the polymeric shell is hydrophilic below LCST, the drug was loaded into the particles by diffusion. Following drug loading, the MDNPs were washed multiple times by centrifugation and the drug loaded MDNPs were collected via lyophilization. The supernatant following centrifugation was collected and stored for drug loading efficiency determination.

Example 11

Characterization of MDNPs

Physical Properties:

The MDNPs were characterized extensively to observe the respective particle size and surface charge, stimuli-responsive and magnetic properties, stability as well as drug release characteristics. The MDNP size, polydispersity and zeta potential values were obtained using Dynamic Light Scattering technique. For example, 3 mL of DI water was taken in a transparent cuvette and 20 µl of MDNP suspension (1 mg/mL) was added to it. Following insertion of the cuvette in the DLS instrument, readings were taken based on scattering of laser light by Brownian motion of the particles. Transmission Electron Microscopy (e.g., FEI Tecnai G2 Spirit BioTWIN, Hillsboro, Oreg.) was used to observe the size as well as morphology of the particles. A drop of 1 mg/mL nanoparticle suspension was added to a Formvar-coated 200-mesh copper grid (e.g., available from Electron Microscopy Sciences, located in Hartfield, Pa.) and air-dried. The grid was then inserted into the holder within the TEM instrument and particle morphology was observed. In order to confirm the incorporation of all components used during synthesis, FTIR was also conducted on individual components as well as at different stages of nanoparticle preparation.

Results

DLS results at each step of nanoparticle formulation indicate that PLGA-SPIO NPs had a hydrodynamic diameter of 230±98 nm while NPs following AH surface modification, and MDNPs had an average size of 262±79 nm and 289±49 nm respectively. The NPs were highly stable at all steps of synthesis, which is evident from the high zeta potential values of −12, −18 and −36 mV observed for PLGA-SPIO NPs, AH-modified PLGA-SPIO NPs and MDNPs respectively. The polydispersity ranging from 0.12 to 0.32 indicate that the particles are well-dispersed as indicated in Table 3, below.

TABLE 3

Size, surface charge and polydispersity values of the NPs at different stages of preparation

|  | Diameter (nm) | Polydispersity | Zeta potential (mV) |
| --- | --- | --- | --- |
| PLGA-SPIO NPs | 230 ± 98 | 0.22 ± 0.40 | −12 |
| AH-modified PLGA-SPIO NPs | 262 ± 79 | 0.12 ± 0.23 | −18 |
| MDNPs | 289 ± 49 | 0.32 ± 0.31 | −36 |

FIG. 17A is a TEM image established that the particles in the 250-280 nm size range and have a smooth, spherical morphology. FIG. 17B schematically illustrates the core-shell structure of MDNPs and their expected behavior at LCST and acidic pH.

FIG. 17B illustrates an exemplary MDNP system containing two anticancer agents; (i) a potent radiosensitizer (e.g. NU7441, which will inhibit the DNA double strand repair after radiotherapy) in the core, and (ii) a chemotherapeutic reagent (e.g. cisplatin) in the shell. If needed, surface modification of MDNPs with lung cancer specific ligands may be employed.

The MDNP system can also encapsulate a contrast imaging reagent in the core for tracing the drug carrier and detecting the lung cancers. MDNPs in terms of their properties, including particle size, and optimize the payloads (the combination of drugs) to achieve the highest effectiveness used in animal studies.

Notably, FIG. 17B illustrates a core-shell nanoparticle system including a degradable stimuli-responsive (e.g., pH-dependent) polymer shell and a biodegradable polymer core for delivery of multiple chemo-therapeutic agents for rigorous therapy. The NP in FIG. 17B may further comprise a targeting moiety, thus providing targeted and controlled therapy for effective cancer treatment.

Example 12

Magnetic and Stimuli-Responsive Properties of MDNPs

The MDNPs were studied for their magnetic as well as stimuli-responsive properties. In order to determine iron content within the particles, an iron assay was conducted as described in Example 6 above. Additionally, the magnetic property of the particles was analyzed using a SQUID magnetometer. For this study, the MDNPs were well dispersed in epoxy resin beads and inserted into the instrument. Their response to varying magnetic fields at room temperature was recorded and plotted. Finally, agarose phantoms (0.5% w/v) containing varying concentrations of MDNPs (0, 0.25, 0.5, 1, 2 mg/mL) were prepared to determine whether the SPIO within MDNPs can be visualized using MRI. All images were done on a 7T Agilent (Varian) MRI Scanner with a build in fsems sequence. Some major parameters are as follows: TR=5000 ms, TE=8.58 ms, FOV=35×35 mm, slice thickness=1 mm.

In addition to observing magnetic properties, the temperature and pH responsiveness of the MDNPs were also studied. To study pH-responsiveness, the particles were dispersed in solutions of varying pH at room temperature and the size was observed using DLS. Temperature responsiveness of the sample was also studied. Briefly, 5 mg/mL MDNP solution was placed in a quartz cuvette (e.g., available from Starna Cells, located in Atascadero, Calif.) and submerged in a transparent water tank. The temperature of the water in the tank was varied using a temperature controller with a heater and a temperature feedback probe. A laser light of about 609 nm wavelength was then shed on the MDNP sample and the scattered light captured by a photomultiplier (PMT) at 90° angle. A 594 nm long-pass filter was used as the captured-light filter. The signal was averaged 100 times following which the peak intensity of the emission decay curve was used to calculate the intensity. Photographs of the nanoparticle suspension were taken before and at LCST to observe cloudiness of the polymer network.

Results:

The iron content in the SPIO of MDNPs was observed to be about 47%. The magnetic properties were studied both visually as well as using a SQUID magnetometer. It was observed that the NPs dispersed in DI water could rapidly move in the direction of the applied 1.3 T magnet. The hysteresis loop for MDNPs showed that the particles retained their magnetic properties with a remanence of 6.45 (Mr/Ms) and coercivity of 52.6 Oe. According to FIG. 19A, bare SPIO on showed a remanence of 7.16 (Mr/Ms) and coercivity of 66.7 Oe. This decrease in magnetic properties could be due to the generation of a diamagnetic moment by the polymer coatings. Particles with similar or lower magnetization have been successfully used for MRI and drug delivery, indicating the feasibility of the MDNPs in magnetic field-based drug delivery applications, such as magnet-based targeting and MRI.

Figure 19A:
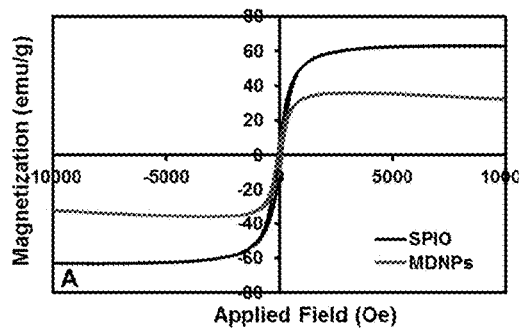
Figure 19B:
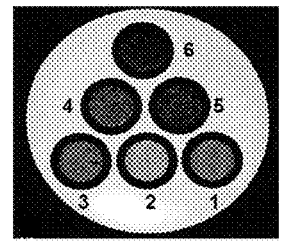
Figure 19C:
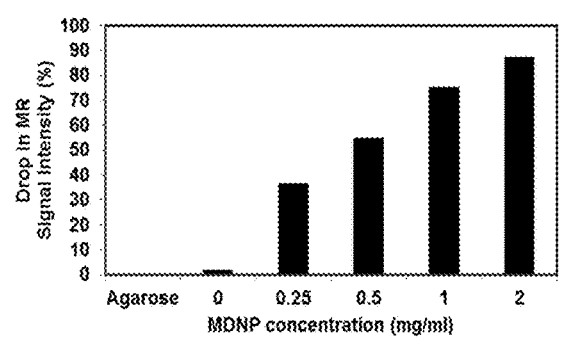

FIGS. 19A-19C depict magnetic properties of MDNPs. In FIG. 19A, the hysteresis loop indicates superparamagnetic property of MDNPs. In FIG. 19B, the magnetic behavior of MDNPs on application of 1.3 T magnet could be observed visually. FIG. 19C is a drop in MR SI for agarose phantoms containing (1) Agarose only (2) MDNPs without iron oxide, (3) 0.25 mg/mL MDNPs, (4) 0.5 mg/mL MDNPs, (5) 1 mg/mL MDNPs, (6) 2 mg/mL MDNPs. The MR SI drop observed with increasing concentration of MDNPs compared to the control (agarose only).

In FIG. 19B, T2-weighted images of MDNPs-containing agarose phantoms showed darker negative contrast with increasing concentration of MDNPs. The percentage drop in MR signal intensity of the phantom with increasing MDNP concentrations was calculated and compared to the control (agarose only). It was observed that there was almost 87% decrease in signal intensity in the case of agarose phantoms containing 2 mg/mL MDNP while 0.25 mg/mL, 0.5 mg/mL and 1 mg/mL MDNP concentrations caused the signal intensity to drop by 36%, 55% and 75% respectively compared to the control (agarose phantom only), see e.g., FIG. 19C.

Figure 20A:
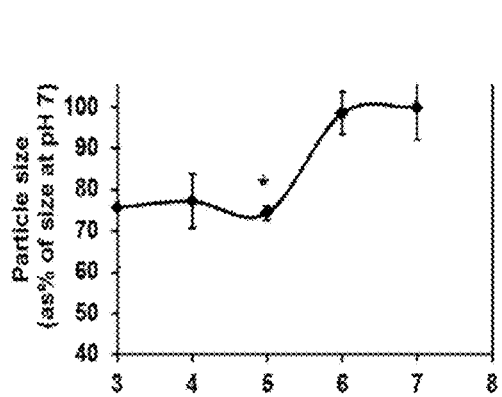
Figure 20B:
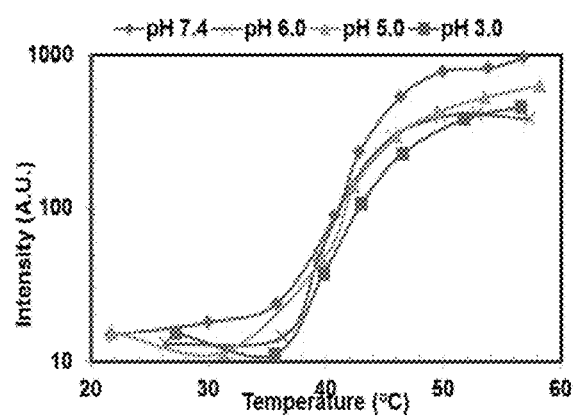

FIGS. 20A-20B illustrate a significant decrease in MDNP size (FIG. 20A) observed with change in environmental pH from 7 to 5 (n=4, *p<0.05 w.r.t particle size at pH 7). MDNPs demonstrated temperature-sensitive behavior with LCST at 40° C. No significant variation in LCST was observed with pH. LCST changes could be observed visually, see e.g., FIG. 20B.

In order to ascertain the stimuli-sensitive properties of the NPs, two studies were performed. DLS studies performed to determine pH sensitivity showed a significant decrease in particle size from pH 7 to pH 5 indicating that the particles shrink in response to acidic pH environment (see e.g., FIG. 20A). The ionization of chitosan chains at low pH and their rapid deprotonation at basic pH could result in instability in the system leading to possible swelling and eventual aggregation. Further, LCST measurements confirmed that the PNIPAAm-chitosan shell can undergo rapid, reversible phase transition at an LCST of 43° C. In addition, a distinct cloudiness in the PNIPAAm-CMC NP suspension was observed at around 43° C. while it remained clear below this temperature (see e.g., FIG. 20B). Therefore it was confirmed that the LCST of PNIPAAm-CMC is achieved at 43° C., and pH was found to have no effect on the LCST of the particles.

Example 13

Stability, Drug Release and Degradation Characteristics of MDNPs

FIGS. 18A-18B illustrate FTIR spectra of (e.g., FIG. 18A) individual components and (e.g., FIG. 18B) each step of nanoparticle synthesis demonstrating that all the components have been incorporated in the final nanoparticle system.

Variation of MDNP size on incubation with DI water, 10% FBS, saline and Gamble's solution at body temperature over time was studied. Briefly, 20 μl of MDNP suspension of 1 mg/mL concentration was added to a cuvette containing the respective solution. The cuvette was incubated at 37° C. and DLS readings were taken every 24 hours to observe changes in nanoparticle size with time. In order to perform drug release studies, the drug loaded particles were dispersed in 4 different solutions (37° C. and pH 7.4, 37° C. and pH 6, 45° C. and pH 7.4, and 45° C. and pH 6) and kept shaking at the respective temperatures. At pre-determined time points, the particles were collected using an external magnet and the supernatant saved for analysis. Then the particle were re-dispersed in fresh solutions of appropriate pH and incubated at the designated temperatures. The amount of gemcitabine released was detected at 234 nm absorbance using a spectrophotometer. NU7441 release was detected at λex 470 nm and λem 520 nm using a spectrophotometer. Further, degradation studies were conducted on the MDNPs. For example, 4 mg/mL of nanoparticle suspension was prepared in DI water and incubated at 37° C. At each time point, the particles were collected using a 1.3 T magnet and the supernatant was removed. Following air-drying, the particle weight was measured to determine decrease in weight over time.

Figure 21A:
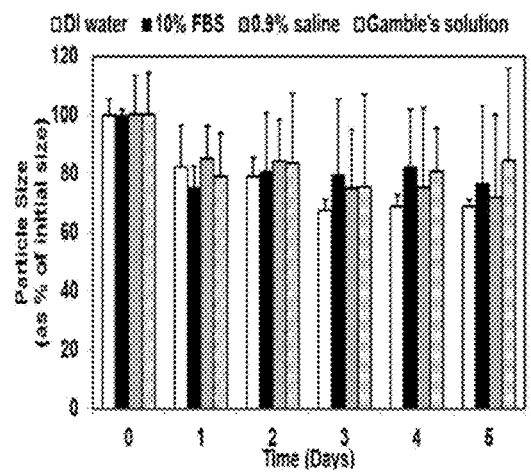
Figure 21B:
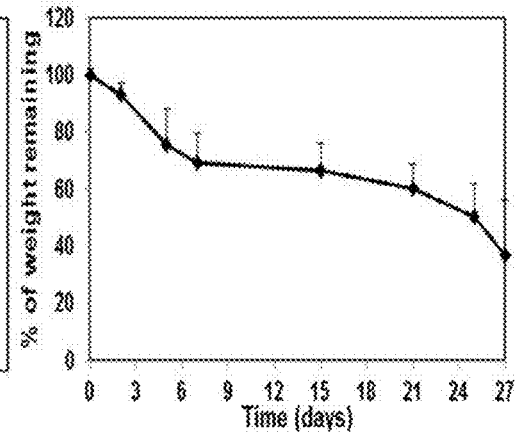

Results:

FIGS. 21A-21B illustrate the results of stability studies indicating minimal particle size variations for MDNPs incubated in DI water, media (10% serum), 0.9% saline and Gamble's solution over a period of 5 days. As FIG. 21B illustrates, MDNP degradation studies show a decrease in particle weight by about 63% in 27 days, (n=4).

FIG. 21A illustrates particle size measurements over a period of 5 days indicated that the MDNPs remained relatively stable in DI water, media containing 10% FBS, 0.9% saline and Gamble's solution. There was only about a 30% decrease in particle size by the end of the experiment (day 5). About 25% reduction in particle size was observed in all solutions by day 3. This was consistent with the degradation study results where 20% decrease in particle weight was observed by day 3 (e.g., FIG. 21B). This indicates that the MDNPs would remain stable in various solutions including body fluids without undergoing significant aggregation. Further degradation studies showed that the MDNP weight had decreased to 76% of its initial weight in 5 days. There was a gradual decrease in weight to 37% of its initial weight by day 27. This indicates that the particles had undergone slow and gradual degradation with time.

Further, drug release kinetics of the MDNPs was tested at different temperatures 37° C. (physiological temperature) and 45° C. (hyperthermia temperature) and at solutions of different pH 7.4 (physiological pH) and 6.0 (pH prevalent in acidic tumor microenvironment). The loading efficiency observed for NU7441 and gemcitabine hydrochloride was 52% and 88% respectively, calculated according to Equation (3) below:

$$\text{Loading efficiency }(\%) = \frac{\text{Total amount of drug used} - \text{Unloaded drug}}{\text{Total amount of drug used}} \times 100\% \qquad (3)$$

Figure 22A:
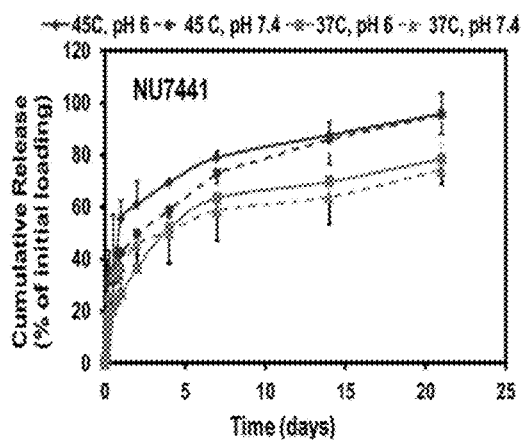
Figure 22B:
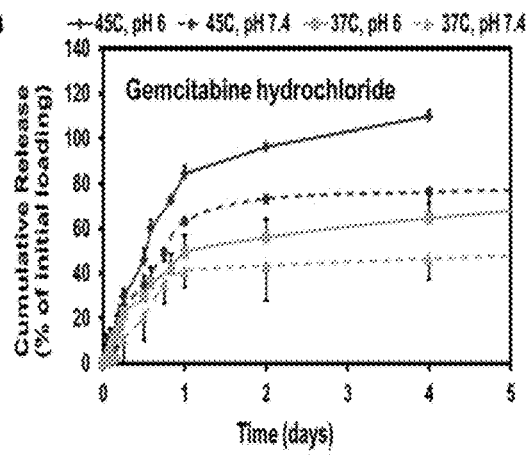

FIGS. 22A-22B illustrate the sustained release of NU7441 from the PLGA core for 21 days. This bi-phasic release is characteristic of PLGA. Gemcitabine hydrochloride loaded in the PNIPAAm-CMC shell showed temperature- and pH-dependent release with maximum release at 40° C. and pH 6.

The gemcitabine hydrochloride loaded in the PNIPAAm-CMC shell showed temperature- and pH-dependent release and achieved 100% release at 45° C., pH 6 within 2 days. At 45° C. and pH 7.4, only 85% of the encapsulated gemcitabine was released. Release under 37° C. (pH 6 and 37° C., pH 7.4 and 37° C.) conditions was found to be 82% and 52% respectively (see e.g., FIG. 22B). There was sustained release of NU7441 from the core with about 70% release at 37° C. and about 90% release at 45° C. (e.g., FIG. 22A). The bi-phasic NU77441 release pattern is characteristic of PLGA NPs, indicating that the release was dependent chiefly on PLGA degradation and subsequent drug diffusion rather than on the stimuli-sensitiveness of the PNIPAAm-CMC shell.

Example 14

In Vitro Cell Studies of MDNPs

Cytotoxicity Studies:

To study cytocompatibility of the formulated MDNPs, a 24-hour cell viability study was conducted. Human dermal fibroblasts (HDFs) and AT1 cells were seeded at a density of 5000 cells/well in a 96 well plate and allowed to attach at 37° C. and 5% $CO_2$ for 24 hours. Then the cells were incubated with varying concentrations of folic acid (0 [control], 0.1, 1, 5, 10, 15 μM) as well as MDNPs (0 [control], 100, 250, 500, 1000, 2000 μg/ml) for 24 hours. Following incubation, the cells were washed with 1× sterile PBS and cell viability was assessed using MTS and Picogreen dsDNA assays (e.g., available from Life Technologies, located in Grand Island, N.Y.) according to manufacturer's instructions. MTS assay measures the percentage of cells alive in each well compared to the controls. These findings were validated using Picogreen dsDNA assay which calculates the amount of total cell DNA present in each well compared to the control.

FIGS. 23A-23D depict in vitro folic acid cytocompatibility studies on HDFs and AT1 cells using MTS assays (FIG. 23A), Picogreen dsDNA assays (FIG. 23B) indicating good cell viability up to 10 μM concentration. In vitro cytocompatibility of MDNPs using MTS assays (FIG. 23C) and Picogreen dsDNA assay (FIG. 23D) also demonstrated that cells were viable up to a high concentration of 1 mg/mL (n=4, *$p<0.05$ w.r.t cell viability in 0 μg/ml group (FIGS. 23A, 23C) or DNA content in 0 μg/ml group (FIGS. 23B, 23D).

In vitro cytocompatibility studies using MTS assays on HDFs and AT1 cells indicated folic acid was non-toxic even at high concentrations of 10 μM (e.g., FIG. 23A). This was confirmed using Picogreen dsDNA assay which showed that the total DNA content in samples treated with 10 μM folic acid was similar to that of control samples (0 μM) (e.g., FIG. 23C). The MDNPs also showed cytocompatibility with HDFs and AT1 cells up to 1 mg/mL concentration. At all concentrations, 80% or more of the cells were viable indicating that the particles are relatively non-toxic (e.g., FIG. 23B). DNA assay results also demonstrated that >80% DNA content in each well was retained up to 1 mg/mL MDNP concentration. However a decrease in DNA content was observed in samples treated with 2 mg/mL MDNP concentration. (e.g., FIG. 23D). These results confirm that the MDNPs are cytocompatible in vitro up to 1 mg/mL concentration.

Cellular Uptake Studies:

The effect of MDNP concentration and external magnetic field on cellular uptake was also studied. A549 and H460 lung cancer cells were seeded at a density of 12,000 cells/well in a 48 well plate and incubated overnight at 37° C. and 5% CO2 to allow cell attachment. Then MDNPs at different concentrations (i.e., 0, 100, 200, 300, 500 μg/ml) were added to each well and the well plate was incubated at 47° C. for 2 hours. Uptake by cells treated with particles in the presence and absence of a 1.3 T external magnet was also studied.

This study was also repeated with human AT1 cells as well as human bronchial epithelial cells (HBECs). At the end of the uptake studies, the cells were washed thrice with 1× PBS and lysed using 1% Triton X-100. The contents in each well were analyzed using iron assay to detect amount of NPs internalized by the cells. This was normalized against the amount of cell protein per well, determined using BCA Assay. The cellular uptake was also visualized using Prussian blue iron staining and fluorescence imaging with ICG-loaded MDNPs. For this study, the cells were first incubated with the MDNPs for 2 hours following which they were washed and fixed using 1 mL of 4% paraformaldehyde solution. For Prussian blue iron staining, a solution consisting of equal parts of 20% v/v hydrochloric acid and 10% w/v potassium ferrocyanide was freshly prepared and added to the fixed cells for 20 minutes. The cells were then washed thrice with PBS and immersed in eosin stain. Then the samples were further dehydrated in 95% and 100% ethanol respectively following which they were observed under a bright field microscope. To visualize uptake of ICG-loaded particles, the fixed cells were washed following a 2 hours incubation with the NPs and then visualized using an enhanced fluorescent optical microscope (e.g., Nikon Eclipse TI, available from Nikon Instruments Inc., located in Melville, N.Y.).

A mechanism of uptake study was also conducted to determine the pathway used for uptake of the MDNPs by A549 and H460 cells. Following cell attachment by overnight incubation, the cells were first exposed to different endocytic inhibitors 10 μg/ml chlorpromazine to inhibit clathrin-dependent endocytosis, 1 μg/ml filipin III to inhibit caveloae-dependent endocytosis and 50 μM amiloride to inhibit micropinocytosis. Following 1 hour incubation with these inhibitors, the cells were washed and treated with 500 μg/ml MDNP suspension for 2 hour. This NP concentration was chosen based on the concentration at which saturation of cellular uptake had occurred in A549 and H460 cells.

Results:

Cellular uptake studies conducted using normal lung cells (AT1 cells and HBECs) as well as A549 and H460 lung cancer cell lines to determine the optimal MDNP concentration that can be taken up by the cells demonstrated that for AT1 cells and HBECs, there is magnetic-field dependent uptake and dose-dependent concentration of 300 μg/ml and 200 μg/ml respectively. However, this uptake is much smaller than what was observed in the case of A549 and H460 cells. In the case of both cancer cell lines concentration-dependent uptake was observed. Further, dependence of cellular uptake on applied external magnetic field was also studied. It was observed that a significantly higher cellular uptake of MDNPs occurred in the presence of a 1.3 T magnet for both A549 and H460 cells.

Figure 24B:
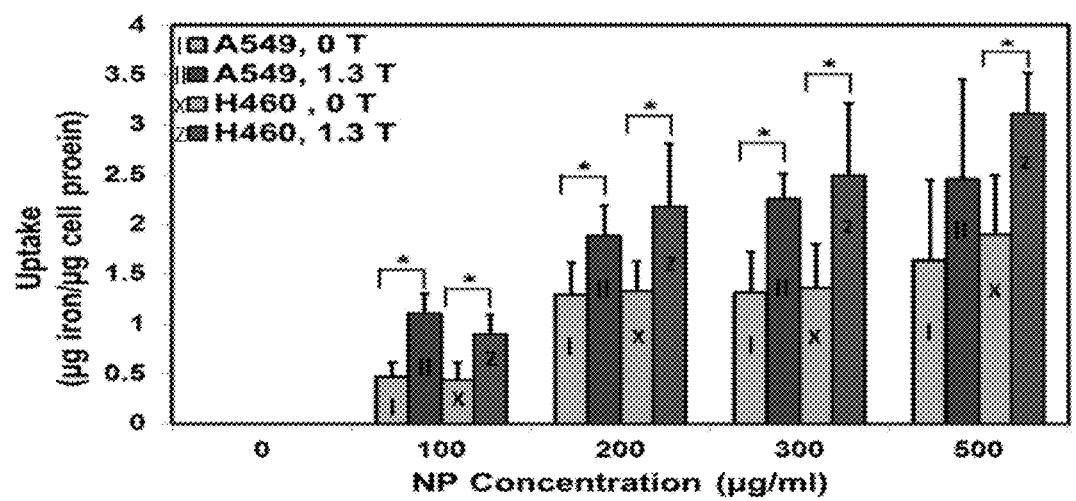

FIGS. 24A-24B illustrate in vitro cellular uptake of MDNPs by AT1 cells and Human bronchial epithelial cells (HBECs) demonstrating magnetic field-dependent uptake of MDNPs up to 300 and 200 μg/ml MDNP concentration respectively (see e.g., FIG. 24A). The MDNP uptake by A549 and H460 lung cancer cells (FIG. 24B) was dependent on NP concentration and on externally applied magnetic field (1.3 T) (n=4, *$p<0.05$).

Thus this study verified that cellular uptake of MDNPs by A549 and H460 cells was both concentration and magnetic field-dependent (FIG. 24A-B). On the other hand, uptake by healthy alveolar and bronchial epithelial cells was observed to be minimal with greater uptake occurring under the influence of an externally applied 1.3 T magnetic field. In addition, a mechanism of uptake study was conducted to determine the route of uptake of the MDNPs by A549 and H460 cells.

FIG. 25 illustrates mechanism of MDNP uptake by A549 and H460 cells. Significant reduction in MDNP uptake was observed in cells treated with filipin inhibitor suggesting that caveolae-mediated endocytosis played a key role in the uptake. Also some decrease in cellular uptake was observed in H460 and A549 cells treated with chlorpromazine suggesting that clathrin-mediated endocytosis may have also played a role in MDNP uptake($*p<0.05$ compared to Untreated group).

As shown in FIG. 25, it was observed that MDNP uptake was significantly reduced when A549 and H460 cells were treated with filipin (60% and 45% reduction respectively). This indicates that caveolae-mediated endocytosis played a key role in the uptake of the nanoparticles. The results obtained are in accordance with previous findings which show that folic acid binds to folate receptors, which are thought to be clustered around invaginated caveolae on the cell surface. Following ligand binding, the caveolae pinches the neck region and releases the folic acid into the cytosol. Then it reopens at the cell surface to enable further ligand binding. This method of endocytosis is also known as potocytosis. Significant decrease in uptake was also observed in cells treated with chloropromazine indicating that clathrin-mediated endocytosis also plays a role in MDNP uptake. However greater inhibition of MDNP uptake occurred on cells treated with filipin than with chlorpromazine.

Visualization of MDNP Uptake by H460 Cells:

Based on all the results obtained so far, H460 cells seemed to show greater affinity towards uptake of MDNPs. Greater folic acid binding was observed on H460 cells using RSI system. Also these cells showed greater dose and magnetic-field dependent uptake. Therefore H460 cells were chosen for further studies. In order to visualize in vitro uptake of MDNPs by H460 cells, Prussian blue and eosin staining was done. The particles can be visualized within the H460 cells using a bright microscope, where needed. Further ICG-loaded particles were internalized by H460 cells and can be visualized using a fluorescence microscope.

Cell Activation Studies:

The in vitro ROS production and cellular cytokine expression of AT1 cells in response to treatment with MDNPs was studied. To study cytokine production, the concentration of interleukin-1 alpha (IL-1$\infty$), interleukin-1 beta (IL-1$\beta$), interleukins 2, 4, 6, 8, 10, 12, 10A, and tumor necrosis factor-alpha (TNF-$\alpha$) in the medium was measured using Multi-Analyte ELISA Array Kit (SA Biosciences, Frederick, Md.) according to the manufacturer's directions.

Results:

FIGS. 27A-27B depict cell activation study using AT1 cells. In FIG. 27A, inflammatory cytokine release from cells following 24 hours exposure to MDNPs at two concentrations: 0.25 mg/mL and 1 mg/mL Significantly smaller quantities of IL-6, IL-8, IL-10 and TNF-$\alpha$ were produced compared to the positive control (LPS stimulated cells) (n=4, $*p<0.05$ w.r.t cytokine production by LPS-treated cells). In FIG. 27B, ROS production from cells was found to be about 16% compared to LPS control even at a high MDNP concentration of 1000 μg/ml.

Cell activation studies were conducted by incubating MDNPs with AT1 cells for 24 hours following which cytokine and ROS production from the exposed cells was analyzed. The media from each tested group (i.e., control, 0.25 mg/mL MDNPs, 1 mg/mL MDNPs) was collected for the cytokine ELISA. The cells stimulated using LPS (positive control) produced 0.25 ng/ml IL-6, 1.27 ng/ml IL-8, 0.24 ng/ml IL-10 and 0.11 ng/ml TNF-$\alpha$ inflammatory cytokines. In comparison, 0.25 mg/mL MDNPs showed significantly lower amount of, IL-6, IL-8 and IL-10 production and negligible amounts of TNF-$\alpha$ was released (FIG. 27A). Even at a high MDNP concentration of 1 mg/mL, only 0.07 ng/ml IL-6, 0.73 ng/ml IL-8, 0.05 ng/ml IL-10 and 0.02 ng/ml TNF-$\alpha$ cytokines was produced by the cells, which was significantly lower than the amounts produced by LPS stimulation.

The selected cytokines were studied, as they play major roles in inflammatory reactions. For example, IL-6 is known to be produced on exposure to acute air pollutants while IL-10 is a regulatory cytokine known to decrease inflammatory responses by inhibiting production of other inflammatory cytokines. In addition, IL-8 is known to be released in response to airway inflammation although the mechanism is unknown, while TNF-$\alpha$ is also commonly produced by alveolar epithelial cells in the case of acute inflammation and injury. The results obtained agree with previously published works on PLGA core-PNIPAm shell NPs which did not stimulate TNF-$\alpha$ production in THP1 monocytic cell line at a high concentration of 5 mg/mL. Significant TNF-$\alpha$ production was observed in the THP1 cells treated with LPS in this study, which was also observed in a previous study. Similarly, the ROS produced by the cells on exposure of 1 mg/mL MDNPs was only 16% of the ROS produced by them on LPS treatment (see e.g., FIG. 27B). These results indicate that MDNP uptake does not cause significant cell activation or initiate significant inflammatory reactions in the cells.

In vitro Clonogenic Assay:

In order to study the in vitro therapeutic efficacy of MDNPs, A549 and H460 cells were first seeded in 60 mm petri dishes and in vitro clonogenic assays were performed. A clonogenic or colony formation assay is highly sensitive and cost efficient compared to LDH, DNA and MTT assays, especially when studying monolayer cultures in vitro. Three treatment groups (Control, MDNPs without drug and MDNPs with drug) and two temperatures (47° C. and 43° C.) were used for this study. Following cell seeding, the cells were exposed to either media (control) or the respective MDNP suspensions. Then the dishes assigned to the 47° C. group were placed at 47° C. undisturbed for 10 days. Dishes assigned to 43° C. group were placed at this temperature for 1 hour following which they were moved to 47° C. and incubated for 10 days undisturbed. This was done as the cells would die due to hyperthermia if exposed to 43° C. for long periods of time. At the end of the 10-day time point, the cells were washed well with PBS, fixed and stained using crystal violet staining. The number of colonies in each dish was then counted using a light microscope.

Results:

FIGS. 26A-26B illustrate colony forming study indicating that MDNPs not loaded with drugs did not have significant effects on 11460 (e.g., FIG. 26A) and A549 (e.g., FIG. 26B) cell viability. Drug-loaded MDNPs on the other hand significantly reduced cell proliferation especially at 43° C. (LCST of the MDNP shell) indicating the chemotherapeutic effect of MDNPs on the cancer cells (n=4, $*p<0.05$ w.r.t control at 37° C.).

To assess the therapeutic efficacy of the MDNPs, a colony forming study was also conducted. The number of cell colonies in each group was counted at the end of the study. No significant cell death was observed when compared to the controls, when A549 and H460 cells were incubated with MDNPs not loaded with drugs at both 37 and 43° C. Some cell death was observed in the control and MDNPs (no drug) groups exposed to 43° C. and this might be due to hyperthermia (~80% cell death for H460 cells and ~60% cell death for A549 cells). However drug-loaded MDNPs showed significant reduction in cell proliferation at 43° C. with only 10% colonies compared to control group at 47° C. in the case of A549 cells and only 7% colonies compared to control at 47° C. for H460 cells. On the other hand, A549 and H460 cells treated with drug-loaded MDNPs at 47° C. showed 19% and 14% colonies respectively compared to the control at 47° C.

Example 15

Hemocompatibility Studies of MDNPs

Hemolysis Analysis:

In order to assess blood compatibility, a hemolysis assay was conducted on the MDNPs. Human whole blood in acid citrate dextrose anticoagulant (ACD) tubes was used for the studies. First two tubes of blood were taken and 0.9% saline and distilled water was added to prepare the negative and positive controls respectively. Distilled water is hypotonic to RBCs and this causes them to rupture. MDNPs at varying concentrations (i.e., 0, 100, 200, 300, 500 µg/ml) were placed in 1.5 mL Eppendorf tubes and 200 µl of the saline-diluted blood was added to them. The tubes were then shaken gently at 47° C. for 2 hours. Following centrifugation at 1000 g and 10 minutes, 200 µl of the supernatants were added to a 96 well plate and absorbance readings were taken at 545 nm to compare percentage of hemolysis for the experimental groups in comparison with the positive and negative controls. The percentage of hemolysis was calculated according to equation (4) below:

$$\% \text{ hemolysis} = \frac{\text{Sample } OD - \text{Negative } OD}{(\text{Positive control } OD - \text{Negative control } OD)} \times 100\% \quad (4)$$

Whole Blood Clotting:

The kinetics of whole blood clotting when exposed to the MDNPs was studied. First 0.1 M of calcium chloride (CaCl$_2$) solution was added to 8.5 mL of ACD blood to initiate blood coagulation. 50 µl of this activated blood was then added to MDNP samples of varying concentrations (0 [control], 100, 200, 300, 500 µg/ml) and incubated at room temperature. At pre-determined time points (10, 20, 30, 50 mins), 1.5 mL of DI water was added and the samples were incubated for 5 minutes more. This step was performed to lyse red blood cells (RBCs) that had not been involved in clot formation. The supernatant thus obtained contained lysed RBCs which were measured at an absorbance wavelength of 540 nm using a spectrometer. The blood clotting kinetics was also observed visually.

Hemocompatibility Results:

FIGS. 28A-28B depict hemolysis study showing less than 2% hemolysis occurrence even at an MDNP concentration of 500 µg/ml indicating that the particles are non-hemolytic. Visual observation confirmed that minimal hemolysis occurred in negative control and other experimental groups while distinct reddishness was seen in the positive control group. Blood clotting studies indicated that the amount of hemoglobin in the blood exposed to varying MDNP concentration decreased at the same rate as the control (blood not exposed to MDNPs).

Due to the presence of alveolar-capillary interface in the lungs, a few of the administered NPs could enter the blood stream over time. Therefore they should maintain good blood compatibility to avoid clot formation or other adverse inflammatory reactions. The hemolytic property of administered drug carriers should be studied extensively to ensure that they do not lyse RBCs resulting in hemoglobin release. This release could result in several critical consequences including development of anemia, jaundice, acute renal failure and eventual death. Studies have shown that formulations causing <10% hemolysis is considered to be non-hemolytic. Hemolysis study results showed that less than 2% hemolysis occurred even at 500 µg/ml MDNP concentration, indicating that these particles were non-hemolytic. Visual observation also showed reddening of the solution for the positive control indicating hemolysis while no visual indication of hemolysis could be seen for the negative control and experimental groups (blood exposed to 100, 200, 300 and 500 µg/ml MDNP concentrations).

Further, blood clotting studies were conducted to ensure that the MDNPs will not promote clot formation on entering the blood stream. DI water addition causes lysis of unclotted RBCs in the samples. The hemoglobin released from these lysed RBCs can be quantified at 540 nm absorbance wavelength using a spectrometer. Therefore, the absorbance readings obtained at 540 nm is inversely proportional to clot formation. The absorbance values for all experimental samples decreased gradually indicating clot formation in the tubes aligning with time. The MDNPs at varying concentrations ranging from 100 to 500 µg/ml showed the same blood clotting rate as the control group (whole blood not exposed to NPs). This was visually confirmed, and the solution for the control group and 500 µg/ml group had comparatively clearer supernatants at 60 mins than at other time points. The clot formation is clearly visible in both experimental groups during the 30 and 60 min time-point.

Example 16

In Vivo Imaging and Therapeutic Efficacy of MDNPs

All animal procedures were approved by the Institutional Animal Care and Use Committee (IACUC) at the UTSW. For preliminary in vivo study, H460 tumors were induced in the hind limbs of female athymic nude mice. The animals were monitored in terms of their weights, and tumor volume. When the tumor volume reached about 100 mm$^3$, they were imaged using non-invasive MRI with a 4.7 T Varian small animal scanner. Multi-echo multi-slice T2 images (TR=2500 ms; TE=10 ms; field of view of 40 mm×40 mm; matrix=256×256; slice thickness=1 mm) were obtained. Then the animals were randomly assigned to different groups: control, unconjugated MDNPs, folic acid-conjugated MDNPs. Intra-tumoral injection of MDNPs was done to mimic the localized delivery of particles seen following nebulization to the lungs. About 24 hours post particle injection; the animals were imaged again using MRI. Then the animals were sacrificed and Prussian blue staining done on the tumor sections to detect the presence of iron oxide. The MR imaging of animals was also used to confirm if more folic acid-conjugated MDNPs will be retained in the tumor region compared to the unconjugated MDNPs.

The animal procedure for this study was approved by the IACUC at UTSW. In order to establish the therapeutic efficacy of the MDNPs, female athymic nude mice were injected with 1×106 H460 cancer cells in the hind limbs and tumor volume and weight were measured over time. Once the tumor reached 100 mm$^3$ of volume, the mice were randomly assigned to the different groups (Sham control, Drug cocktail, Drug cocktail+Radiation, MDNPs without drugs, MDNPs with drugs+Radiation). All animals were anesthetized by 1% isoflurane inhalation following which they were administered the different solutions by intra-tumoral injections. Intra-tumoral injections have also been adopted previously to study the localized therapeutic efficacy of NPs for inhalational drug delivery. Therefore this method of administration was chosen to mimic localized delivery of NPs which will be seen following inhalation. The injections were given on alternate days for 2 weeks. Tumors requiring radiation were treated with a radiation dose of 2 Gy per treatment day (Source to Surface Distance—20 cm, Dose rate—16.64 Gy/min) using an X-RAD320 (e.g., Precision X-Ray, located in North Branford, Conn.) biological irradiator. 24 hours following injection, for the duration of the study. Tumor volumes and animal weights were measured and recorded prior to the injections at each time point. In Vivo Investigation Results:

FIGS. 29A-29D depict MR images of the control group before and after saline injection. MR images of animals treated with folic acid-conjugated MDNPs before and after injection. A distinct darkening of the tumor was observed post injection.

FIG. 29E illustrates the significant T2 signal intensity drop, which was observed in the case of folic acid-conjugated MDNPs indicating that there was greater negative contrast compared to the pre-injection scans, due to the presence of iron oxide in the tumor.

Tumors were visualized before and 24 hours after intra-tumoral injection of MDNPs into H460 tumor bearing mice. The darkening of the tumor region 24 hours following injection of the folic acid-conjugated MDNPs were clearly visualized (FIGS. 29A-D). T2 signal intensity in the tumors was found to drop significantly by 30% in animals treated with folic acid-conjugated MDNPs compared to the tumor signal intensity before treatment. Control (untreated) animals and the animals treated with unconjugated MDNPs showed signal intensity drops of about 3.5% and 12% respectively compared to the intensity before treatment (e.g., FIG. 29E).

Prussian blue staining of the tumors was carried out and the sections were visualized at 10× magnification. More iron could be seen in the tumor sections treated with folic acid-conjugated MDNPs compared to sections treated with unconjugated MDNPs, 24 hours post treatment. This indicates that the folic acid-conjugated MDNPs were retained longer in the tumor following administration.

FIGS. 30A-30C are graphical representations of the changes in tumor volume for each group as a percentage of their initial volume at the beginning of the study. Tumor volumes for each group excluding the Control group showing significant slower tumor growth rate in the case of 'NU7441+Gem+RT' group and the 'Drug-loaded MDNPs+RT' group compared to other treatment groups at days 8, 10 and 12 (n=4, *p<0.05 for 'Drug-loaded MDNPs+RT' group compared to other treatment groups) Ex vivo tumor volumes of the different treatment groups at day 12 demonstrating the much smaller tumor size of 'Drug-loaded MDNPs+RT' group compared to the other groups (n=2).

Further, the efficacy of drug-loaded MDNPs was studied in H460-tumor bearing athymic nude mice. For RT, the mice were placed under anesthesia in the X-RAD320 chamber and a probe was used to deliver the radiation dose specifically to the tumor. In this preliminary proof-of-principle study, the external tumor volume of all animals was measured prior to the injections for the duration of the study and plotted as a percentage of initial tumor volume (see, FIGS. 30A-C). It was observed that the tumors in control (sham) group grew exponentially to 6000% of their initial volume within 12 days. On the other hand, tumors in 'MDNPs only' (not drug-loaded) group and 'drug cocktail' (NU7441+Gemcitabine) group grew to 2400% and 1200% of their initial volumes respectively. The comparatively slower tumor growth rate in the 'MDNPs only' group compared to the sham control group could be due to possible release and subsequent toxicity of SPIO from the particles. This can be overcome by replacing SPIO with FDA-approved Feraheme or other MR contrast agents such as manganese or gadolinium for future studies. The tumor inhibitory effect of the drug cocktail can be attributed to therapeutic effect of gemcitabine hydrochloride which was released from the shell. On providing RT only, the tumor growth on day 12 was only 535% of the initial volume.

However significant inhibition of tumor growth was observed in 'drug cocktail+RT' group and 'drug-loaded MDNPs+RT' groups whose tumor volumes at day 12 were 506% and 377% of their initial tumor volumes respectively. This indicates that the drug-radiosensitizer combination used is effective in slowing down tumor growth when used in combination with RT. The MDNPs could potentially overcome the systemic side effects that may occur on administering the free drug cocktail due to its controlled release properties and targeting capabilities. The targeting capabilities of the MDNPs have already been confirmed using in vivo MRI were folic acid-conjugated particles were retained longer in the tumor.

Following treatment, the animals were sacrificed and the tumors excised for ex vivo volume measurements and visual observation. It was seen that tumors of animals treated with drug loaded particles+RT were significantly smaller than tumors from animals in the other treatment groups at the end of the study. Preliminary results obtained, thus indicate the potential of the MDNPs as carriers of therapeutic agents for controlled and localized lung cancer therapy.

Example 17

In Vitro and In Vivo Studies

FIGS. 31A-31C graphically illustrate results from in vitro and in vivo studies according to some embodiments described herein. MDNPs containing Cisplatin and a DNA DSB repair inhibitor NU7441 in vitro as well as in vivo in orthotopic rat lung tumor models.

Cell viability experiments were performed in A549 NSCLC cells exposed to the following treatments; no treatment, empty NPs, MDNPs (MDNPs loaded with both cisplatin and NU 74441) over a period of 72 hours. There was a modest cell death of about 30% at 72 hours in the presence of MDNPs (see e.g., FIG. 31A).

In the next study, radiation was combined with MDNPs, and colony formation assay as described in the approach section was performed to investigate the therapeutic efficacy of the combined treatment. Based on the drug release pattern and after plating, A549 cells were exposed to MDNPs for at least 7 hours prior to radiation treatment to ensure a sufficient level of drugs were available at the time of radiation treatment (4 Gy). Similar results were also noticed in the colony formation assay in response to MDNPs (e.g., MDNPs loaded with NU7441 and cisplatin) alone, as shown in FIG. 31B. However, a significant level of clonogenic cell death was noticed in the radio-chemotherapy group using MDNPs (see e.g., FIG. 31B, group MDNP+4G in which the cells were exposed to the combined treatment of MDNPs and radiation).

In vivo therapeutic efficacy of localized radio-chemotherapy in orthotopic lung tumors rats. NPs were delivered via nebulization in rats. The control NPs and MDNPs were suspended in 0.3-0.5 mL saline and nebulized (e.g., 2-4 μm droplets) into the circuit.

In FIG. 31C, efficacy of the combined treatment of MDNPs and radiation is shown. For example, orthotopic tumors using H460 line were developed in the rat lung. Once the BLI signal reached about 107 photons/sec (e.g., about 6 to 8 mm in diameter), subjects were randomized and divided into groups (i.e., control, MDNP, radiation, and MDNP+ radiation). Control NP and MDNPs (1 mg each time/subject) were given to subjects (i.e., rats) for two consecutive days (24 hours apart). Via nebulization under un-sedated condition, radiation treatment (8 Gyx1) was performed 24 hours after the last NPs treatment using image guidance and a smart planning system. Tumor growth was monitored weekly by bioluminescence imaging.

The results in FIG. 31C clearly indicate that the combined treatment significantly slowed the tumor progression. Further optimizations in regards to the doses of radiation and MDNPs in different NSCLC lines are ongoing.

Example 18

Dose Enhancement Ratio (DER)

A panel of NSCLC cells with different genetic backgrounds is used for determining DER, which is generally calculated as the dose (Gy) for radiation alone divided by the dose for radiation plus drugs for a surviving fraction of 0.25. The determination of DER is needed since the radiation dose might be significantly less when combined with a drug, while the killing effect is the same.

The IC50 dose of the MDNPs using CFA on cancer cells exposed to different doses of drug-loaded MDNPs. Based on the IC50 values, the radiation response using CFA is determined. For example, log phase cells will be trypsinized, counted, and diluted serially to appropriate concentrations for plating. After 3-4 hours of incubation, cells are treated with drug-loaded MDNPs (IC50 and IC25 doses) for 4 hours followed by graded doses of IR (e.g., 2, 4, 6, and 8 Gy). After 7 days, cells are fixed with 70% ethanol and stained with 0.05% crystal violet in PBS. Colonies containing >50 cells are counted, and DER will be calculated.

Example 19

Effects of IR Using Three-Dimensional (3-D) Organotypic Human Lung Models

A physiological 3D human lung cell culture model can assist with understanding how MDNPs effect cell toxicity and influence the efficacy of radiotherapy and combined therapy in vivo. Organotypic 3D cultures of human bronchial epithelial cells (HBECs) that rest on top of a lung stromal fibroblast matrix in an air-medium interface are provided. Under these conditions, the HBECs differentiate into tissue-specific structures mimicking those found in a normal lung as seen in FIG. 32A.

Immunostaining for phospho-histone 3 (pH3), a marker of mitosis, indicated that the 3D structures consisted of very few M-phase cells. Pulse labeling with BrdU as seen in FIGS. 32B-32C, followed by flow cytometry analysis showed that >80% of the cells were in the G1 phase and only <4% of the cells were in the S-phase. This is the first 3D model developed and applied for examining the effect of MDNPs on normal human lungs and drug-loaded MDNPs+ radiation on normal human lungs and tumors.

To determine the impact of drug-loaded MDNPs on cellular proliferation, apoptosis, and DDR signaling in response to radiation, 3D culture models are pre-treated with drug-loaded MDNPs and then irradiated with 1-5 Gy. Subsequently, to assess cellular proliferation, FACS are periodically performed (e.g., 24 hours to 15 days) after pulse-labeling cells in 3D culture with BrdU, apoptosis is measured by FACS-based TUNEL assay, and DDR signaling is characterized using a panel of anti-DDR factors by western blotting, as described above.

Example 20

In Vivo Therapeutic Efficacy of MDNPs

The therapeutic efficacy of the combined treatment using drug-loaded MDNPs in orthotopic lung tumor models in rats is evaluated. As described above, a 3D tumor model for image guided radiation is provided. Not only that, a sophisticated treatment plan can be generated to give any dose of radiation using multiple beams.

FIGS. 33A-33F show the delivery of 18 Gy to the tumor using 24 parallel opposed beams. In addition, a dose volume histogram in FIG. 33E depicts dose coverage to the contoured tumor volume and the non-tumor lung, highlighting a clinically acceptable dose to the non-tumor lung. The combined effect of high dose/fraction of radiation with MDNPs instead of the conventional fractionated radiation will be studied. Inhalation delivery of MDNPs with and without drug loading to the lungs and lung tumors in the animals via nebulization in an un-sedated condition will be performed as described above. The radiation dose will be either 1 or 3 fractions of between 8 to 12 Gy every 48 hours.

The following groups were established: Group 1: Control (no treatment, vehicle only); Group 2: MDNPs alone; Group 3: Radiation; Group 4: Drug-loaded MDNPs administrated +1×RT, RT; Group 5: Drug-loaded MDNPs+2×RT. The selection of radiation dose will depend on the intrinsic radiation sensitivity (SF2 values) of the cell lines. For example, in the case of A549, it is found that 12GyX3 is the tumor ablative dose, whereas in the case of H460, 8GyX1 is the tumor ablative dose; in both cases tumor diameter was about 8 to 10 mm at the time of radiation.

After treatment, efficacy can be assessed by measuring the body weight, tumor volume, and animal survival rate over a time range as well as the use of standard histological and biological analysis of tumor and other organ tissues as described earlier. At the end of this study, it is desirable to achieve maximum tumor growth inhibition without incidence of tumor relapse or metastasis in response to MDNPs and radiation therapy.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

What is claimed is:
1. A method of diagnosing and/or treating a cancer; the method comprising:
    administering to a patient in need thereof a population of core-shell nanoparticles, the core-shell nanoparticles comprising:

a core component;

a shell component encapsulating the core component;

one or more radiosensitizers disposed in the core component; and one or more chemotherapeutic agents disposed in the shell component, wherein the core component is formed from one or more biodegradable polymers; and wherein the shell component is formed from one or more stimuli responsive polymers that undergo a reversible phase transition in response to an external stimulus;

exposing the core-shell nanoparticles to the external stimulus;

releasing a portion of the chemotherapeutic agents in a burst release from the shell component in response to the exposure to the external stimulus; and releasing a portion of the radiosensitizers in a sustained release from the core component in response to the exposure to the external stimulus.

2. The method of claim 1, wherein the core component is formed from a gelatin, chitosan, alginate, starch, polysaccharide, cellulose or cellulose derivative, dextrin, dextran, fibrin, fibrinogen, fibronectin, collagen, elastin, laminin, glycosaminoglycan, hyaluronic acid, albumin, polypeptide, polylactic acid (PLA), polyglycolic acid (PGA), polylactic-co-glycolic acid (PLGA), polycaprolactone (PCL), polyglycolide, polyanhydride, polyphosphazene, polyurethane, PLGA-chitosan copolymer, PLGA-PEG (polyethylene glycol) copolymer, or a mixture or combination thereof.

3. The method of claim 2, wherein the core component is formed from PLGA.

4. The method of claim 1, wherein the shell component is temperature-responsive.

5. The method of claim 1, wherein the shell component is pH responsive.

6. The method of claim 1, wherein the shell component is formed from a copolymer of a temperature-responsive first polymer and a pH-responsive second polymer, wherein the first and second polymers differ.

7. The method of claim 6, wherein the shell component is formed from a poly(N-isopropylacrylamide) (PNIPAAm)-carboxymethyl chitosan (CMC) copolymer.

8. The method of claim 1, wherein the core-shell nanoparticles further comprise a magnetic resonance imaging (MRI) contrast agent or a computed tomography (CT) contrast agent disposed in the core component and/or the shell component.

9. The method of claim 8, wherein the contrast agent comprises superparamagnetic iron oxide (SPIO) or a lanthanide ion.

10. The method of claim 1, wherein the composition further comprises an imaging agent disposed in the core component and/or the shell component.

11. The method of claim 10, wherein the imaging agent comprises an organic dye, luminescent biomolecule, or a semiconductor nanocrystal.

12. The method of claim 1, wherein the core-shell nanoparticles further comprise a targeting agent attached to the outer surface of the core-shell nanoparticles.

13. The method of claim 12, wherein the targeting agent comprises folic acid.

14. The method of claim 1, wherein the population of core-shell nanoparticles has an average diameter of 300 nm or less.

15. The method of claim 1, wherein the population of core-shell nanoparticles has a negative zeta potential.

16. The method of claim 15, wherein the negative zeta potential has an absolute value of 10 mV or more.

17. The method of claim 16, wherein the negative zeta potential has an absolute value of 10-40 mV.

18. The method of claim 1, wherein releasing the portion of the chemotherapeutic agents and releasing the portion of the radiosensitizers begin simultaneously.

19. A method of diagnosing and/or treating a cancer, the method comprising:

administering to a patient in need thereof a population of core-shell nanoparticles, the core-shell nanoparticles comprising:

a core component;

a shell component encapsulating the core component;

one or more radiosensitizers disposed in the core component; and one or more chemotherapeutic agents disposed in the shell component, wherein the core component is formed from one or more biodegradable polymers; and wherein the shell component is formed from one or more stimuli responsive polymers that undergo a reversible phase transition in response to an external stimulus;

exposing the core-shell nanoparticles to the external stimulus, releasing a portion of the chemotherapeutic agents in a burst release from the shell component in response to the exposure to the external stimulus; and releasing a portion of the radiosensitizers in a sustained release from the core component in response to the exposure to the external stimulus, wherein the composition is administered to the patient as an aerosol or an inhalant via a nebulizer and wherein the cancer is lung cancer.

20. The method of claim 1, wherein the radiosensitizers, chemotherapeutic agents, or both are releasable from the core-shell nanoparticles in the presence of the external stimulus and are unreleasable in the absence of the external stimulus.

21. The method of claim 1, wherein the burst release corresponds to a release of at least 20% of the chemotherapeutic agents within a period of 2 days or less.

22. The method of claim 1, wherein the sustained release corresponds to a release of less than 20% of the radiosensitizers within 2 days.

23. The method of claim 1, wherein the external stimuli comprises radiation therapy.

24. The method of claim 23, wherein the radiation therapy comprises external beam radiation therapy, brachytherapy, or systemic radioisotope therapy.

25. The method of claim 1, wherein the external stimuli comprises an applied external magnetic field.

26. The method of claim 5, wherein the pH-responsive shell material is a pH-responsive polymer.

* * * * *